United States Patent [19]
Reed

[11] Patent Number: 5,831,066
[45] Date of Patent: Nov. 3, 1998

[54] REGULATION OF BCL-2 GENE EXPRESSION

[75] Inventor: John C. Reed, Carlsbad, Calif.

[73] Assignee: The Trustees of the University of Pennsylvania, Philadelphia, Pa.

[21] Appl. No.: 465,485

[22] Filed: Jun. 5, 1995 Related U.S. Application Data

Related U.S. Application Data

[63] Continuation of Ser. No. 124,256, Sep. 20, 1993, abandoned, which is a continuation-in-part of Ser. No. 840,716, Feb. 21, 1992, abandoned, which is a continuation-in-part of Ser. No. 288,692, Dec. 22, 1988, abandoned.

[51] Int. Cl.$^6$ .......................... C07H 21/04; C12N 15/85; C12N 15/12
[52] U.S. Cl. .................. 536/24.5; 435/172.3; 435/320.1; 435/325; 536/23.5
[58] Field of Search .................................. 536/23.5, 24.5; 514/44; 435/320.1, 172.3, 325

[56] References Cited

U.S. PATENT DOCUMENTS

| | | |
|---|---|---|
| 4,999,290 | 3/1991 | Lee . |
| 5,015,568 | 5/1991 | Tsujimoto et al. . |
| 5,098,890 | 3/1992 | Gewirtz . |
| 5,149,628 | 9/1992 | Croce . |
| 5,202,429 | 4/1993 | Tsujimoto et al. . |
| 5,585,479 | 12/1996 | Hoke et al. .............................. 536/24.5 |

FOREIGN PATENT DOCUMENTS

WO 94/27426   12/1994   WIPO .

OTHER PUBLICATIONS

Orkin SH, et al. "Report and Recommendations of the Panel to Assess the NIH Investment in Research on Gene Therapy.", Dec. 7, 1995.

Toshiyuki Miyashita et al, Cancer Research, vol. No. 52, pp. Nos. 5407–5411, Oct. 1, 1992.

Toshiyuki Miyashita et al, Blood, vol. No. 81, pp. Nos. 151–157, Jan. 1, 1993.

J. C. Reed et al, Annals of Oncology, 1993, pp. Nos. 61–65.

F. E. Cotter et al, Oncogene, vol. No. 9, pp. Nos. 3049–3055, Oct. 1994.

Shinichi Kitada et al, Antisense Research and Development, vol. No. 4, pp. Nos. 71–79, Summer 1994.

Shinichi Kitada et al, Antisense Research and Development, vol. No. 3, pp. Nos. 157–169, Summer 1993.

Reed et al, Cancer Res., 50, p. No. 5656, 1990.

Williams, Cell 65, p. No. 1097, 1991.

Strasser et al, Cell 67, p. No. 889, 1991.

Patent Cooperation Treaty (PCT) International Search Report dated Jan. 12, 1995.

C. Paoletti, "Anti–Sense Oligonucleotides as Potential Antitumour Agents: Prospective Views and Preliminary Results," Anti–Cancer Drug Design, vol. 2, p. Nos. 325–331, 1988.

Stein et al, "Oligodeoxynucleotides as Inhibitors of Gene Expression: A Review," Cancer Research, vol. 48, p. Nos. 2659–2668, May 15, 1988.

Eugen Uhlmann et al. "Antisense Oligonucleotides: A New Therapeutic Principle," Chemical Reviews, vol. 90, No. 4, p. Nos. 544–584, Jun. 1990.

Tsujimoto, Y., et al, Proc. Natl. Acad. Sci. USA, vol. 83, p. Nos. 5214–5218, Jul. 1986.

Negrini, M., et al, Cell, vol. 49, p. Nos. 455–463, 1987.

Reed, J., et al, Science, vol. 236, p. Nos. 1295–1299, Jun. 5, 1987.

*Primary Examiner*—David T. Fox
*Assistant Examiner*—Amy J. Nelson
*Attorney, Agent, or Firm*—Oblon, Spivak, McClelland, Maier & Neustadt, P.C.

[57] ABSTRACT

The present invention provides novel anticode oligomers and methods of using them for controlling the growth of cancer cells expressing the bcl-2 gene.

41 Claims, 20 Drawing Sheets

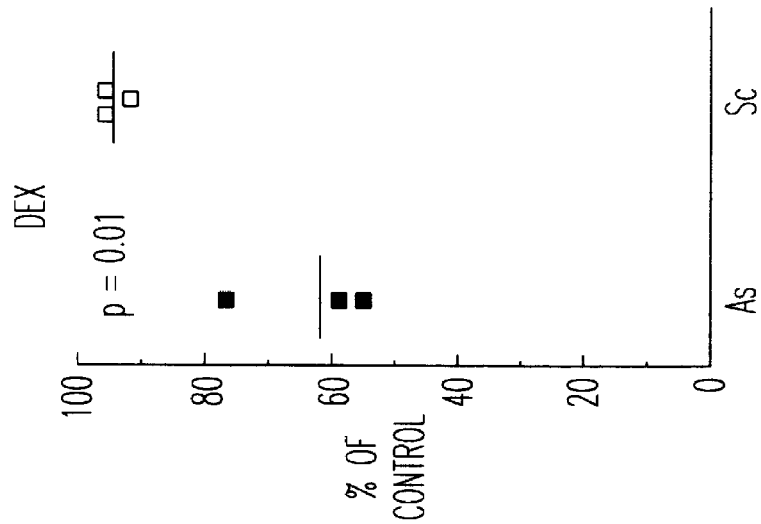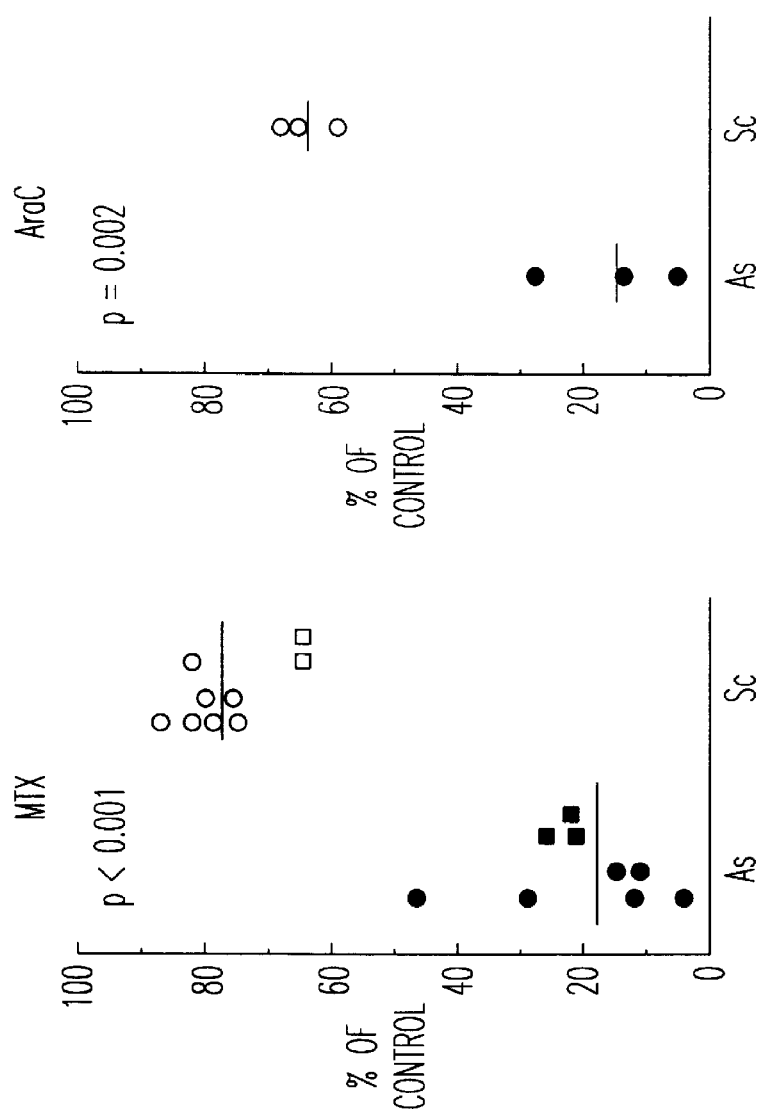

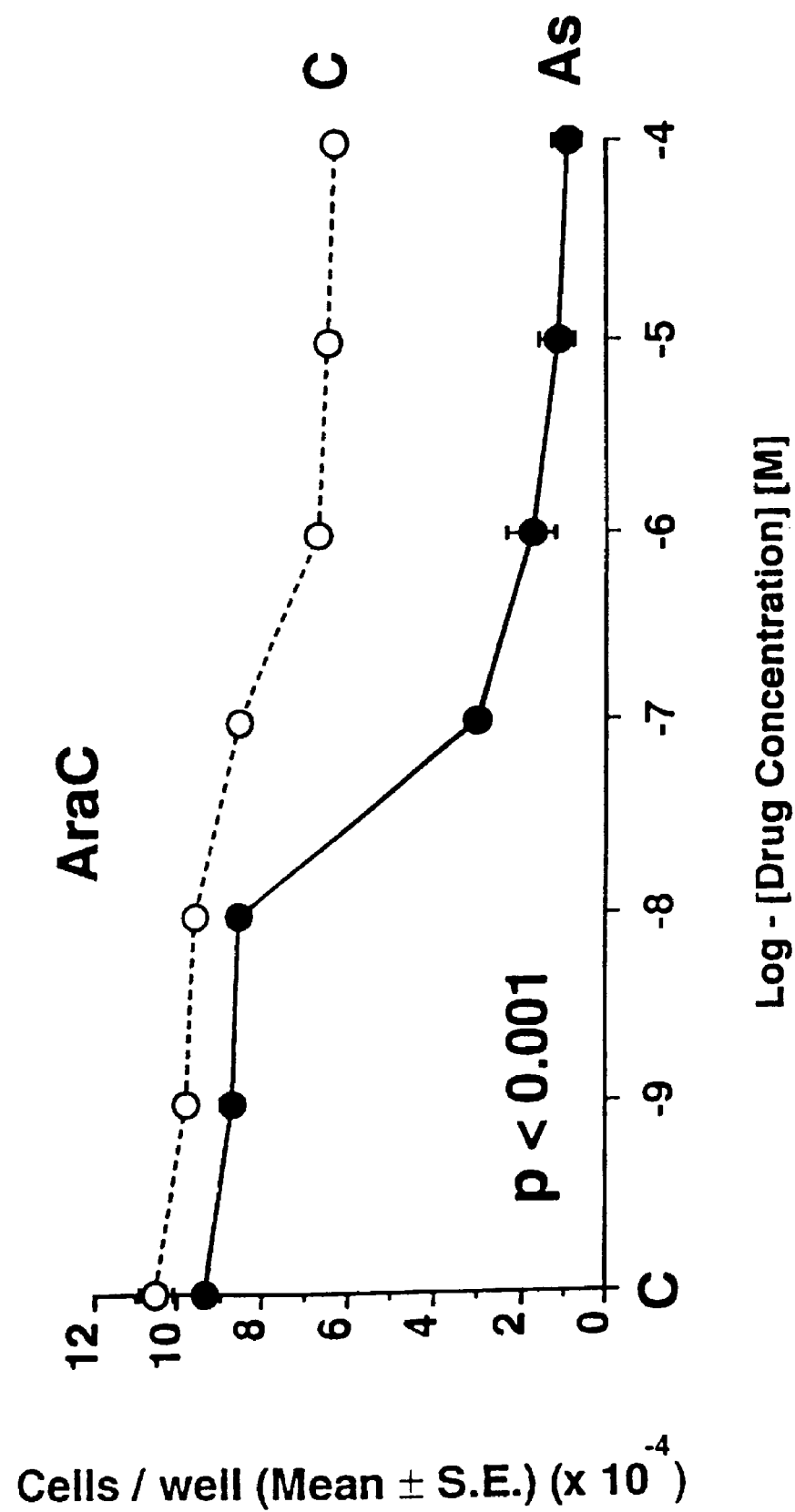
FIG. 10B(1)

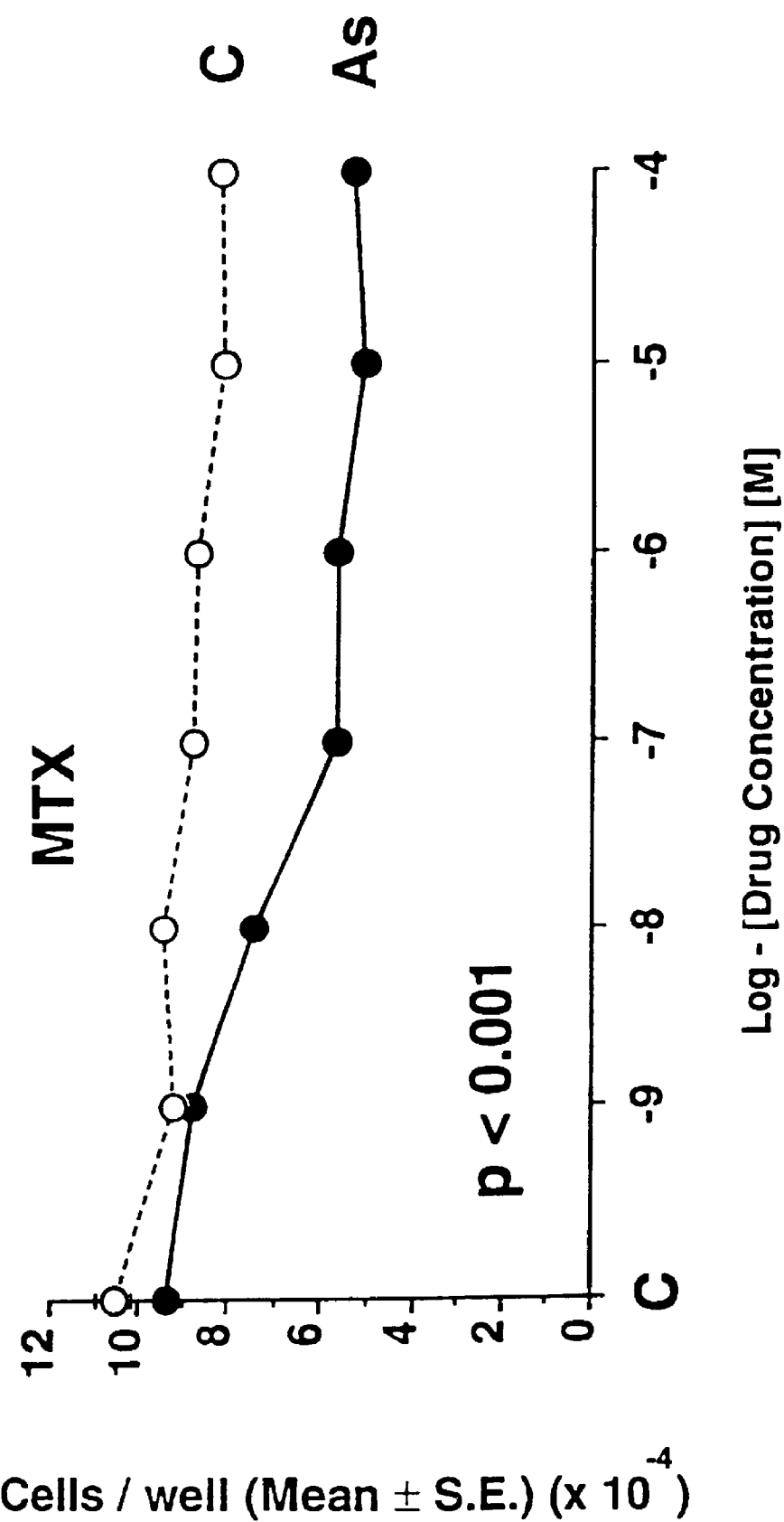
FIG. 10B(2)

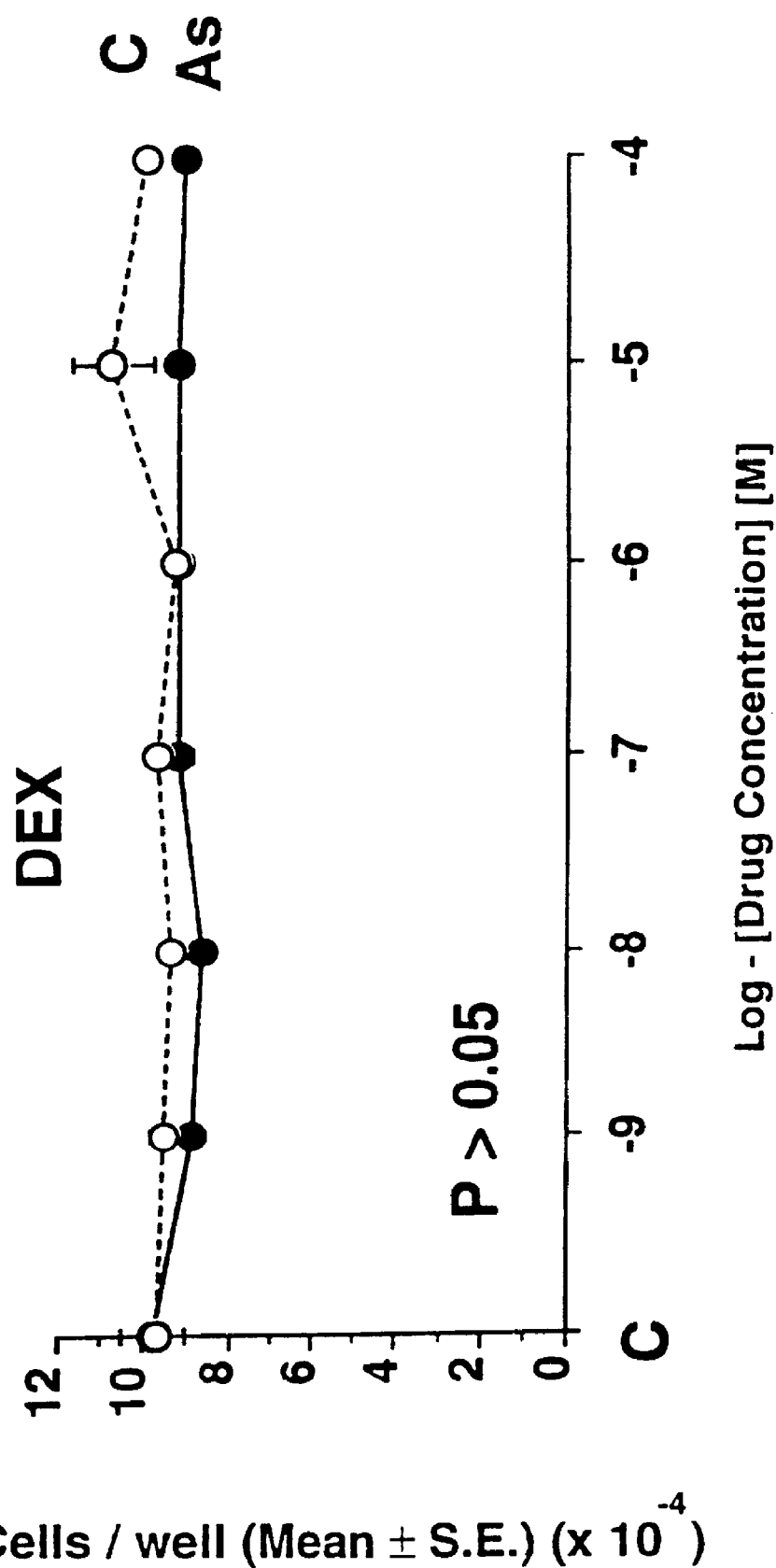
FIG. 10B (3)

As-18'mer
5'-TCTCCCAGCGTGCGCCAT-3'
Sc-18'mer
5'-TGCACTCACGCTCGGCCT-3'

As23
5′-GCGCGGCGGGCGGGCGGGCA-3′
Sc23
5′-GGGCGGAGGCCGGCCGGCGG-3′

As72
5'-AGCGGCGGCGGCGGCAGCGC-3'
Sc72
5'-GGGCCGGGAAGGGCGCCCGC-3'

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:1:

CAGCGTGCGC CATCCTTCCC        20

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:2:

CTTTTCCTCT GGGAAGGATG GCGCACGCTG GGAGA        35

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:3:

GATGCACCTA CCCAGCCTCC        20

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:4:

ACGGGGTACG GAGGCTGGGT AGGTGCATCT GGT                                33

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:5:

ACAAAGGCAT CCTGCAGTTG                                               20

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:6:

CCCCCAACTG CAGGATGCCT TTGTGGAACT GTACGG                             36

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:7:

GGGAAGGATG GCGCACGCTG                                               20

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:8:

CGCGTGCGAC CCTCTTG                                                  17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:9:

TACCGCGTGC GACCCTC                                                                                           17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:10:

TCCTACCGCG TGCGACC                                                                                           17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:11:

CCTTCCTACC GCGTGCG                                                                                           17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:12:

GACCCTTCCT ACCGCGT                                                                                           17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:13:

GGAGACCCTT CCTACCG                                                                                           17

( 2 ) INFORMATION FOR SEQ ID NO:14:

( i ) SEQUENCE CHARACTERISTICS:

(A) LENGTH: 15 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:14:

GCGGCGGCAG CGCGG 15

(2) INFORMATION FOR SEQ ID NO:15:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:15:

CGGCGGGGCG ACGGA 15

(2) INFORMATION FOR SEQ ID NO:16:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:16:

CGGGAGCGCG GCGGGC 16

(2) INFORMATION FOR SEQ ID NO:17:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:17:

TCTCCCAGCG TGCGCCAT 18

(2) INFORMATION FOR SEQ ID NO:18:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:18:

TGCACTCACG CTCGGCCT 18

(2) INFORMATION FOR SEQ ID NO:19:

(i) SEQUENCE CHARACTERISTICS:
(A) LENGTH: 5086 base pairs
(B) TYPE: nucleic acid
(C) STRANDEDNESS: single (D) TOPOLOGY: linear (xi) SEQUENCE DESCRIPTION: SEQ ID NO:19:

| | | | | | | |
|---|---|---|---|---|---|---|
| GCGCCCGCCC | CTCCGCGCCG | CCTGCCCGCC | CGCCCGCCGC | GCTCCCGCCC | GCCGCTCTCC | 60 |
| GTGGCCCCGC | CGCGCTGCCG | CCGCCGCCGC | TGCCAGCGAA | GGTGCCGGGG | CTCCGGGCCC | 120 |
| TCCCTGCCGG | CGGCCGTCAG | CGCTCGGAGC | GAACTGCGCG | ACGGGAGGTC | CGGGAGGCGA | 180 |
| CCGTAGTCGC | GCCGCCGCGC | AGGACCAGGA | GGAGGAGAAA | GGGTGCGCAG | CCCGGAGGCG | 240 |
| GGGTGCGCCG | GTGGGGTGCA | GCGGAAGAGG | GGGTCCAGGG | GGGAGAACTT | CGTAGCAGTC | 300 |
| ATCCTTTTTA | GGAAAAGAGG | GAAAAAATAA | AACCCTCCCC | CACCACCTCC | TTCTCCCCAC | 360 |
| CCCTCGCCGC | ACCACACACA | GCGCGGGCTT | CTAGCGCTCG | GCACCGGCGG | GCCAGGCGCG | 420 |
| TCCTGCCTTC | ATTTATCCAG | CAGCTTTTCG | GAAAATGCAT | TTGCTGTTCG | GAGTTTAATC | 480 |
| AGAAGACGAT | TCCTGCCTCC | GTCCCGGCT | CCTTCATCGT | CCCATCTCCC | CTGTCTCTCT | 540 |
| CCTGGGGAGG | CGTGAAGCGG | TCCCGTGGAT | AGAGATTCAT | GCCTGTGTCC | GCGCGTGTGT | 600 |
| GCGCGCGTAT | AAATTGCCGA | GAAGGGGAAA | ACATCACAGG | ACTTCTGCGA | ATACCGGACT | 660 |
| GAAAATTGTA | ATTCATCTGC | CGCCGCCGCT | GCCAAAAAAA | AACTCGAGCT | CTTGAGATCT | 720 |
| CCGGTTGGGA | TTCCTGCGGA | TTGACATTTC | TGTGAAGCAG | AAGTCTGGGA | ATCGATCTGG | 780 |
| AAATCCTCCT | AATTTTTACT | CCCTCTCCCC | CCGACTCCTG | ATTCATTGGG | AAGTTTCAAA | 840 |
| TCAGCTATAA | CTGGAGAGTG | CTGAAGATTG | ATGGGATCGT | TGCCTTATGC | ATTTGTTTTG | 900 |
| GTTTTACAAA | AAGGAAACTT | GACAGAGGAT | CATGCTGTAC | TTAAAAAATA | CAAGTAAGTC | 960 |
| TCGCACAGGA | AATTGGTTTA | ATGTAACTTT | CAATGGAAAC | CTTTGAGATT | TTTTACTTAA | 1020 |
| AGTGCATTCG | AGTAAATTTA | ATTTCCAGGC | AGCTTAATAC | ATTGTTTTA | GCCGTGTTAC | 1080 |
| TTGTAGTGTG | TATGCCCTGC | TTTCACTCAG | TGTGTACAGG | GAAACGCACC | TGATTTTTA | 1140 |
| CTTATTAGTT | TGTTTTTTCT | TTAACCTTTC | AGCATCACAG | AGGAAGTAGA | CTGATATTAA | 1200 |
| CAATACTTAC | TAATAATAAC | GTGCCTCATG | AAATAAAGAT | CCGAAAGGAA | TTGGAATAAA | 1260 |
| AATTTCCTGC | GTCTCATGCC | AAGAGGGAAA | CACCAGAATC | AAGTGTTCCG | CGTGATTGAA | 1320 |
| GACACCCCCT | CGTCCAAGAA | TGCAAAGCAC | ATCCAATAAA | ATAGCTGGAT | TATAACTCCT | 1380 |
| CTTCTTTCTC | TGGGGGCCGT | GGGGTGGGAG | CTGGGCGAG | AGGTGCCGTT | GGCCCCGTT | 1440 |
| GCTTTTCCTC | TGGGAAGGAT | GGCGCACGCT | GGGAGAACGG | GGTACGACAA | CCGGGAGATA | 1500 |
| GTGATGAAGT | ACATCCATTA | TAAGCTGTCG | CAGAGGGCT | ACGAGTGGGA | TGCGGGAGAT | 1560 |
| GTGGGCGCCG | CGCCCCCGGG | GGCCGCCCCC | GCACCGGGCA | TCTTCTCCTC | CCAGCCCGGG | 1620 |
| CACACGCCCC | ATCCAGCCGC | ATCCCGCGAC | CCGGTCGCCA | GGACCTCGCC | GCTGCAGACC | 1680 |
| CCGGCTGCCC | CCGGCGCCGC | CGCGGGGCCT | GCGCTCAGCC | CGGTGCCACC | TGTGGTCCAC | 1740 |
| CTGGCCCTCC | GCCAAGCCGG | CGACGACTTC | TCCCGCCGCT | ACCGCGGCGA | CTTCGCCGAG | 1800 |
| ATGTCCAGCC | AGCTGCACCT | GACGCCCTTC | ACCGCGCGGG | GACGCTTTGC | CACGGTGGTG | 1860 |
| GAGGAGCTCT | TCAGGGACGG | GGTGAACTGG | GGGAGGATTG | TGGCCTTCTT | TGAGTTCGGT | 1920 |
| GGGGTCATGT | GTGTGGAGAG | CGTCAACCGG | GAGATGTCGC | CCCTGGTGGA | CAACATCGCC | 1980 |
| CTGTGGATGA | CTGAGTACCT | GAACCGGCAC | CTGCACACCT | GGATCCAGGA | TAACGGAGGC | 2040 |
| TGGGATGCCT | TTGTGGAACT | GTACGGCCCC | AGCATGCGGC | CTCTGTTTGA | TTTCTCCTGG | 2100 |
| CTGTCTCTGA | AGACTCTGCT | CAGTTTGGCC | CTGGTGGGAG | CTTGCATCAC | CCTGGGTGCC | 2160 |
| TATCTGAGCC | ACAAGTGAAG | TCAACATGCC | TGCCCCAAAC | AAATATGCAA | AAGGTTCACT | 2220 |
| AAAGCAGTAG | AAATAATATG | CATTGTCAGT | GATGTACCAT | GAAACAAAGC | TGCAGGCTGT | 2280 |

| | | | | | | |
|---|---|---|---|---|---|---|
| TTAAGAAAAA | ATAACACACA | TATAAACATC | ACACACACAG | ACAGACACAC | ACACACACAA | 2340 |
| CAATTAACAG | TCTTCAGGCA | AAACGTCGAA | TCAGCTATTT | ACTGCCAAAG | GGAAATATCA | 2400 |
| TTTATTTTTT | ACATTATTAA | GAAAAAGAT | TTATTTATTT | AAGACAGTCC | CATCAAAACT | 2460 |
| CCGTCTTTGG | AAATCCGACC | ACTAATTGCC | AAACACCGCT | TCGTGTGGCT | CCACCTGGAT | 2520 |
| GTTCTGTGCC | TGTAAACATA | GATTCGCTTT | CCATGTTGTT | GGCCGGATCA | CCATCTGAAG | 2580 |
| AGCAGACGGA | TGGAAAAAGG | ACCTGATCAT | TGGGGAAGCT | GGCTTTCTGG | CTGCTGGAGG | 2640 |
| CTGGGGAGAA | GGTGTTCATT | CACTTGCATT | TCTTTGCCCT | GGGGGCGTGA | TATTAACAGA | 2700 |
| GGGAGGGTTC | CCGTGGGGGG | AAGTCCATGC | CTCCCTGGCC | TGAAGAAGAG | ACTCTTTGCA | 2760 |
| TATGACTCAC | ATGATGCATA | CCTGGTGGGA | GGAAAAGAGT | TGGGAACTTC | AGATGGACCT | 2820 |
| AGTACCCACT | GAGATTTCCA | CGCCGAAGGA | CAGCGATGGG | AAAAATGCCC | TTAAATCATA | 2880 |
| GGAAAGTATT | TTTTTAAGCT | ACCAATTGTG | CCGAGAAAAG | CATTTTAGCA | ATTTATACAA | 2940 |
| TATCATCCAG | TACCTTAAAC | CCTGATTGTG | TATATTCATA | TATTTTGGAT | ACGCACCCCC | 3000 |
| CAACTCCCAA | TACTGGCTCT | GTCTGAGTAA | GAAACAGAAT | CCTCTGGAAC | TTGAGGAAGT | 3060 |
| GAACATTTCG | GTGACTTCCG | ATCAGGAAGG | CTAGAGTTAC | CCAGAGCATC | AGGCCGCCAC | 3120 |
| AAGTGCCTGC | TTTTAGGAGA | CCGAAGTCCG | CAGAACCTAC | CTGTGTCCCA | GCTTGGAGGC | 3180 |
| CTGGTCCTGG | AACTGAGCCG | GGCCCTCACT | GGCCTCCTCC | AGGGATGATC | AACAGGGTAG | 3240 |
| TGTGGTCTCC | GAATGTCTGG | AAGCTGATGG | ATGGAGCTCA | GAATTCCACT | GTCAAGAAAG | 3300 |
| AGCAGTAGAG | GGGTGTGGCT | GGGCCTGTCA | CCCTGGGGCC | CTCCAGGTAG | GCCCGTTTTC | 3360 |
| ACGTGGAGCA | TAGGAGCCAC | GACCCTTCTT | AAGACATGTA | TCACTGTAGA | GGGAAGGAAC | 3420 |
| AGAGGCCCTG | GGCCTTCCTA | TCAGAAGGAC | ATGGTGAAGG | CTGGGAACGT | GAGGAGAGGC | 3480 |
| AATGGCCACG | GCCCATTTTG | GCTGTAGCAC | ATGGCACGTT | GGCTGTGTGG | CCTTGGCCAC | 3540 |
| CTGTGAGTTT | AAAGCAAGGC | TTTAAATGAC | TTTGGAGAGG | GTCACAAATC | CTAAAAGAAG | 3600 |
| CATTGAAGTG | AGGTGTCATG | GATTAATTGA | CCCCTGTCTA | TGGAATTACA | TGTAAAACAT | 3660 |
| TATCTTGTCA | CTGTAGTTTG | GTTTTATTTG | AAAACCTGAC | AAAAAAAAG | TTCCAGGTGT | 3720 |
| GGAATATGGG | GGTTATCTGT | ACATCCTGGG | GCATTAAAAA | AAAATCAATG | GTGGGGAACT | 3780 |
| ATAAAGAAGT | AACAAAGAA | GTGACATCTT | CAGCAAATAA | ACTAGGAAAT | TTTTTTTCT | 3840 |
| TCCAGTTTAG | AATCAGCCTT | GAAACATTGA | TGGAATAACT | CTGTGGCATT | ATTGCATTAT | 3900 |
| ATACCATTTA | TCTGTATTAA | CTTTGGAATG | TACTCTGTTC | AATGTTAAT | GCTGTGGTTG | 3960 |
| ATATTTCGAA | AGCTGCTTTA | AAAAAATACA | TGCATCTCAG | CGTTTTTTG | TTTTAATTG | 4020 |
| TATTTAGTTA | TGGCCTATAC | ACTATTTGTG | AGCAAGGTG | ATCGTTTCT | GTTTGAGATT | 4080 |
| TTTATCTCTT | GATTCTTCAA | AAGCATTCTG | AGAAGGTGAG | ATAAGCCCTG | AGTCTCAGCT | 4140 |
| ACCTAAGAAA | AACCTGGATG | TCACTGGCCA | CTGAGGAGCT | TTGTTTCAAC | CAAGTCATGT | 4200 |
| GCATTTCCAC | GTCAACAGAA | TTGTTTATTG | TGACAGTTAT | ATCTGTTGTC | CCTTTGACCT | 4260 |
| TGTTTCTTGA | AGGTTTCCTC | GTCCCTGGGC | AATTCCGCAT | TTAATTCATG | GTATTCAGGA | 4320 |
| TTACATGCAT | GTTTGGTTAA | ACCCATGAGA | TTCATTCAGT | TAAAAATCCA | GATGGCGAAT | 4380 |
| GACCAGCAGA | TTCAAATCTA | TGGTGGTTTG | ACCTTTAGAG | AGTTGCTTTA | CGTGGCCTGT | 4440 |
| TTCAACACAG | ACCCACCCAG | AGCCCTCCTG | CCCTCCTTCC | GCGGGGCTT | TCTCATGGCT | 4500 |
| GTCCTTCAGG | GTCTTCCTGA | AATGCAGTGG | TCGTTACGCT | CCACCAAGAA | AGCAGGAAAC | 4560 |
| CTGTGGTATG | AAGCCAGACC | TCCCCGGCGG | GCCTCAGGGA | ACAGAATGAT | CAGACCTTTG | 4620 |
| AATGATTCTA | ATTTTTAAGC | AAAATATTAT | TTATGAAAG | GTTACATTG | TCAAAGTGAT | 4680 |

-continued

| | | | | | |
|---|---|---|---|---|---|
| GAATATGGAA | TATCCAATCC | TGTGCTGCTA | TCCTGCCAAA | ATCATTTTAA | TGGAGTCAGT | 4740 |
| TTGCAGTATG | CTCCACGTGG | TAAGATCCTC | CAAGCTGCTT | TAGAAGTAAC | AATGAAGAAC | 4800 |
| GTGGACGTTT | TTAATATAAA | GCCTGTTTTG | TCTTTTGTTG | TTGTTCAAAC | GGGATTCACA | 4860 |
| GAGTATTTGA | AAAATGTATA | TATATTAAGA | GGTCACGGGG | GCTAATTGCT | AGCTGGCTGC | 4920 |
| CTTTTGCTGT | GGGGTTTTGT | TACCTGGTTT | TAATAACAGT | AAATGTGCCC | AGCCTCTTGG | 4980 |
| CCCCAGAACT | GTACAGTATT | GTGGCTGCAC | TTGCTCTAAG | AGTAGTTGAT | GTTGCATTTT | 5040 |
| CCTTATTGTT | AAAAACATGT | TAGAAGCAAT | GAATGTATAT | AAAAGC | | 5086 |

( 2 ) INFORMATION FOR SEQ ID NO:20:

( i ) SEQUENCE CHARACTERISTICS:
( A ) LENGTH: 717 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..717

( x i ) SEQUENCE DESCRIPTION: SEQ ID NO:20:

| | | | | | | | | | | | | | | | | |
|---|---|---|---|---|---|---|---|---|---|---|---|---|---|---|---|---|
| ATG | GCG | CAC | GCT | GGG | AGA | ACG | GGG | TAC | GAC | AAC | CGG | GAG | ATA | GTG | ATG | 48 |
| Met | Ala | His | Ala | Gly | Arg | Thr | Gly | Tyr | Asp | Asn | Arg | Glu | Ile | Val | Met | |
| 1 | | | | 5 | | | | | 10 | | | | | 15 | | |
| AAG | TAC | ATC | CAT | TAT | AAG | CTG | TCG | CAG | AGG | GGC | TAC | GAG | TGG | GAT | GCG | 96 |
| Lys | Tyr | Ile | His | Tyr | Lys | Leu | Ser | Gln | Arg | Gly | Tyr | Glu | Trp | Asp | Ala | |
| | | | 20 | | | | | 25 | | | | | 30 | | | |
| GGA | GAT | GTG | GGC | GCC | GCG | CCC | CCG | GGG | GCC | GCC | CCC | GCA | CCG | GGC | ATC | 144 |
| Gly | Asp | Val | Gly | Ala | Ala | Pro | Pro | Gly | Ala | Ala | Pro | Ala | Pro | Gly | Ile | |
| | | | 35 | | | | | 40 | | | | | 45 | | | |
| TTC | TCC | TCC | CAG | CCC | GGG | CAC | ACG | CCC | CAT | CCA | GCC | GCA | TCC | CGC | GAC | 192 |
| Phe | Ser | Ser | Gln | Pro | Gly | His | Thr | Pro | His | Pro | Ala | Ala | Ser | Arg | Asp | |
| | | 50 | | | | | 55 | | | | | 60 | | | | |
| CCG | GTC | GCC | AGG | ACC | TCG | CCG | CTG | CAG | ACC | CCG | GCT | GCC | CCC | GGC | GCC | 240 |
| Pro | Val | Ala | Arg | Thr | Ser | Pro | Leu | Gln | Thr | Pro | Ala | Ala | Pro | Gly | Ala | |
| 65 | | | | | 70 | | | | | 75 | | | | | 80 | |
| GCC | GCG | GGG | CCT | GCG | CTC | AGC | CCG | GTG | CCA | CCT | GTG | GTC | CAC | CTG | GCC | 288 |
| Ala | Ala | Gly | Pro | Ala | Leu | Ser | Pro | Val | Pro | Pro | Val | Val | His | Leu | Ala | |
| | | | | 85 | | | | | 90 | | | | | 95 | | |
| CTC | CGC | CAA | GCC | GGC | GAC | GAC | TTC | TCC | CGC | CGC | TAC | CGC | GGC | GAC | TTC | 336 |
| Leu | Arg | Gln | Ala | Gly | Asp | Asp | Phe | Ser | Arg | Arg | Tyr | Arg | Gly | Asp | Phe | |
| | | | 100 | | | | | 105 | | | | | 110 | | | |
| GCC | GAG | ATG | TCC | AGC | CAG | CTG | CAC | CTG | ACG | CCC | TTC | ACC | GCG | CGG | GGA | 384 |
| Ala | Glu | Met | Ser | Ser | Gln | Leu | His | Leu | Thr | Pro | Phe | Thr | Ala | Arg | Gly | |
| | | 115 | | | | | 120 | | | | | 125 | | | | |
| CGC | TTT | GCC | ACG | GTG | GTG | GAG | GAG | CTC | TTC | AGG | GAC | GGG | GTG | AAC | TGG | 432 |
| Arg | Phe | Ala | Thr | Val | Val | Glu | Glu | Leu | Phe | Arg | Asp | Gly | Val | Asn | Trp | |
| | 130 | | | | | 135 | | | | | 140 | | | | | |
| GGG | AGG | ATT | GTG | GCC | TTC | TTT | GAG | TTC | GGT | GGG | GTC | ATG | TGT | GTG | GAG | 480 |
| Gly | Arg | Ile | Val | Ala | Phe | Phe | Glu | Phe | Gly | Gly | Val | Met | Cys | Val | Glu | |
| 145 | | | | | 150 | | | | | 155 | | | | | 160 | |
| AGC | GTC | AAC | CGG | GAG | ATG | TCG | CCC | CTG | GTG | GAC | AAC | ATC | GCC | CTG | TGG | 528 |
| Ser | Val | Asn | Arg | Glu | Met | Ser | Pro | Leu | Val | Asp | Asn | Ile | Ala | Leu | Trp | |
| | | | | 165 | | | | | 170 | | | | | 175 | | |
| ATG | ACT | GAG | TAC | CTG | AAC | CGG | CAC | CTG | CAC | ACC | TGG | ATC | CAG | GAT | AAC | 576 |
| Met | Thr | Glu | Tyr | Leu | Asn | Arg | His | Leu | His | Thr | Trp | Ile | Gln | Asp | Asn | |
| | | | 180 | | | | | 185 | | | | | 190 | | | |
| GGA | GGC | TGG | GAT | GCC | TTT | GTG | GAA | CTG | TAC | GGC | CCC | AGC | ATG | CGG | CCT | 624 |

| | | | | | | | | | | | | | | |
|---|---|---|---|---|---|---|---|---|---|---|---|---|---|---|
| Gly | Gly | Trp | Asp | Ala | Phe | Val | Glu | Leu | Tyr | Gly | Pro | Ser | Met | Arg | Pro |
| | | 195 | | | | 200 | | | | | | 205 | | | |

| | | | | | | | | | | | | | | | |
|---|---|---|---|---|---|---|---|---|---|---|---|---|---|---|---|
| CTG | TTT | GAT | TTC | TCC | TGG | CTG | TCT | CTG | AAG | ACT | CTG | CTC | AGT | TTG | GCC | 672 |
| Leu | Phe | Asp | Phe | Ser | Trp | Leu | Ser | Leu | Lys | Thr | Leu | Leu | Ser | Leu | Ala |
| | 210 | | | | | 215 | | | | | 220 | | | | |

| | | | | | | | | | | | | | |
|---|---|---|---|---|---|---|---|---|---|---|---|---|---|
| CTG | GTG | GGA | GCT | TGC | ATC | ACC | CTG | GGT | GCC | TAT | CTG | AGC | CAC | AAG | 717 |
| Leu | Val | Gly | Ala | Cys | Ile | Thr | Leu | Gly | Ala | Tyr | Leu | Ser | His | Lys |
| 225 | | | | | 230 | | | | | 235 | | | | |

( 2 ) INFORMATION FOR SEQ ID NO:21:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Ala | His | Ala | Gly | Arg | Thr | Gly | Tyr | Asp | Asn | Arg | Glu | Ile | Val | Met |
| 1 | | | | 5 | | | | | 10 | | | | | 15 | |
| Lys | Tyr | Ile | His | Tyr | Lys | Leu | Ser | Gln | Arg | Gly | Tyr | Glu | Trp | Asp | Ala |
| | | | 20 | | | | | 25 | | | | | 30 | | |
| Gly | Asp | Val | Gly | Ala | Ala | Pro | Gly | Ala | Ala | Pro | Ala | Pro | Gly | Ile |
| | | 35 | | | | 40 | | | | 45 | | | | |
| Phe | Ser | Ser | Gln | Pro | Gly | His | Thr | Pro | His | Pro | Ala | Ala | Ser | Arg | Asp |
| | 50 | | | | | 55 | | | | | 60 | | | | |
| Pro | Val | Ala | Arg | Thr | Ser | Pro | Leu | Gln | Thr | Pro | Ala | Ala | Pro | Gly | Ala |
| 65 | | | | | 70 | | | | | 75 | | | | | 80 |
| Ala | Ala | Gly | Pro | Ala | Leu | Ser | Pro | Val | Pro | Pro | Val | Val | His | Leu | Ala |
| | | | | 85 | | | | | 90 | | | | | 95 | |
| Leu | Arg | Gln | Ala | Gly | Asp | Asp | Phe | Ser | Arg | Arg | Tyr | Arg | Gly | Asp | Phe |
| | | | | 100 | | | | | 105 | | | | | 110 | |
| Ala | Glu | Met | Ser | Ser | Gln | Leu | His | Leu | Thr | Pro | Phe | Thr | Ala | Arg | Gly |
| | | | 115 | | | | | 120 | | | | | 125 | | |
| Arg | Phe | Ala | Thr | Val | Val | Glu | Glu | Leu | Phe | Arg | Asp | Gly | Val | Asn | Trp |
| | | 130 | | | | | 135 | | | | | 140 | | | |
| Gly | Arg | Ile | Val | Ala | Phe | Phe | Glu | Phe | Gly | Gly | Val | Met | Cys | Val | Glu |
| 145 | | | | | 150 | | | | | 155 | | | | | 160 |
| Ser | Val | Asn | Arg | Glu | Met | Ser | Pro | Leu | Val | Asp | Asn | Ile | Ala | Leu | Trp |
| | | | | 165 | | | | | 170 | | | | | 175 | |
| Met | Thr | Glu | Tyr | Leu | Asn | Arg | His | Leu | His | Thr | Trp | Ile | Gln | Asp | Asn |
| | | | 180 | | | | | 185 | | | | | 190 | | |
| Gly | Gly | Trp | Asp | Ala | Phe | Val | Glu | Leu | Tyr | Gly | Pro | Ser | Met | Arg | Pro |
| | | 195 | | | | | 200 | | | | | 205 | | | |
| Leu | Phe | Asp | Phe | Ser | Trp | Leu | Ser | Leu | Lys | Thr | Leu | Leu | Ser | Leu | Ala |
| | 210 | | | | | 215 | | | | | 220 | | | | |
| Leu | Val | Gly | Ala | Cys | Ile | Thr | Leu | Gly | Ala | Tyr | Leu | Ser | His | Lys |
| 225 | | | | | 230 | | | | | 235 | | | | | |

( 2 ) INFORMATION FOR SEQ ID NO:22:

( i ) SEQUENCE CHARACTERISTICS:
        ( A ) LENGTH: 615 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

( A ) NAME/KEY: CDS
( B ) LOCATION: 1..615

( x i ) SEQUENCE DESCRIPTION: SEQ ID NO:22:

| ATG | GCG | CAC | GCT | GGG | AGA | ACG | GGG | TAC | GAC | AAC | CGG | GAG | ATA | GTG | ATG | 48 |
| Met | Ala | His | Ala | Gly | Arg | Thr | Gly | Tyr | Asp | Asn | Arg | Glu | Ile | Val | Met | |
| 1 | | | | 5 | | | | | 10 | | | | | 15 | | |

| AAG | TAC | ATC | CAT | TAT | AAG | CTG | TCG | CAG | AGG | GGC | TAC | GAG | TGG | GAT | GCG | 96 |
| Lys | Tyr | Ile | His | Tyr | Lys | Leu | Ser | Gln | Arg | Gly | Tyr | Glu | Trp | Asp | Ala | |
| | | | | 20 | | | | | 25 | | | | | 30 | | |

| GGA | GAT | GTG | GGC | GCC | GCG | CCC | CCG | GGG | GCC | GCC | CCC | GCA | CCG | GGC | ATC | 144 |
| Gly | Asp | Val | Gly | Ala | Ala | Pro | Pro | Gly | Ala | Ala | Pro | Ala | Pro | Gly | Ile | |
| | | | 35 | | | | | 40 | | | | | 45 | | | |

| TTC | TCC | TCC | CAG | CCC | GGG | CAC | ACG | CCC | CAT | CCA | GCC | GCA | TCC | CGC | GAC | 192 |
| Phe | Ser | Ser | Gln | Pro | Gly | His | Thr | Pro | His | Pro | Ala | Ala | Ser | Arg | Asp | |
| | | 50 | | | | | 55 | | | | | 60 | | | | |

| CCG | GTC | GCC | AGG | ACC | TCG | CCG | CTG | CAG | ACC | CCG | GCT | GCC | CCC | GGC | GCC | 240 |
| Pro | Val | Ala | Arg | Thr | Ser | Pro | Leu | Gln | Thr | Pro | Ala | Ala | Pro | Gly | Ala | |
| 65 | | | | | 70 | | | | | 75 | | | | | 80 | |

| GCC | GCG | GGG | CCT | GCG | CTC | AGC | CCG | GTG | CCA | CCT | GTG | GTC | CAC | CTG | GCC | 288 |
| Ala | Ala | Gly | Pro | Ala | Leu | Ser | Pro | Val | Pro | Pro | Val | Val | His | Leu | Ala | |
| | | | | 85 | | | | | 90 | | | | | 95 | | |

| CTC | CGC | CAA | GCC | GGC | GAC | GAC | TTC | TCC | CGC | CGC | TAC | CGC | GGC | GAC | TTC | 336 |
| Leu | Arg | Gln | Ala | Gly | Asp | Asp | Phe | Ser | Arg | Arg | Tyr | Arg | Gly | Asp | Phe | |
| | | | 100 | | | | | 105 | | | | | 110 | | | |

| GCC | GAG | ATG | TCC | AGC | CAG | CTG | CAC | CTG | ACG | CCC | TTC | ACC | GCG | CGG | GGA | 384 |
| Ala | Glu | Met | Ser | Ser | Gln | Leu | His | Leu | Thr | Pro | Phe | Thr | Ala | Arg | Gly | |
| | | | 115 | | | | | 120 | | | | | 125 | | | |

| CGC | TTT | GCC | ACG | GTG | GTG | GAG | GAG | CTC | TTC | AGG | GAC | GGG | GTG | AAC | TGG | 432 |
| Arg | Phe | Ala | Thr | Val | Val | Glu | Glu | Leu | Phe | Arg | Asp | Gly | Val | Asn | Trp | |
| | 130 | | | | | 135 | | | | | 140 | | | | | |

| GGG | AGG | ATT | GTG | GCC | TTC | TTT | GAG | TTC | GGT | GGG | GTC | ATG | TGT | GTG | GAG | 480 |
| Gly | Arg | Ile | Val | Ala | Phe | Phe | Glu | Phe | Gly | Gly | Val | Met | Cys | Val | Glu | |
| 145 | | | | | 150 | | | | | 155 | | | | | 160 | |

| AGC | GTC | AAC | CGG | GAG | ATG | TCG | CCC | CTG | GTG | GAC | AAC | ATC | GCC | CTG | TGG | 528 |
| Ser | Val | Asn | Arg | Glu | Met | Ser | Pro | Leu | Val | Asp | Asn | Ile | Ala | Leu | Trp | |
| | | | | 165 | | | | | 170 | | | | | 175 | | |

| ATG | ACT | GAG | TAC | CTG | AAC | CGG | CAC | CTG | CAC | ACC | TGG | ATC | CAG | GAT | AAC | 576 |
| Met | Thr | Glu | Tyr | Leu | Asn | Arg | His | Leu | His | Thr | Trp | Ile | Gln | Asp | Asn | |
| | | | 180 | | | | | 185 | | | | | 190 | | | |

| GGA | GGC | TGG | GTA | GGT | GCA | TCT | GGT | GAT | GTG | AGT | CTG | GGC | | | | 615 |
| Gly | Gly | Trp | Val | Gly | Ala | Ser | Gly | Asp | Val | Ser | Leu | Gly | | | | |
| | | | 195 | | | | | 200 | | | | 205 | | | | |

( 2 ) INFORMATION FOR SEQ ID NO:23:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| Met | Ala | His | Ala | Gly | Arg | Thr | Gly | Tyr | Asp | Asn | Arg | Glu | Ile | Val | Met |
| 1 | | | | 5 | | | | | 10 | | | | | 15 | |

| Lys | Tyr | Ile | His | Tyr | Lys | Leu | Ser | Gln | Arg | Gly | Tyr | Glu | Trp | Asp | Ala |
| | | | | 20 | | | | | 25 | | | | | 30 | |

| Gly | Asp | Val | Gly | Ala | Ala | Pro | Pro | Gly | Ala | Ala | Pro | Ala | Pro | Gly | Ile |
| | | | 35 | | | | | 40 | | | | | 45 | | |

| Phe | Ser | Ser | Gln | Pro | Gly | His | Thr | Pro | His | Pro | Ala | Ala | Ser | Arg | Asp |
| | | 50 | | | | | 55 | | | | | 60 | | | |

| Pro 65 | Val | Ala | Arg | Thr | Ser 70 | Pro | Leu | Gln | Thr 75 | Pro | Ala | Ala | Pro | Gly | Ala 80 |

| Ala | Ala | Gly | Pro | Ala 85 | Leu | Ser | Pro | Val 90 | Pro | Val | Val | His | Leu 95 | Ala |

| Leu | Arg | Gln | Ala 100 | Gly | Asp | Asp | Phe | Ser 105 | Arg | Arg | Tyr | Arg | Gly 110 | Asp | Phe |

| Ala | Glu | Met 115 | Ser | Ser | Gln | Leu | His 120 | Leu | Thr | Pro | Phe | Thr 125 | Ala | Arg | Gly |

| Arg | Phe 130 | Ala | Thr | Val | Val | Glu 135 | Glu | Leu | Phe | Arg | Asp 140 | Gly | Val | Asn | Trp |

| Gly 145 | Arg | Ile | Val | Ala | Phe 150 | Phe | Glu | Phe | Gly | Val 155 | Met | Cys | Val | Glu 160 |

| Ser | Val | Asn | Arg | Glu 165 | Met | Ser | Pro | Leu | Val 170 | Asp | Asn | Ile | Ala | Leu 175 | Trp |

| Met | Thr | Glu | Tyr 180 | Leu | Asn | Arg | His | Leu 185 | His | Thr | Trp | Ile | Gln 190 | Asp | Asn |

| Gly | Gly | Trp 195 | Val | Gly | Ala | Ser | Gly 200 | Asp | Val | Ser | Leu | Gly 205 |

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA ( i v ) ANTI-SENSE: YES ( i x ) FEATURE:
        ( A ) NAME/KEY: Modified_base
        ( B ) LOCATION: 16..17
        ( D ) OTHER INFORMATION: Last two internucleoside linkages are
            phosphorothioates ( x i ) SEQUENCE DESCRIPTION: SEQ ID NO:24:

TCTCCCAGCG TGCGCCAT                                                18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA ( i v ) ANTI-SENSE: NO ( i x ) FEATURE:
        ( A ) NAME/KEY: Modified_base
        ( B ) LOCATION: 16..17
        ( D ) OTHER INFORMATION: Last two internucleoside linkages are
            phosphorothioates ( x i ) SEQUENCE DESCRIPTION: SEQ ID NO:25:

TGCACTCACG CTCGGCCT                                                18

( 2 ) INFORMATION FOR SEQ ID NO:26:

( i ) SEQUENCE CHARACTERISTICS:

(A) LENGTH: 20 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA (i v) ANTI-SENSE: YES (i x) FEATURE:
(A) NAME/KEY: Modified_base
(B) LOCATION: 18..19
(D) OTHER INFORMATION: Last two internucleoside linkages are phosphorothioates (x i) SEQUENCE DESCRIPTION: SEQ ID NO:26:

GCGCGGCGGG CGGGCGGGCA 20

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA (i v) ANTI-SENSE: NO (i x) FEATURE:
(A) NAME/KEY: Modified_base
(B) LOCATION: 18..19
(D) OTHER INFORMATION: Last two internucleoside linkages are phosphorothioates (x i) SEQUENCE DESCRIPTION: SEQ ID NO:27:

GGGCGGAGGC CGGCCGGCGG 20

(2) INFORMATION FOR SEQ ID NO:28:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA (i v) ANTI-SENSE: YES (i x) FEATURE:
(A) NAME/KEY: Modified_base
(B) LOCATION: 18..19
(D) OTHER INFORMATION: Last two internucleoside linkages are phosphorothioates (x i) SEQUENCE DESCRIPTION: SEQ ID NO:28:

AGCGGCGGCG GCGGCAGCGC 20

(2) INFORMATION FOR SEQ ID NO:29:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Other nucleic acid;
(A) DESCRIPTION: Synthetic DNA -continued

```
( i v ) ANTI-SENSE: NO ( i x ) FEATURE:
    ( A ) NAME/KEY: Modified_base
    ( B ) LOCATION: 18..19
    ( D ) OTHER INFORMATION: Last two internucleoside linkages are
          phosphorothioates ( x i ) SEQUENCE DESCRIPTION: SEQ ID NO:29:

GGGCCGGGAA GGGCGCCCGC                                                                  20
```

REGULATION OF BCL-2 GENE EXPRESSION

RELATED APPLICATION DATA

This application is a continuation of U.S. application Ser. No. 08/124,256, filed Sep. 20, 1993, now abandoned, which is a continuation-in-part of U.S. application Ser. No. 07/840,716, filed Feb. 21, 1992, now abandoned, which is a continuation-in-part of U.S. application Ser. No. 07/288,692, filed Dec. 22, 1988, now abandoned.

REFERENCE TO GOVERNMENT GRANTS

The research in this patent application was supported in part by National Institutes of Health grant CA 47951 and CA 60381. The United States government has certain rights in the invention.

FIELD OF THE INVENTION

The present invention relates to the field of treatments for cancer and more particularly to the field of anticode oligomer treatments for cancer.

BACKGROUND OF THE INVENTION

Current approaches to cancer treatment suffer from a lack of specificity. The majority of drugs that have been developed are natural products or derivatives that either block enzyme pathways or randomly interact with DNA. Due to low therapeutic indices, most cancer treatment drugs are accompanied by serious dose-limiting toxicities. The administration of drugs to treat cancer kills not only cancer cells but also normal non-cancerous cells. Because of these deleterious effects, treatments that are more specific for cancerous cells are needed.

It has been found that a class of genes, the oncogenes, plays a large role in the transformation and maintenance of the cancerous state and that turning off these genes, or otherwise inhibiting their effects, can return a cell to a normal phenotype. The role of oncogenes in the etiology of many human cancers has been reviewed in Bishop, "Cellular Oncogenes and Retroviruses," *Science*, 235:305–311 (1987). In many types of human tumors, including lymphomas and leukemias, the human bcl-2 gene is overexpressed, and may be associated with tumorigenicity (Tsujimoto et al. Involvement of the bcl-2 gene in human follicular lymphoma, *Science* 228:1440–1443 (1985)).

Antisense oligodeoxynucleotides are one example of a specific therapeutic tool with the potential for ablating oncogene function. These short (usually about 30 bases) single-stranded synthetic DNAs have a complementary base sequence to the target mRNA and form a hybrid duplex by hydrogen bonded base pairing. This hybridization can be expected to prevent expression of the target mRNA code into its protein product and thus preclude subsequent effects of the protein product. Because the mRNA sequence expressed by the gene is termed the sense sequence, the complementary sequence is termed the antisense sequence. Under some circumstances, inhibition of mRNA would be more efficient than inhibition of an enzyme's active site, since one mRNA molecule gives rise to multiple protein copies.

Synthetic oligodeoxynucleotides complementary to (antisense) mRNA of the c-myc oncogene have been used to specifically inhibit production of c-myc protein, thus arresting the growth of human leukemic cells in vitro, Holt et al., *Mol. Cell Biol.* 8:963–973 (1988), and Wickstrom et al., *Proc. Natl. Acad. Sci.* USA, 85:1028–1–32 (1988). oligodeoxynucleotides have also been employed as specific inhibitors of retroviruses, including the human immunodeficiency virus (HIV-I), Zamecnik and Stephenson, *Proc. Natl. Acad. Sci.* USA, 75:280–284 (1978) and Zamecnik et al., *Proc. Natl. Acad. Sci.* USA, 83:4143–4146 (1986).

SUMMARY OF THE INVENTION

The invention provides anticode oligomers and methods for inhibiting growth of cancer cells. The growth of lymphoma or leukemia cells, which are types of lymphocytes, are inhibitied by the anticode oligomers and methods of the invention. An anticode oligomer complementary to at least an effective portion of the mRNA sense strand to the human bcl-2 gene is provided and cells are then contacted with the anticode oligomer in a concentration sufficient to inhibit growth of the cells. The methods of the invention are suitable for inhibiting growth of lymphoma/leukemia cells that express the human bcl-2 gene and have a t (14; 18) chromosomal translocation as well as those that express the bcl-2 gene but do not have a t (14; 18) chromosomal translocation.

In accordance with preferred embodiments, the anticode oligomer is substantially complementary to a strategic site in the pre-mRNA sense strand or substantially complementary to the mRNA. A preferred strategic site is the translation-initiation site of the pre-mRNA coding strand. Alternative strategic sites include coding sites for splicing, transport or degradation. The subject anticode oligomer either in its "native," unmodified form—oligonucleotide—or as a derivative, is brought into contact with the target lymphoma or leukemia cells. For in vivo therapeutic use, a derivative of the "native" oligonucleotide, such as the phosphorothioate form is preferable since it is believed that these forms are more resistant to degradation, notwithstanding the fact that response times to some analogues, such as the phosphorothioate analogs, has been found to be somewhat slower than to the "native" form of the oligonucleotide.

A preferred anticode oligomer, denominated herein the TI-AS (translation initiation anticode oligomer) is an oligodeoxynucleotide which straddles the translation-initiation site of the mRNA coding strand of the human bcl-2 gene and is complementary to this region. More preferably, this nucleotide comprises a TAC portion which is complementary to the ATG initiation sequence of the coding strand for the bcl-2 gene, and preferably further comprises flanking portions of two to about one hundred bases, more preferably from about five to about twenty bases, which are complementary to portions of the bcl-2 gene coding strand flanking said initiation sequence. The TI-AS nucleotide has been found effective at inhibiting the growth of the target cells both in the presence and absence of serum.

Alternatively, the anticode oligomer comprises an antisense nucleotide complementary to at least an effective portion of the splice donor site of the pre-mRNA coding strand for the human bcl-2 gene. More particularly, this nucleotide comprises a CA portion which is complementary to the GT splice donor of the bcl-2, and again comprises flanking portions of two to about one hundred bases, preferably from about five to about twenty bases, which are complementary to portions of the bcl-2 gene coding strand flanking said splice donor.

In yet another embodiment, the anticode oligomer is complementary to at least an effective portion of the splice acceptor region of the pre-mRNA coding strand for the human bcl-2 gene. This oligomer comprises at least a TC portion which is complementary to the AG splice acceptor of the bcl-2 gene, and again comprises flanking portions of two to about one hundred, preferably from about five to about twenty bases which are complementary to portions of the bcl-2 gene coding strand flanking said acceptor. The subject oligomer may also be selected to overlap the coding site for the 26 kDa protein, bcl-2-alpha or for the 22 kDa protein, bcl-2-beta, protein products of the bcl-2 gene. Preferably the oligomer is selected to minimize homology with anticode oligomers for pre-mRNA or mRNA coding strands for other gene sequences.

Accordingly, a primary object of the present invention is the provision of novel anticode oligomers, which are useful in inhibiting the growth of cancer cells. The present invention also includes compositions for inhibiting the growth of tumor cells, which compositions comprise the anticode oligomer of the present invention together with a pharmaceutically acceptable carrier.

A further object of the present invention is the provision of methods for inhibiting the growth of cancer cells using said anticode oligomers. As a feature of the present invention, it was discovered that average reductions of 30–40% in the relative levels of bcl-2 protein markedly enhanced the sensitivity of lymphoma cells, in particular, t(14;18)-containing lymphoma cell lines to cancer chemotherapeutic agents, including conventional anticancer drugs. Such reductions were achieved by introducing into tumor cells an anticode oligomer which binds to either pre-mRNA or mRNA expressed from the bcl-2 gene. Two methods were used in the present invention to introduce said anticode oligomers to tumor cells. One method involved contacting the tumor cells with a composition comprising the anticode oligomers. Another method involved transfecting the tumor cells with a vector encoding an antisense oligonucleotide. Introducing an anticode oligomer to tumor cells achieved a reduction of bcl-2 expression and increases the chemosensitivity of neoplastic cells to cancer chemotherapeutic agents or anticancer drugs.

Accordingly, the present invention achieved a method of killing tumor cells by introducing to tumor cells anticode oligomers which reduce bcl-2 gene expression or impair Bcl-2 protein function before contacting the cells with cancer chemotherapeutic agents. The cancer chemotherapeutic agents reduced the numbers of viable malignant cells, and the portion of tumor cells killed was greater than the portion which would have been killed by the same amount of drug in the absence of introducing the anticode oligomer oligodeoxynucleotide to the cells.

These and other objects of the present invention will become apparent from the following detailed description.

BRIEF DESCRIPTION OF THE DRAWINGS

FIG. 4A shows the effect of oligonucleotides targeted against the translation initiation site. FIG. 4B shows the effect of oligonucleotides directed against the 5'-cap region of bcl-2 mRNA.

FIG. 6A shows results from 697 cells cultured for 2 days (PO). FIG. 6B shows results from 697 cells cultured for 4 days (PS). The black columns show the results with a sense oligonucleotide, and the hatched columns with an antisense oligonucleotide TI-AS.

FIG. 7 shows FACS profiles for 697 cells before and after treatment with bcl-2 antisense oligonucleotides.

FIGS. 8A–8C shows bcl-2 antisense oligodeoxynucleotides producing sequence-specific reductions in bcl-2 mRNA and bcl-2 protein and producing increased sensitivity of SU-DHL-4 cells to cancer chemotherapeutic drugs. FIG. 8A is a semi-quantitative reverse transcriptase polymerase chain reaction (RT-PCR) assay. AS stands for antisense and SC stands for an oligonucleotide wherein the bases are in scrambled order. FIG. 8B shows results from a quantitative immunoblot assay, wherein the data is expressed as a percentage relative to cells treated with control SC oligomers. SU-DHL-4 cells were cultured with pairs of either PS (squares) or PO/PS (circles) AS and SC oligomers for 3 days. The inset shows immunoblot results for p26-Bcl-2 and a p75 cross-reactive (CR) band. FIG. 8C shows results where $10^{-4}$ M Ara-C, MTX, or DEX was added 1 day after addition of PS (squares) or PO/PS (circles) oligomers to cultures of SU-DHL-4 cells, and MTT assays were performed on day 3. Data are presented as a % control relative to cells cultured with drugs in the absence of any oligomers.

FIGS. 10A–10B show reduction of chemoresistance of RS11846 cells from inducible bcl-2 antisense expression from an expression plasmid.

DETAILED DESCRIPTION OF THE INVENTION

Figure 1A:
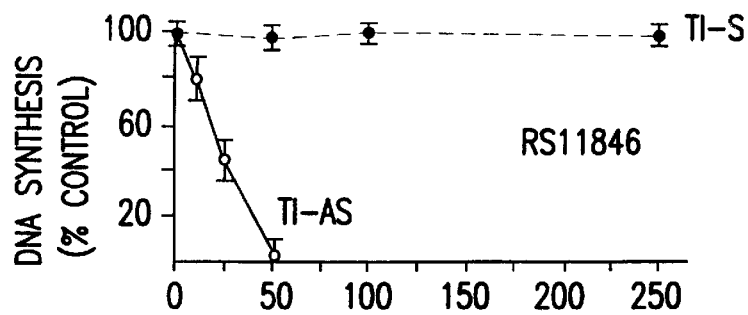
FIG. 1 shows graphs of the effects of varying concentrations of antisense oligodeoxynucleotides on inhibition of cell proliferation.
Figure 1B:
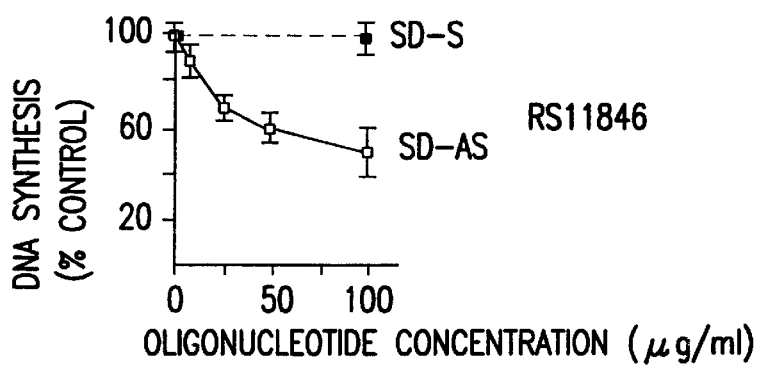
Figure 1C:
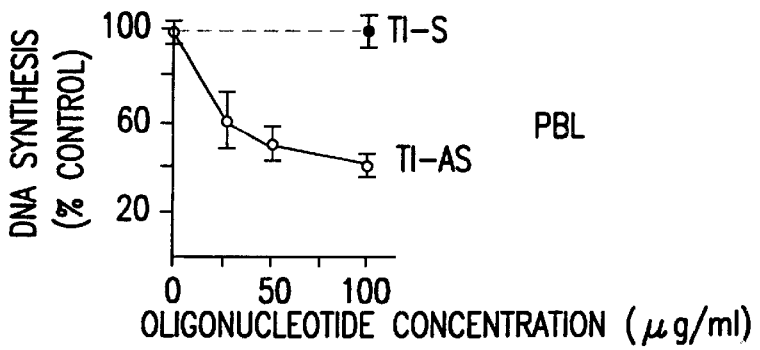
Figure 1D:
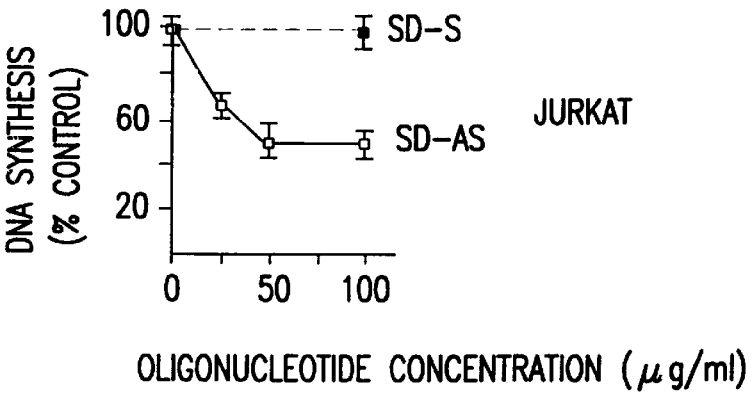

According to the invention, anticode oligomers are provided for inhibiting cancer cell growth, for increasing the sensitivity of cancer cells to cancer chemotherapeutic agents, or for inducing cancer cell death alone or in combination with any one or more cancer chemotherapeutic agents.

Definitions

As used herein, the term "anticode oligomers" means anticode oligonucleotides and analogs thereof and refers to a range of chemical species that recognize polynucleotide target sequences through hydrogen bonding interactions with the nucleotide bases of the target sequences. The target sequences may be single- or double-stranded RNA or single- or double-stranded DNA.

The anticode oligonucleotides and analogs thereof may be RNA or DNA, or analogs of RNA or DNA, commonly referred to as antisense oligomers or antisense oligonucleotides. Such RNA or DNA analogs comprise but are not limited to 2-O'-alkyl sugar modifications, methylphosphonate, phosphorodithioate, phosphordithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified, or replaced by another suitable moiety, resulting in polymers which include, but are not limited to, morpholino analogs and peptide nucleic acid (PNA) analogs (Egholm, et al. Peptide Nucleic Acids (PNA)—oligonucleotide Analogues with an Achiral Peptide Backbone, (1992)).

Anticode analogs may also be mixtures of any of the oligonucleotide analog types together or in combination with native DNA or RNA. At the same time, the oligonucleotides and analogs thereof may be used alone or in combination with one or more additional oligonucleotides or analogs thereof. The oligonucleotides may be from about 10 to about 1,000 nucleotides long. Although oliognucleotides of 10 to 100 nucleotides are useful in the invention, preferred oligonucleotides range from about 15 to about 24 bases in length.

Anticode oligonucleotides and analogs thereof also comprise conjugates of the oligonucleotides and analogs thereof. (John Goodchild, Congugates of oligonucleotides and Modified Oligonucleotides: A Review of Their Synthesis and Properties, *Bioconjugate Chemistry*, Volume 1 No. 3, May/June (1990)). Such conjugates having properties to improve the uptake, pharmacokinetics, and nuclease resistance of the oligonucleotide, or the ability to enhance cross-linking or cleavage of the target sequence by the oligonucleotide.

As used herein, the term "cell proliferation" refers to cell division rate/cell cycle. The term "growth," as used herein, encompasses both increased cell numbers due to faster cell division and due to slower rates of cell death.

As used herein, bcl-2 gene expression refers to bcl-2 protein production from the human bcl-2 gene; e.g. reduced bcl-2 gene expression means reduced levels of bcl-2 protein.

As used herein, "strategic sites" are defined as any site which when bound by the claimed anticode molecules or analogs thereof results in inhibiting expression of the bcl-2 gene.

As used herein, the term "sequence portion" is a portion of the nucleotide sequence of an RNA oligonucleotide. In appropriate contexts, "sequence portion" may refer to a portion of the nucleotide sequence of a DNA segment or DNA oligonucleotide.

Uncontrolled cell proliferation is a marker for a cancerous or abnormal cell type. Normal, non-cancerous cells divide regularly, at a frequency characteristic for the particular type of cell. When a cell has been transformed into a cancerous state, the cell divides and proliferates uncontrollably. Inhibition of proliferation modulates the uncontrolled division of the cell. Containment of cell division often correlates with a return to a non-cancerous state.

A human gene termed bcl-2 (B cell lymphoma/leukemia-2) is implicated in the etiology of some common lymphoid tumors, Croce et al., "Molecular Basis Of Human B and T Cell Neoplasia," in: *Advance in Viral Oncology*, 7:35–51, G. Klein (ed.), New York: Raven Press, 1987. High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in certain leukemias that do not have a t(14; 18) chromosomal translocation, including most cases of chronic lymphocytic leukemia acute, many lymphocytic leukemias of the pre-B cell type, neuroblastomas, nasophryngeal carcinomas, and many adenocarcinomas of the prostate, breast, and colon. (Reed et al., Differential expression of bcl-2 protooncogene in neuroblastoma and other human tumor cell lines of neural origin. *Cancer Res.* 51:6529 (1991); Yunis et al. Bcl-2 and other genomic alterations in the prognosis of large-cell lymphomas. *New England J. Med.* 320:1047; Campos et al. High expression of bcl-2 protein in acute myeloid leukemia is associated with poor response to chemotherapy. *Blood* 81:3091–3096 (1993); McDonnell et al. Expression of the protooncogene bcl-2 and its association with emergence of androgen-independent prostate cancer. *Cancer Res.* 52:6940–6944 (1992); Lu, Q-L, et al. Bcl-2 protooncogene expression in Epstein Barr Virus-Associated Nasopharyngeal Carcinoma, *Int. J. Cancer* 53:29–35 (1993); Bonner et al. bcl-2 protooncogene and the gastrointestinal mucosal epithelial tumor progression model as related to proposed morphologic and molecular sequences, *Lab.Invest.* 68:43A (1993)).

While not limited to the following explanation, the present invention exploits cellular mechanisms concerned with normal cell death. Because most types of cells have a finite life span and are programmed to die, uncontrollable cell accumulation can also result because of a defect in normal cell death mechanisms rather than through an increased rate of cell division. The bcl-2 gene contributes to the pathogenesis of cancer primarily by prolonging cell survival rather than accelerating cell division.

Antisense oligomers suitable for use in the invention include nucleotide oligomers which are two to two hundred nucleotide bases long; more preferably ten to forty bases long; most preferably twenty bases long. The oligonucleotides are preferably selected from those oligonucleotides complementary to strategic sites along the pre-mRNA of bcl-2, such as the translation initiation site, donor and splicing sites, or sites for transportation or degradation.

Blocking translation at such strategic sites prevents formation of a functional bcl-2 gene product. It should be appreciated, however, that any combination or subcombination of anticode oligomers, including oliognucleotides complementary or substantially complementary to the bcl-2 pre-mRNA or mRNA that inhibit cell proliferation, is suitable for use in the invention. For example, oligodeoxynucleotides complementary to sequence portions of contiguous or non-contiguous stretches of the bcl-2 RNA may inhibit cell proliferation and would thus be suitable for use in the invention.

It should also be appreciated that anticode oligomers suitable for use in the invention may also include oligonucleotides flanking those complementary or substantially complementary to such sequence portions as the strategic or other sites along the bcl-2 mRNA. The flanking sequence portions are preferably from two to about one hundred bases, more preferably from about five to about twenty bases in length. It is also preferable that the anticode oligomers be complementary to a sequence portion of the pre-mRNA or mRNA that is not commonly found in pre-mRNA or mRNA of other genes to minimize homology of anticode oligomers for pre-mRNA or mRNA coding strands from other genes.

Preferred antisense, or complementary, oligodeoxynucleotides are listed in Table I.

administration to a subject or for ex-vivo administration. Examples of suitable pharmaceutical carriers are a variety of cationic lipids, including, but not limited to N-(1(2,3-dioleyloxy)propyl)-N,N,N-trimethylammonium chloride (DOTMA) and diolesylphosphotidylethanolamine (DOPE) ]. Liposomes are also suitable carriers for the anticode oligomers of the invention.

The anticode oligomers may be administered to patients by any effective route, including intravenous, intramuscular, intrathecal, intranasal, intraperitoneal, subcutaneous

TABLE I bcl-2 Oligodeoxynucleotides translation initiation antisense (TI-AS)  3'... CCCTTCCTACCGCGTGCGAC ... 5'   SEQ ID NO:1 bcl-2       5'... CTTTTCCTCTGGGAAGGATGGCGCACGCTGGGAGA ... 3'   SEQ ID NO:2 splice donor antisense (SD-AS)  3 ... CCTCCGACCCATCCACGTAG ... 5'   (SEQ ID NO:3)

bcl-2       5'... ACGGGGTAC ... GGAGGCTGGGTAGGTGCATCTGGT ... 3'   (SEQ ID NO:4)

splice acceptor antisense (SA-AS)  3'... GTTGACGTCCTACGGAAACA ... 5'   (SEQ ID NO:5)

bcl-2       5'... CCCCCAACTGCAGGATGCCTTTGTGGAACTGTACGG ... 3'      (SEQ ID NO:6)

It will be appreciated by those skilled in the art to which this invention pertains, that anticode oligomers having a greater or lesser number of substituent nucleotides, or that extend further along the bcl-2 mRNA in either the 3' or 5' direction than the preferred embodiments, but which also inhibit cell proliferation are also within the scope of the invention.

It is preferable to use chemically modified derivatives or analogs of anticode oligomers in the performance of the invention rather than "native" or unmodified oligodeoxynucleotides. "Native" oligodeoxynucleotides can be conveniently synthesized with a DNA synthesizer using standard phosphoramidite chemistry. Suitable derivatives, and methods for preparing the derivatives, include phosphorothioate, Stein et al., *Nucl. Acids Res.*, 16:3209–3221 (1988); methylphosphonate, Blake et al., *Biochemistry* 24:6132–6138 (1985) and alphadeoxynucleotides, Morvan et al., *Nucl. Acids Res.* 14:5019–5032 (1986), 2'-O-methylribonucleosides (Monia et al. Evaluation of 2'-modified oligonucleotides containing 2' deoxy gaps as antisense inhibitors of gene expresssion. *J. Biol. Chem.* 268:14514–14522 (1933)), and covalently-linked derivatives such as acridine, Asseline et al., *Proc. Natl Acad. Sci.* USA 81:3297–3201 (1984); alkylated (e.g., N-2-chlorocethylamine), Knorre et al., *Biochemie* 67:783–789 (1985) and Vlassov et al., *Nucl. Acids Res.* 14:4065–4076 (1986); phenazine, Knorre et al., supra, and Vlassov et al., supra; 5-methyl-N⁴-N⁴-ethanocytosine, Webb et al., *Nucl. Acids Res.* 14:7661–7674 (1986); Fe-ethylenediamine tetraacetic acid (EDTA) and analogues, Boutorin et al., FEBS Letters 172:43–46 (1984); 5-glycylamido-1, 10-o-phenanthroline, Chi-Hong et al., *Proc. Natl. Acad. Sci. USA* 83:7147–7151 (1986); and diethylenetriaamine-pentaacetic acid (DTPA) derivatives, Chu et al., *Proc. Natl. Acad. Sci.* USA 82:963–967 (1985). All of the above publications are hereby specifically incorporated by reference as if fully set forth herein.

The anticode oligomer of the present invention can also be combined with a pharmaceutically acceptable carrier for injection, in situ injection and oral administration. Oral administration requires enteric coatings to protect the claimed anticode molecules and analogs thereof from degradation along the gastrointestinal tract. The anticode oligomers may be mixed with an amount of a physiologically acceptable carrier or diluent, such as a saline solution or other suitable liquid. The anticode oligomers may also be combined with liposomes or other carrier means to protect the anticode molecules or analogs thereof from degradation until they reach their targets and/or facilitate movement of the anticode molecules or analogs thereof across tissue barriers.

The anticode oligomers may also be useful for ex vivo bone marrow purging. Normally, the amounts of conventional cancer chemotherapeutic agents or drugs and irradiation that a patient can receive are limited by toxicity to the marrow, i.e., anemia (fatigue, heart failure), thrombocytopenia (bleeding), neutropenia (infection). Thus, in order to deliver sufficient concentrations of drugs and irradiation to totally eradicate the tumor, the physician would simultaneously destroy the patient's normal bone marrow cells leading to patient demise. Alternatively, large amounts of bone marrow can be surgically extracted from the patient and stored vitro. while the patient receives aggressive conventional treatment. The patient can then be rescued by reinfusion of their own bone marrow cells, but only if that marrow has been "purged" of residual malignant cells. The claimed anticode oligomers could be used to remove residual malignant cells from the bone marrow.

The anticode oligomers are administered in amounts effective to inhibit cancer or neoplastic cell growth. The actual amount of any particular anticode oligomer administered will depend on factors such as the type of cancer, the toxicity of the anticode oligomer to other cells of the body, its rate of uptake by cancer cells, and the weight and age of the individual to whom the anticode oligomer is administered. Because of inhibitors present in human serum that may interfere with the action of the anticode oligomer an effective amount of the anticode oligomer for each individual may vary. An effective dosage for the patient can be ascertained by conventional methods such as incrementally increasing the dosage of the anticode oligomer from an amount ineffective to inhibit cell proliferation to an effective amount. It is expected that concentrations presented to cancer cells in the range of about 0.001 micromolar to about 100 micromolar will be effective to inhibit cell proliferation.

The anticode oligomers are administered to the patient for at least a time sufficient to inhibit proliferation of the cancer cells. The anticode oligomers are preferably administered to patients at a frequency sufficient to maintain the level of anticode oligomers at an effective level in or around the cancer cells. To maintain an effective level, it may be necessary to administer the anticode oligomers several times a day, daily or at less frequent intervals. Anticode oligomers are administered until cancer cells can no longer be detected, or have been reduced in number such that further treatment provides no significant reduction in number, or the cells have been reduced to a number manageable by surgery or other treatments. The length of time that the anticode oligomers are administered will depend on factors such as the rate of uptake of the particular oligodeoxynucleotide by cancer cells and time needed for the cells to respond to the oligodeoxynucleotide. In vitro, maximal inhibition of neoplastic cell growth by "native," unmodified anticode oligomers occurred two days after initiation of cultures, whereas phosphorothioate oligodeoxynucleotides required 4 to 7 days to achieve maximal inhibition. In vivo, the time necessary for maximal inhibition of cell proliferation may be shorter or longer.

The anticode oligomers of the invention may be administered to patients as a combination of two or more different anticode oligomer oligodeoxynucleotide sequences or as a single type of sequence. For instance, TI-AS and SD-AS could be administered to a patient or TI-AS alone.

It is also believed that the anticode oligomers of the invention may be useful in the treatment of autoimmune diseases. Autoimmune diseases are those diseases in which the body's immune system has malfunctioned in some way. Administration of the anticode oligomers of the invention to a person having an autoimmune disease should inhibit proliferation of bcl-2 overexpressing lymphocytes, which would in turn reduce the symptoms of the autoimmune disease. For use in treating autoimmune diseases, the anticode oligomers would be administered as described herein.

EXAMPLES

General Methods

The Examples below use the following protocols:

A. Cells and Cell Cultures. Human leukemic cells lines used for these studies were RS11846 follicular lymphoma cells, 697 pre-B cell acute lymphocytic leukemic cells, and JURAT T cell acute lymphocytic leukemic cells as described in Tsujimoto et al., *Proc. Natl. Acad. Sci. USA*, 83:5214–5218 (1986) and Weiss et al., *Proc. Natl. Acad. Sci. USA*, 138:2169–2174 (1987). Human peripheral blood lymphocytes (PBL) were isolated from fresh whole blood as described in Reed et al., *J. Immunol.*, 134:314–319 (1985). All lymphoid cells were cultured at $5 \times 10^5$ cells/ml in RPMI medium supplemented with 1 mM glutamine, antibiotics, and either 5–10% (v:v) fetal bovine serum (FBS), 5–10% (v:v) calf serum (CS) (both from Hyclone Laboratories), or 1% (v:v) HLI concentrated supplement (Ventrex Laboratories) for serum-free cultures. Murine fibroblast cell lines were added at $10^3$ cells/cm$^2$ in DMEM medium containing glutamine, antibiotics and 5–10% (v:v) FCS. Fibroblast cell lines were NIH 3T3 cells, 3T3-B-alpha-S cells, and 3T3-B-alpha-AS cells. These latter two cell lines are NIH 3T3 cells that express high levels of a human bcl-2-alpha cDNA in either the sense or antisense orientation, respectively, by virtue of stable transfection with expression vectors constructs.

B. Measurement of Cellular Growth. Growth of cell lines cultured in the presence or absence of anticode oligomers was measured by two methods: cell counts using a hemocytometer; and DNA synthesis by assaying [$^3$H]-thymidine incorporation essentially as described in Reed et al., *J. Immunol.*, 134:314–319 (1985). Briefly, cells were cultured in 96-well flat-bottomed microtiter plates (Falcon) at 0.2 ml/well. At appropriate times, cells were resuspended, 25 μl removed from cultures for cell counting, and this volume replaced with 25 μl of 20 UCi/ML [$^3$H]-thymidine (specific activity 6.7 Ci/mmole) (New England Nuclear). Microtiter cultures were then returned to 37° C. and 95% air: 5% CO$_2$ atmosphere for 8 hours before lysing cells an glass filters and determining relative levels of [$^3$H]-thymidine incorporation into DNA by scintillation counting. Cell counts were performed in the presence of trypan blue dye to determine the concentration of viable cells in duplicate microcultures.

MTT [3-(4,5-dimethylthiazol-2-yl)-2,5-diphenyl tetrazolium bromide)] dye reduction assays were performed by the method of Tada, et al. J. Immunol Methods 93, 157 (1986), and confirmed to be within the linear range of the assay under the conditions described here. The number of viable cells per well was extrapolated from standard curves that were included with each assay and that consisted of serial two-fold dilutions of exponentially growing SU-DHL-4 cells in HL-1 medium, beginning with $10^6$ cells/ml (0.2 mi/well). Samples were assayed in triplicate and the OD600$_{nm}$ for a media/reagent blank was subtracted from all values prior to calculations.

C. RNA Blot Analysis. Total cellular RNA was isolated by a quanidinium isothiocyanate/phenol procedure as described in Chomczynski et al., *Analyt. Biochem.*, 162:156–139 (1987). The polyadenylated fraction was purified by oligodeoxythymidine-cellulose chromatography as described in Aviv et al., *Proc. Natl. Acad. Sci. USA*, 69:1408–1412 (1972). Approximately 5 μg aliquots of mRNA were size-fractionated in 0.8% agarose/6% formaldehyde gels and transferred to nylon membranes. Blots were prehybridized, hybridized, and washed exactly as described in Reed et al., *Mol. Cell Biol.*, 5:3361–3366 (1985), using either a $^{32}$P-cDNA for human bcl-2, as described in Tsujimoto et al., *Proc. Natl. Acad. Sci. USA*, 83:5214–5218 (1986), or a murine bcl-2 probe, pMBCL5.4 as described in Negrini et al., *Cell*, 49:455–463 (1987). Blots were exposed to Kodak XAR film with intensifying screens at −70° C. for 1–10 days. Eluting $^{32}$P-bcl-2 probes from membranes and rehybridizing with a $^{32}$P probe for mouse beta-2-microglobulin verified nearly equivalent amounts of mRNA for all samples on blots.

EXAMPLE 1

Preparation of Anticode oligomers

Normal and phosphorothioate oligodeoxynucleotides were synthesized using an Applied Biosystems 380B DNA synthesizer, and purified by HPLC reverse-phase chromatography (PRP-1 column) as described in Stein et al., *Nucl. Acids Res.*, 16:3209–3221 (1988) which is specifically incorporated as if fully set forth herein. In some cases it was necessary to further purify oligodeoxynucleotides by C18-Sep-Pak chromatography (Waters Associates, Millipore, Inc.), as described previously in Kern et al., *J. Clin. Invest.*, 81:237–244 (1988), to eliminate nonspecific cytotoxic activity. Oligodeoxynucleotides eluted in 30% acetonitrile were evaporated to dryness, resuspended at 1–2 mM in sterile Dulbecco's phosphate-buffered saline or Hanks' buffered salt solution (both from Gibco), and stored at −80° C. in small aliquots.

Table I shows the oligodeoxynucleotides synthesized and their relation to the sense-strand of the human bcl-2 gene. Portions of the sequence of the coding strand of the human bcl-2 gene are shown, including the translation initiation site (top), splice donor site (middle), splice acceptor region (bottom), and emperically selected sites within the 5' untranslated portion of bcl-2 pre-mRNA. The ATG initiation codon, GT splice donor, and AG splice acceptor consensus sequences are in boxes.

The sequences of the oligodeoxynucleotides synthesized for these investigations are presented, and their relation to human bcl-2 mRNA is indicated. The TI-AS oligodeoxynucleotide is antisense at the translation initiation site and TI-S is its complementary sense version. SD-AS and SD-S are oligodeoxynucleotides having antisense and sense orientations, respectively, relative to the splice donor region.

The oligodeoxynucleotide TI-AS straddles the predicted translation-initiation site of bcl-2 mRNAs and is complementary (antisense) to this region. As a control, the sense version of this 20 bp oligodeoxynucleotide, TI-S, was also synthesized.

In an effort, to specifically block splicing of bcl-2 mRNAs, a 20 bp antisense oligodeoxynucleotide, SD-AS, was synthesized that overlaps the splice donor site in bcl-2 primary transcripts. In addition, a complementary sense oligodeoxynucleotide, SD-S, was prepared as depicted in Table I. The human bcl-2 gene gives rise to several transcripts through alternative splice site selections, see Tsujimoto et al., *Proc. Natl. Acad. Sci. USA*, 83:5214–5218 (1986). The preponderance of these transcripts depend upon splicing and encode a 26 kDa protein, bcl-2-alpha. One minor transcript, however, does not undergo a splice and consequently encodes a 22 kDa protein bcl-2-beta. The SD-AS oligodeoxynucleotide can thus potentially block maturation of most but not all bcl-2 transcripts.

EXAMPLE 2

Treatment of Serum for In Vitro Investigations of Antisense Normal Oligodeoxynucleotides Because normal oligodeoxynucleotides are sensitive to degradation by nucleases present in serum, the efficacy of the TI-AS oligodeoxynucleotide in fetal bovine serum (FBS) heated for 30 minutes at 56° C. (the usual procedure for inactivating serum complement) was contrasted with the efficacy of TI-AS in FBS heated for 1 hour at 68° C., a temperature sufficient for irreversible inactivation of many nucleases. The RS11846 follicular lymphoma cell line was used. RS11846 cells contain a t (14; 18) chromosomal translocation that deregulates bcl-2 expression, resulting in the accumulation of high levels of bcl-2 mRNAs, Tsujimoto et al., *Proc. Natl. Acad. Sci. USA*, 83:5214–5218 (1986).

RS11846 follicular lymphoma cells were cultured in medium containing 5% (vol:vol) fetal bovine serum (FBS) that had been heated at 56° C. for 0.5 hours or at 68° C. for 1 hour. TI-AS normal oligodeoxynucleotide was added at the initiation of culture, and the density of viable cells determined two days later.

The TI-AS normal oligodeoxynucleotide was more effective in 68° C.-treated serum at suppressing the growth in culture of these lymphoma cells. In all subsequent experiments, sera heated at 68° C. for 1 hour prior to use were used in cultures. This treatment did not impair the growth-supporting capacity of the sera.

EXAMPLE 3

Specific Inhibition of Lymphoid Cell Growth by Antisense Normal Oligodeoxynucleotides Antisense normal oligodeoxynucleotides directed against the translation initiation site (TI-AS) and the splice donor site (SD-AS) of bcl-2 transcripts were tested for their ability to suppress the proliferation of normal and neoplastic lymphoid cells.

RS11846 follicular lymphoma cells, JUKRAT T cell leukemia cells, and freshly isolated peripheral blood lymphocytes were cultured in medium containing 10% (vol:vol) FBS that had been heated at 68° C. for one hour. various concentrations of normal oligodeoxynucleotides were added at the initiatIon of culture, including: TI-AS, TI-S, SD-AS, and SD-S. Relative DNA synthesis was measured in cultures after 2–3 days by [$^3$H]-thymidine incorporation. Data were calculated as a percentage of control cultures containing volumes of PBS or HBSS equivalent to oligodeoxynucleotide-treated cultures, and represent the mean (± standard deviation) of duplicate cultures.

Similar data were obtained by measuring cell counts, excluding cold thymidine inhibition as an explanation for the suppression of DNA synthesis observed in cultures treated with antisense oligodeoxynucleotides.

As shown in FIG. 1, both the TI-AS and SD-AS oligodeoxynucleotides inhibited the growth of RS11846 cells in a concentration-dependent manner. The SD-AS oligonucleotide was less effective in inhibiting cell growth than the TI-AS oligodeoxynucleotide. In contrast to these antisense oligodeoxynucleotides, sense oligodeoxynucleotides (TI-S and SD-S) were not inhibitory even at concentrations of up to 250 µG/ml. Moreover, non-sense oligodeoxynucleotides (i.e., those having the same base composition as the antisense oligodeoxynucleotides but with scrambled sequences) also failed to suppress the proliferation of RS11846 cells. The data thus indicate that antisense oligodeoxynucleotides can specifically block the proliferation of these tumor cells. Several other leukemic cell lines that express the bcl-2 gene were also tested for inhibition of their proliferation by TI-AS and SD-AS oligonucleotides. As with the JURKAT T cell acute lymphocytic leukemic cells, in every case a specific and concentration-dependent decrease in the growth of these human leukemic cells in cultures containing antisense oligodeoxynucleotides was observed.

It has been demonstrated that bcl-2 expression is transiently induced in normal human peripheral blood lymphocytes (PBL) when these cells are stimulated to proliferate, suggesting that this gene may play a role in the regulation of normal lymphocyte growth, Reed et al., *Science* 236:1295–1297 (1987). The capacity of antisense oligodeoxynucleotides to impair the growth of PBL cultured with a monoclonal antibody, OKT3 (Van den Elsen et al., *Nature* 312:413–418 (1984)), that stimulates their proliferation was therefore tested. PBL were stimulated with 50 µl of purified OKT3 monoclonal antibody. As shown in FIG. 1, the TI-AS oligodeoxynucleotide specifically suppressed the proliferation of PBL in a concentration-dependent manner. These antisense normal oligodeoxynucleotides thus suppressed the growth in culture of leukemic cells that constitutively express the bcl-2 gene and of normal lymphocytes where in bcl-2 expression is inducible.

EXAMPLE 4

Time-Course of Inhibition by Antisense Normal Oligodeoxynucleotides

The kinetics of inhibition by antisense oligodeoxynucleotides was examined in cultures of RS11846 follicular lymphoma cells and of 697 pre-B cell acute lymphocytic leukemia cells. Both of these neoplastic B cell lines transcribe and accumulate bcl-2 mRNAs at high levels, Tsujimoto et al., Proc. Natl. Acad. Sci. USA, 83:5214–5218 (1986).

RS11846 follicular lymphoma and 697 pre-B cell leukemia cells were cultured in medium containing 10% (vol:vol) 68° C.-treated FBS and normal oligodeoxynucleotides. Cells were cultured with 50 µg/ml TI-AS, 100 µg/ml SD-AS, 50 µg/ml TI-S (RS11846 cells) or 100 µg/ml SO-S (697 cells), or PBS as a control. DNA synthesis (kcpm/$10^5$ viable cells) and cell densities ($10^5$ viable cells/ml) were measured at various times after initiation of cultures.

Antisense normal oligodeoxynucleotides markedly inhibited DNA synthesis measured in cultures of these cells within 24 hours. Diminished cell densities were readily apparent in these cultures within 2 days. Antisense normal oligodeoxynucleotides thus rapidly inhibited the in vitro growth of leukemic cells. The action of antisense oligodeoxynucleotides was specific, since sense oligodeoxynucleotides did not impair proliferation in these cultures. Though cell viabilities often declined during the later days of culture no increase in cell death was seen during the first 1–2 days of culture with antisense oligodeoxynucleotides, suggesting a non-cytotoxic mechanism.

EXAMPLE 5

Comparision of Different Serum Preparations

Inhibition of proliferation of leukemic cells with antisense oligodeoxynucleotides can vary greatly depending on the lot of serum used in cultures.

To determine the effects of serum of inhibition of proliferation, relative levels of DNA synthesis were measured in cultures of 697 pre-B cell leukemia cells 2 days after addition of 200 µM TI-AS normal oligodeoxynucleotide. Cells were cultured in medium supplemented with 1% (vol:vol) HL1-concentrate (serum-free condition), 5% (vol:vol) of two different lots of calf serum (CS1 and CS2), or 5% (vol:vol) of two different lots of fetal bovine serum (FBS1 and FBS2). All sera were heated at 68° C. for 1 hour prior to use in cultures.

The normal TI-AS oligodeoxynucleotide markedly inhibited DNA synthesis (92%) and cellular proliferation in serum-free cultures (HL1) of 697 cells. This antisense oligodeoxynucleotide was equally effective (94%) in cultures containing 5% (v:v) of one of the lots of fetal bovine serum (FBS2). In contrast, inhibition was significantly reduced in cultures containing other serum preparations (CS1, CS2, FBS1). It has been generally observed that antisense normal oligodeoxynucleotides are less effective in cultures supplemented with calf serum (CS) than in those containing fetal bovine serum (FBS).

EXAMPLE 6

Concentration Dependence of Inhibition by Antisense Normal Oligodeoxynucleotides in Serum-Free Cultures 697 pre-B cell leukemia cells were cultured in medium with either 1% (vol:vol) HL1-concentrate (serum-free conditions or 5% (vol:vol) 68° C.-treated FBS2). Relative levels of DNA synthesis and cellular densities measured after 2 days in cultures containing various concentrations of normal TI-AS oligodeoxynucleotide.

The TI-AS oligodeoxynucleotide was inhibitory at lower concentrations when used in serum-free cultures. At 100 µM, for instance, no inhibition of cellular proliferation was seen in FBS2-containing cultures, whereas cell counts were reduced by approximately 75% in serum-free cultures. At higher concentrations of antisense oligodeoxynucleotides (200–250 µM), however, inhibition of 697 cellular proliferation was comparable in both types of cultures. The increased efficacy of normal oligodeoxynucleotides in serum-free cultures was specific, since the sense oligonucleotide (TI-S) was not inhibitory at the same concentrations.

EXAMPLE 7

Antisense Phosphorothioate Oligodeoxynucleotides:

Time Course of Inhibition

To contrast the efficacy of phosphorothioate oligodeoxynucleotides with that of normal oligodeoxynucleotides with regard to inhibition of human leukemic cell growth, phosphorothioate oligodeoxynucleotides were cultured with 697 pre-B cell leukemia cells and the effects on inhibition were measured. 697 pre-B cell leukemia cells were cultured in serum-free medium for various times before measuring DNA synthesis (kcpm) and cell densities ($10^6$ cells/ml). Cells were seeded at an initial density cf either $0.2\times10^5$ cells/ml or $0.5\times10^5$ cells/ml. Culture conditions were 25 µM TI-AS phosphorathioate, 25 µM TI-S phosphorothioate, and control cultures treated with HBSS.

To avoid experimental variation due to differences among lots of sera, 697 leukemic cells were cultured in serum-free conditions. When cultured at an initial seeding density of $0.5\times10^6$ cells/ml, 697 cells achieved maximal DNA synthesis and cellular densities at 4–5 days. Addition of 25 µM sense phosphorothioate oligodeoxynucleotide (TI-S) at the initiation of these cultures had little effect on 697 cell growth. In replicate cultures containing 25 µM antisense phosphorothioate (TI-AS), however, some diminution in DNA synthesis was evident within 2 days and was maximal at 4–5 days. Maximal inhibition of 697 cell growth, as determined by cell counts, was seen at 6 days after initiation of cultures.

When 697 cells were initially seeded at $0.2\times10^6$ cells/ml, the antisense phosphorothioate oligodeoxynucleotide, TI-AS, resulted in only slight inhibition at 2 days, attaining maximal suppression of DNA synthesis in these cultures at day 7. As with normal oligodeoxynucleotides, this inhibition by phosphorothioate oligodeoxynucleotides appeared to be mediated through non-cytotoxic mechanisms, since cellular viabilities did not decline until late in the course of culture. Compared with normal antisense oligodeoxynucleotides, therefore, phosphorothioate oligodeoxynucleotides had a slower onset of action.

EXAMPLE 8

Concentration Dependence of Inhibition by Antisense bcl-2 Phosphorothioate oligodeoxynucleotides The concentration descendence of inhibition by phosphorothioate and normal TI-AS oligodeoxynucleotides in cultures of 697 cells in serum-free medium was compared as follows.

697 cells were cultured in serum-free medium for either 3 days (normal oligodeoxynucleotides) or 4 days (phosphorothioate oligodeoxynucleotides) prior to measuring cell densities and levels of DNA synthesis. Oligodeoxynucleotide additions to cultures included TI-AS phosphorothioate, TI-S phosphorothioate, TI-AS normal, and TI-S normal.

Figure 2A:
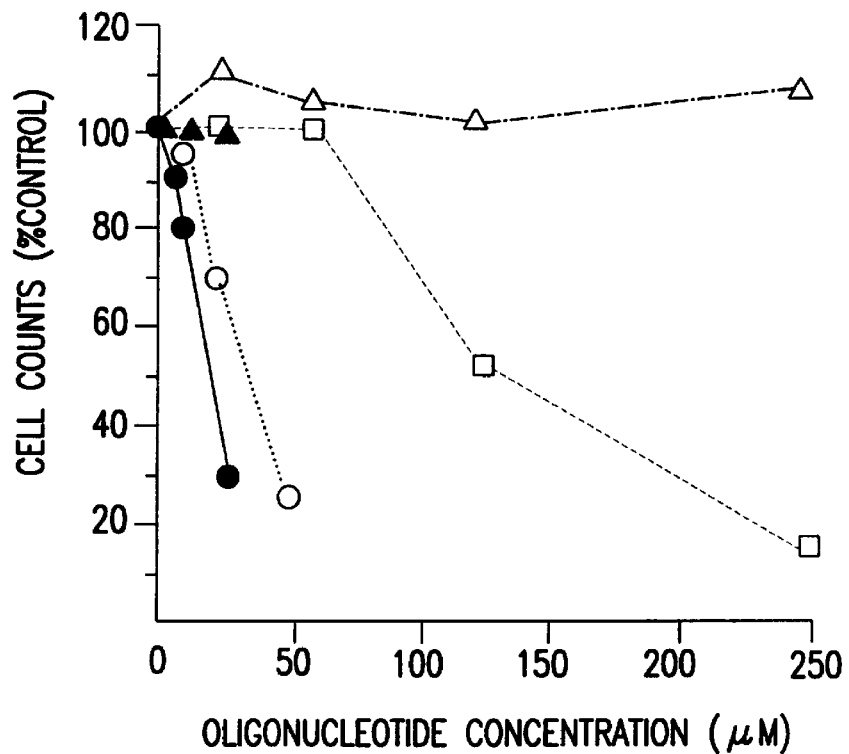
FIG. 2 shows graphs of the concentration dependence of inhibition of cell proliferation by antisense normal and phosphorothioate oligodeoxynucleotides. Oligodeoxynucleotide additions to cultures included TI-AS phosphorothioate (○ and ●; two separate experiments), TI-S phosphorothioate (▲), TI-AS normal (□), and TI-S normal (Δ).
Figure 2B:
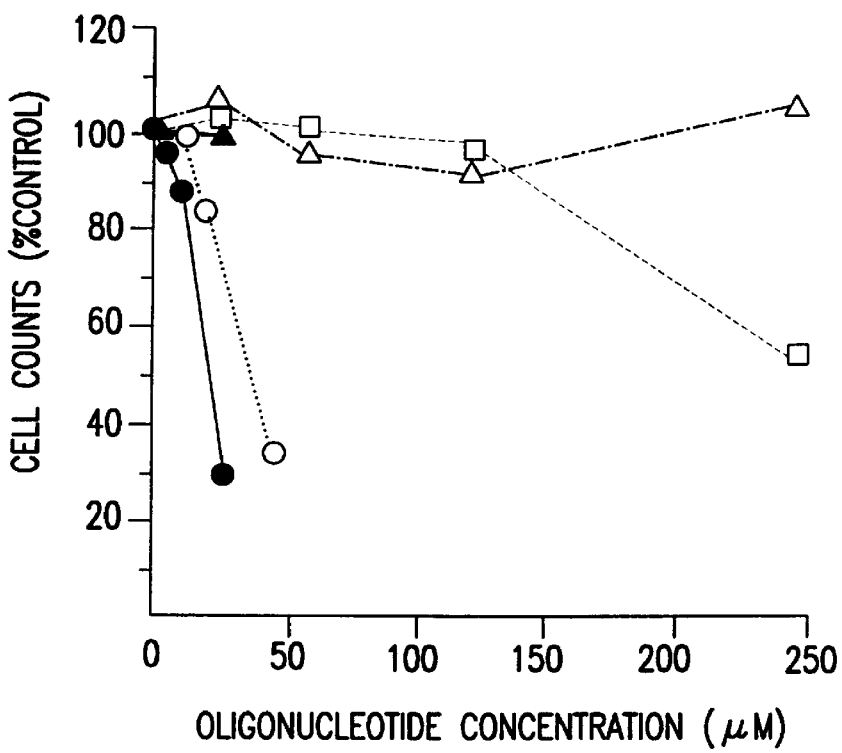

As shown in FIG. 2, TI-AS phosphorothioate oligodeoxynucleotides markedly inhibited the proliferation of 697 cells at 25–50 μM. In contrast, normal TI-AS oligodeoxynucleotides required concentrations 5- to 10-fold higher (approximately 250 μM) to cause a comparable suppression of 697 cellular proliferation. Suppression by the antisense phosphorothioate oligodeoxynucleotide TI-AS was specific over this concentration range, since its complementary sense oligodeoxynucleotide (TI-S) produced little inhibition of 697 cell growth in replicate cultures (see FIG. 2).

EXAMPLE 9

Influence of Serum Preparation on Inhibition by Antisense Phosphorothioate Oligodeoxynucleotides To further define the effects of serum preparation on the inhibitory activity of phosphorothioate oligodeoxynucleotides, FBS that had been heated to 56° C. for 30 minutes, 68° C. for 1 hour, or not heated prior to addition to cultures was added to cultures of RS11846 lymphoma cells.

RS11846 cells were cultured in medium containing 1% (vol:vol) HL1-concentrate or 5% (vol:vol) FBS that had been heated at 56° C. for 0.5 hour, 68° C. for 1 hour, or that had not been heated. Cell counts were calculated as a percentage relative to control cultures treated with equivalent concentrations of TI-S phosphorothioate oligodeoxynucleotide, and represent the mean percentage (standard deviation was less than 10% for all values) for duplicate cultures counted on days 4 and 5.

The TI-AS phosphorothioate oligodeoxynucleotide completely inhibited the growth of RS11846 cells at 25 μM, with an estimated half-maximal inhibitory concentration of approximately 11 μM. In contrast, this phosphorothioate oligodeoxynucleotide was considerably less effective in cultures containing 5% (v:v) FBS. Furthermore, heating FBS prior to adding it to cultures did not significantly improve the ability of the TI-AS phosphorothioate oligodeoxynucleotide to suppress the growth of RS11846 lymphoma cells. At an oligodeoxynucleotide concentration of 50 μM, inhibition of proliferation of RS11846 cells never exceeded 48% serum-containing cultures, regardless of the heating procedure used.

EXAMPLE 10

Influence of Dialysis of Serum on Inhibition by Normal and Phosphorothioate Antisense Oligodeoxynucleotides To further characterize the nature of the interfering substances in serum, experiments were performed wherein 68° C.-heated serum was extensively dialyzed (molecular weight cutoff=3500) prior to being added to cultures of 697 leukemic cells. Experiments were conducted with 12.5 μM TI-AS phosphorothioate oligodeoxynucleotide and 200 μM of the normal oxygen-based TI-AS oligcdeoxynucleotide.

697 cells were cultured in medium containing 1% (vol:vol) HL1-concentrate (A) or 5% (vol:vol) of three different lots of 68° C.-treated FBS (B,C,D). Each serum preparation was contrasted before (ND) and after (D) extensive dialysis. TI-AS (+) and TI-S (−) oligodeoxynucleotides were added to replicate cultures at 200 μM for normal oxygen-based oligodeoxynucleotides (OXY) and at 12.5 μM for phosphorothioate oligodeoxynucleotides (PT). Relative levels of DNA synthesis (kcpm) were measured after 2 or 4 days of culture for normal and phosphorothioate oligodeoxynucleotides, respectively.

For the three different lots of FBS tested, two exhibited little change after dialysis in cultures containing either normal or phosphorothioate oligodeoxynucleotides. One lot of FBS, however, appeared to interfere less with the inhibitory activities of these antisense oligodeoxynucleotides after dialysis.

EXAMPLE 11

Experiments with Stably Transfected NIH 3T3 Cells

Though the antisense oligodeoxynucleotides described herein were designed to block bcl-2 mRNA translation (TI-AS) and splicing (SD-AS), the molecular mechanisms of their actions are not yet known. To determine the effect of formation of oligodeoxynucleotide-RNA hybrids within cells upon inhibition of cellular growth, irrespective of the nucleotide sequence, cells transformed to express human bcl-2 cDNA transcripts were cultured with normal oligodeoxynucleotides.

200 μM of normal TI-AS and TI-S oligodeoxynucleotides were added to cultures of typical NIH 3T3 cells and to cultures of these cells that had been stably transfected with expression constructs that produce high levels of human bcl-2 cDNA transcripts for either the usual sense (3T3-alpha-S cells) or the antisense (3T3-alpha-AS cells) strand.

For RNA blot analyses, polyadenylated mRNA was purified from normal NIH 3T3 cells and from cells stably transfected with expression constructs that produce either sense (3T3-alpha-S) or antisense (3T3-alpha-AS) recombinant bcl-2-alpha mRNAs, according to the method of 13. Approximately 5 μg of mRNA was subjected to RNA blot analysis, essentially as described in (16), using either 32p-labeled hybridization probes derived from human or murine bcl-2 sequences.

An autoradiogram resulting from a one-day exposure of a blot containing RNAs from normal 3T3 cells, 3T3-alpha-AS cells, and 3T3-alpha-S cells showed high relative levels of recombinant 2.4 and 1.4 kbp bcl-2 transcripts produced from the bcl-2 expression constructs that were transfected into 3T3-alpha-AS and 3T3-alpha-S cells.

A 10-day exposure of a blot containing RNA from normal 3T3 cells that were either proliferating or quiescent at the time of harvesting RNA showed low but detectable levels of normal 7.5 and 2.4 kbp murine bcl-2 transcripts present in proliferating 3T3 cells.

TI-AS oligodeoxynucleotide specifically suppressed DNA synthesis and cellular replication in cultures of normal NIH 3T3 cells, consistent with findings by others that fibroblasts do contain bcl-2 transcripts, albeit at low levels. The TI-AS oligodeoxynucleotide disclosed herein is complementary to the mouse bcl-2 sequence in 18 of its 20 bases (17), accounting for its ability to suppress the growth of murine NIH 3T3 cells.

NIH 3T3 cells, 3T3-alpha-AS cells, and 3T3-alpha-S cells were cultured in medium containing 5% (vol:vol) 68° C.-treated serum and either HBSS, 200 μM TI-S normal oligodeoxynucleotide, or 200 μM TI-AS normal oligodeoxynucleotide. Relative levels of DNA synthesis (kcpm) were measured in cultures after 3 days and reflect a 16 hour incubation with 0.5 μci/well of [$^3$H]-thymidine. Cell densities, estimated by phase microscopy, were consistent with the measured DNA synthesis in cultures. The percentage of inhibition of DNA synthesis in cultures containing TI-AS oligodeoxynucleotides was calculated relative to control cultures containing HBSS.

As with normal NIH 3T3 cells, culturing 3T3-alpha-S cells (producing human bcl-2-alpha sense transcripts) with TI-AS and TI-S oligodeoxynucleotides demonstrated specific suppression, since the sense oligodeoxynucleotide TI-S was not inhibitory. The level of inhibition of cellular proliferation by the antisense oligodeoxynucleotide, however, was not as great in 3T3-alpha-S cells, as might be expected, since these cells contain more bcl-2 mRNA.

Adding TI-S oligodeoxynucleotide to cultures of 3T3-alpha-AS cells (produce antisense bcl-2 transcripts) ruled out inhibition of cellular growth through a nonspecific mechanism involving oligodeoxynucleotide-RNA hybrid formation. The TI-S oligodeoxynucleotide caused little suppression of 3T3-alpha-AS cell proliferation, whereas the TI-AS oligodeoxynucleotide was markedly inhibitory in these cells. Similar data were obtained with TI-AS and TI-S phosphorothioate oligodeoxynucleotides.

EXAMPLE 12

Measurements of DNA Fragmentation as an Indicator of bcl-2 Antisense Oligodeoxynucleotide-Mediated Programmed Cell Death in Human Lymphoma Cells Oligonucleotides having the sequences shown in Table 2 were tested for the ability to induce programmed cell death (DNA fragmentation) in the human t(14:18)-containing human lymphoma cell line RS11846. The oligonucleotides were all phosphodiesters, and were targeted against the translation initiation site or the 5'-cap region of bcl-2 pre-mRNAs. Control oligodeoxynucleotides included a bcl-2 sense version (TI-S) of TI-AS (having SEQ ID NO: 7) and a scrambled version of TI-AS that has the same base composition, but with jumbled nucleotide order.

TABLE 2

| SEQUENCE | SEQ ID NO: |
| --- | --- |
| CGCGTGCGAC CCTCTTG | 8 |
| TACCGCGTGC GACCCTC | 9 |
| CCTTCCTACC GCGTGCG | 11 |
| GACCCTTCCT ACCGCGT | 12 |
| GGAGACCCTT CCTACCG | 13 |
| GCGGCGGCAG CGCGG | 14 |
| CGGCGGGGCG ACGGA | 15 |
| CGGGAGCGCG GCGGGC | 16 |

RS11846 cells were adapted to grow in HL1 media with 1% FCS and their DNA metabolically labeled by addition of $^{125}$I-deoxyuridine to cultures for three hours. Labeled cells were then washed thoroughly and cultured for two days in the presence of various oligonucleotides at 50 μM. Cells were then recovered from 200 μL cultures by centrifugation, and lysed in a hypotonic buffer containing 10 mM EDTA and 14 Triton X100. After centrifugation at 16,000×g to pellet unfragmented genomic DNA, the supernatant fraction containing fragmented DNA was extracted with phenol/chloroform and ethanol precipitated. This DNA was then subjected to gel electrophoresis in 1.5% agarose gel and transferred to nylon membranes for autoradiography.

Figure 3:
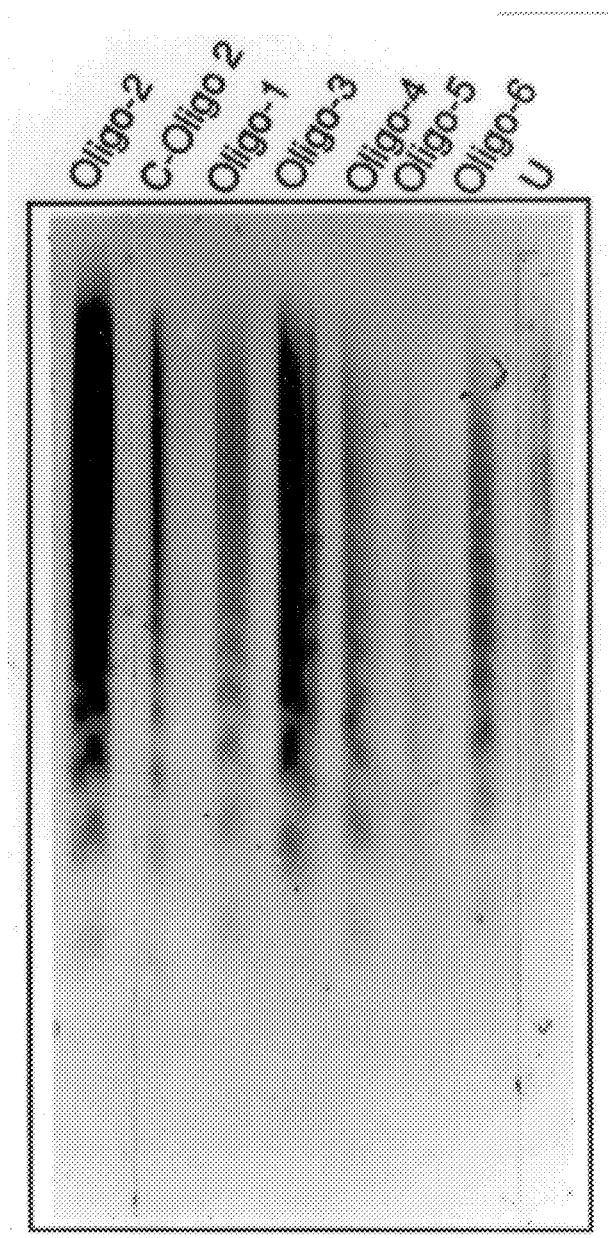
FIG. 3 shows the results of gel electrophoresis of six antisense oligonucleotides targeted against the translation initiation site of bcl-2 mRNA.
Figures 4A, 4B:
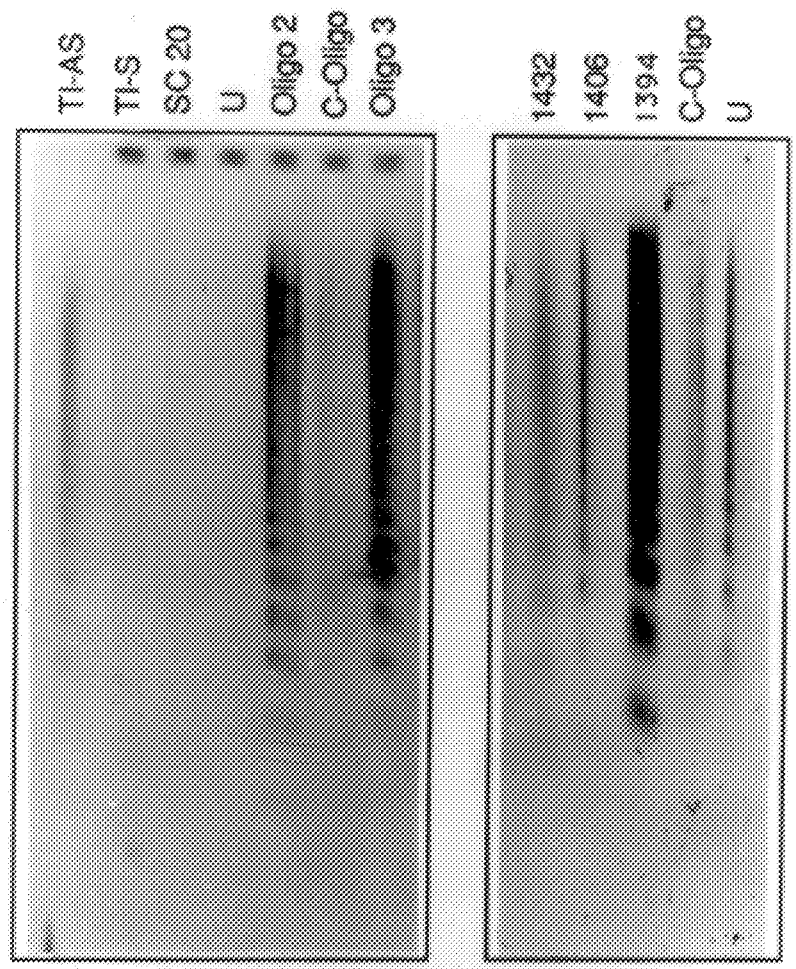
FIGS. 4A–4B show the degree of DNA fragmentation resulting from oligonucleotide treatment of RS11846 cells.

The results of two experiments are shown in FIGS. 3 and 4. The six bcl-2 antisense oligonucleotides targeted in the vicinity of the ATG site of translation initiation in bcl-2 mRNAs were tested. "C-Oligo-2" refers to an oligonucleotide with 4 purposeful mismatches. "U" indicates untreated control cells. FIG. 4 shows the results for the oligonucleotides shown in FIG. 3. "Sc2O" refers to a 20 mer with the same base composition as TI-AS, but with scrambled sequence. FIG. 4(b) shows the results for three oligonucleotides targeted against the 5'-cap of bcl-2 mRNAs. The numbers refer to the distance of these oligomers from the ATG-translation initiation site.

The presence of a ladder of DNA fragments (unit size of approximately 200 bp) is indicative or programmed cell death. At 50 μM, TI-AS caused little DNA fragmentation, whereas the oligonucleotides having SEQ ID NO: 9 and SEQ ID NO: 10, and one of the 5'-cap oligonucleotides (SEQ ID NO: 14) led to pronounced DNA fragmentation.

EXAMPLE 13

Figure 5:
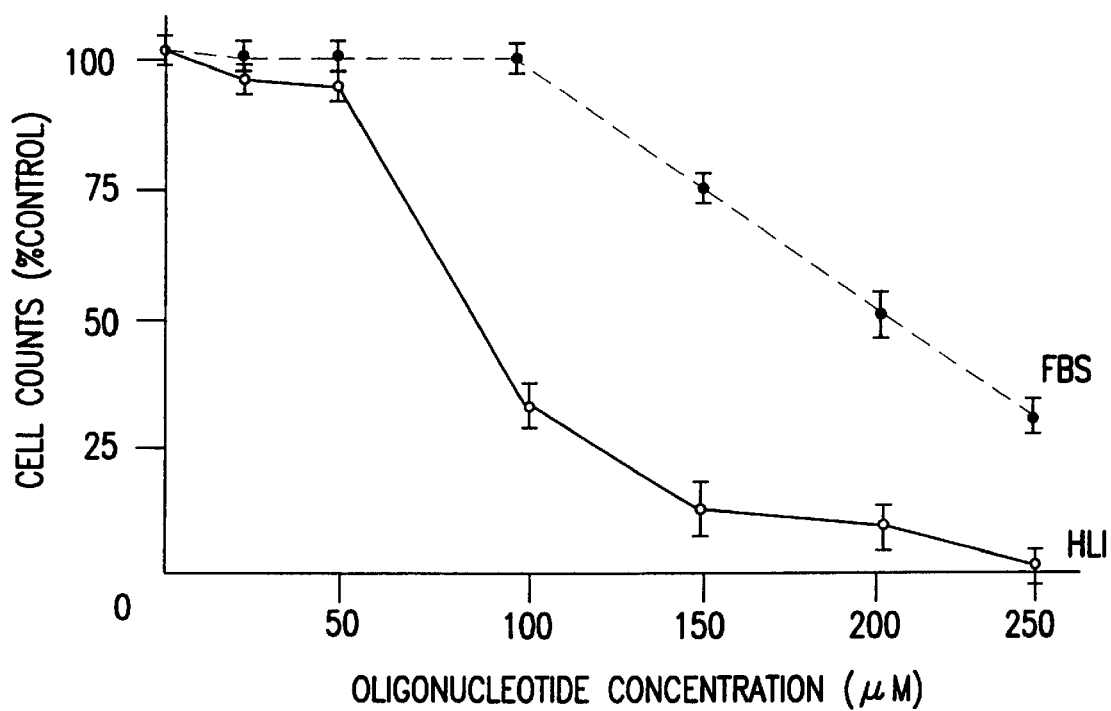
FIG. 5 is a graph showing the concentration—dependence of inhibition by an antisense oligonucleotide targeted against the translation initiation site of bcl-2 mRNA.

Concentration-Dependence of Inhibition by Antisense Phosphodiester Oligodeoxynucleotides in Serum-Free Cultures 697 pre-B cell leukemia cells were cultured in medium with either 1% (vol:vol) HL-1 concentrate (serum-free conditions [o] or 3% (vol:vol) 68° C.-treated serum (FBS2) [], see FIG. 5. Shown are cellular densities measured after 2 days in cultures containing various concentrations of phosphodiester TI-AS oligodeoxynucleotide. Data are shown as percentages relative to control cultures treated with a sense oligonucleotide, and reflect the mean±standard deviation for duplicate samples.

EXAMPLE 14

Immunofluorescence Analysis of bcl-2 Protein Levels in Oligodeoxynucleotide-Treated 697 Cells For studies with oligodeoxynucleotides, 0.25×10$^4$ (for phosphorothioate) or 0.5×10$^5$ (for normal oligodeoxynucleotides), 697 cells were cultured in 1 ml of HL-1 serum-free medium in 24 well culture dishes (Linbro. Flow Lab, Inc.). After 2 days (for normal) or 4 days (for phosphorothioates), cells were recovered from cultures, washed once in [PBS, pH 7.4 (Gibco)—0.1% bovine serum albumin—0.1% sodium azide], and fixed for 5–10 minutes on ice in 1% paraformaldehyde/PBS solution. The cells were then washed once in PBS and incubated in 1 ml of absolute methanol at 20° C. for 10 minutes. After washing once in PBS-A, cells were then resuspended in PBS containing 0.05% Triton-X100 for 3 minutes on ice, washed in PBS-A and preblocked for 30 minutes at 4° C. in PBS with 10% (v/v) heat-inactivated goat serum.

For addition of the first antibody, preblocked cells were resuspended in 100 μl of PBS-G (PBS-1% goat serum-0.1% sodium azide) prior to aliguoting 50 μl into separate tubes that contained 1 μl of either BCL2 antibody (Halder et al., Nature (London), 342:195–197 (1989)) or affinity-purified normal rabbit control IgG (Cappel 6012–0080) and incubated for 1 hour on ice. The BCL2 antibody used for these studies was prepared in rabbits using a synthetic peptide corresponding to amino acids (98–114) of the BCL2 protein and was affinity—purified by protein-A-Sepharose chromatography and used at approximately 1 mg/ml. Cells were then washed in PBS-A and incubated in 0.5–1.0 ml PBS-A for 15–20 minutes on ice to allow diffusion of nonspecific cell-associated antibody prior to resuspending cells in 100 μl of PBS-G containing 5 μg of biotinylated scat anti-rabbit IgG (BAIOOO; Vector Labs) for 30 minutes. After washing once and incubating for 15 minutes in PBS-A, cells were finally resuspended in 100 μl of PBS-A containing 2 μg of FITC-conjugated avidin (Vector Labs A2011) for 20 minutes and washed three times in PBS-A prior to analysis with an Ortho cytofluorograph 50-H connected to an Ortho 2150 data-handling system. The specificity of method for detecting BCL2 protein was confirmed by immunofluorescence microscopy (showing cytosolic stain peptide competition, and studies of cell lines that expressed various levels of BCL2 mRNA and proteins through gene transfer manipulations.

For measurements of surface HLA-DR antigen expression, an indirect immunofluorescence assay method was used (Reed et al., *J. Immunol.* 134:1631–1639 (1985)) involving incubation of viable cells with a murine anti-HLA-DR monoclonal antibody (IgG2a) (Becton-Dickinson 7360) or a negative control antibody, R3-367 (IgG2a), followed by FITC-conjugated scat anti-mouse IgG (Cappel 1711–0081). Cells were fixed in 1% paraformaldehyde/PBS prior to FACS analysis.

Figure 6A:
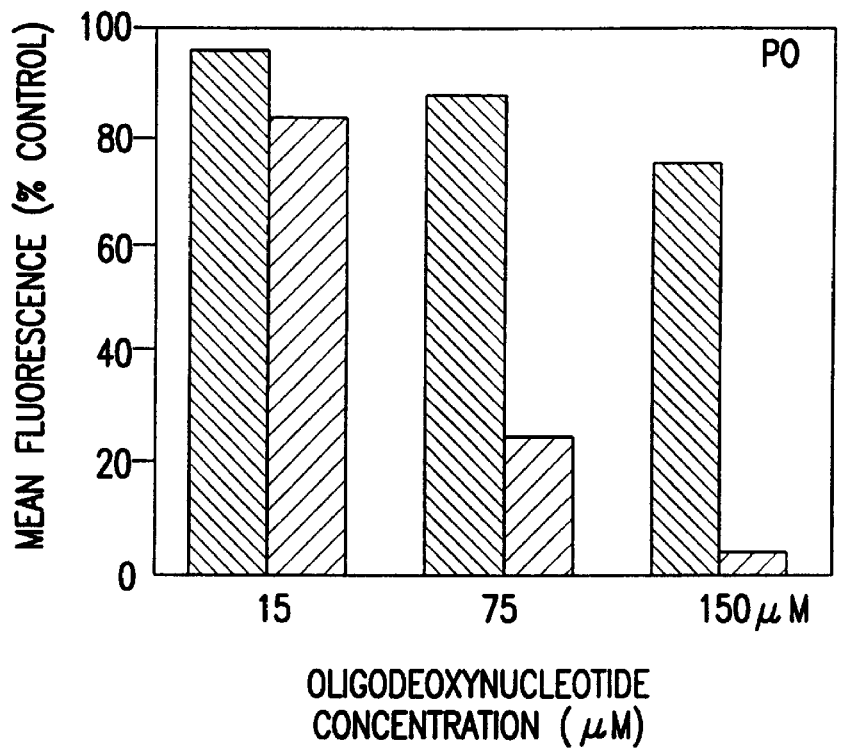
FIGS. 6A–6B show the results of immunofluorescence analysis of bcl-2 antisense oligonucleotides.
Figure 6B:
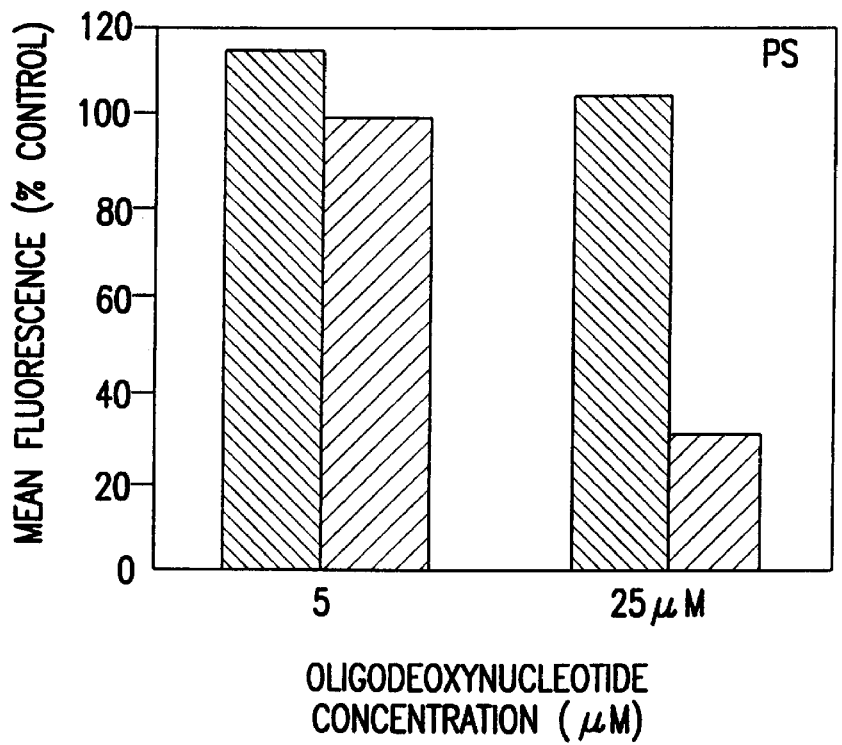
Figure 7A:
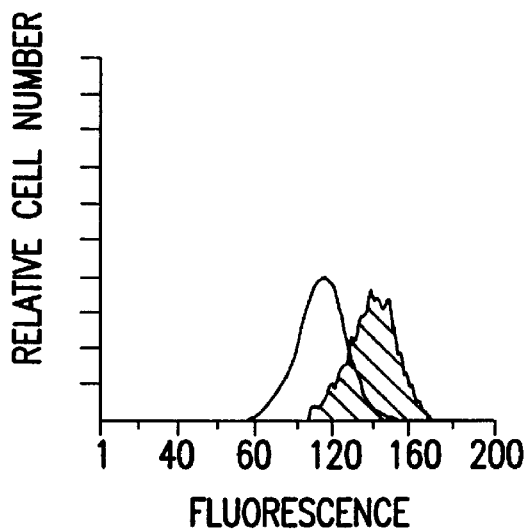
FIG. 7A shows untreated 607 cells labeled with either anti-bcl-2 antiserum (hatched area) or normal rabbit serum control (white area).
Figure 7B:
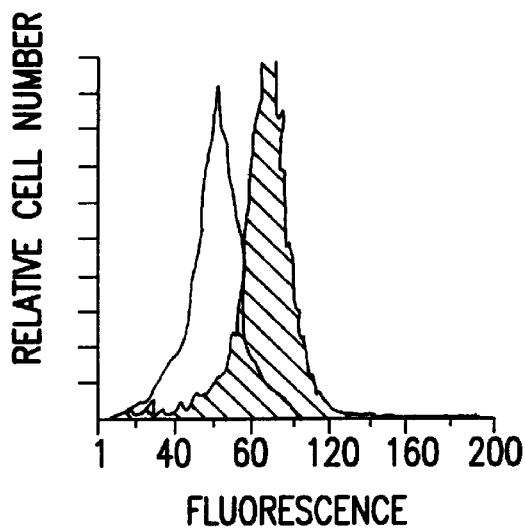
FIG. 7B shows untreated 697 cells labeled with either anti-HLA-DR antibody (hatched area) or a negative control antibody (white area).
Figure 7C:
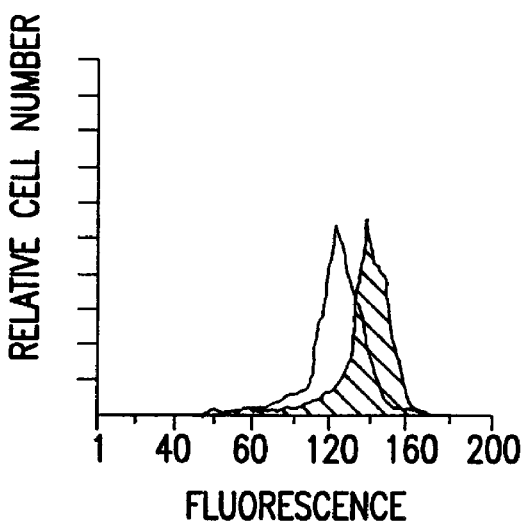
FIG. 7C shows 697 cells cultured for 2 days with either normal bcl-2 TI-AS (white area) or TI-AS (hatched area) oligonucleotides and labeled with anti-bcl-2 antibody.
Figure 7D:
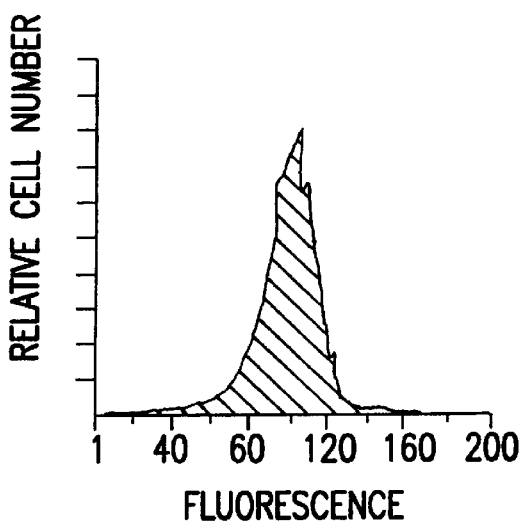
FIG. 7D shows 697 cells cultured with TI-AS and TI-S oligodeoxynucleotides (as in C), but labeled with anti-HLA-DR antibody.

697 cells were cultured for 2 days (PO) or 4 days (PS) with various oligonucleotides. In FIG. 6, the black columns show the results with a sense oligonucleotide, and the hatched columns with an antisense oligonucleotide TI-AS. Cells were labeled with anti-bcl-2 antiserum and analyzed by FACS. Data are expressed as percentages relative to the mean fluorescence obtained with untreated 697 cells.

FIG. 7 shows typical FACS results obtained for 697 cells before and after treatment with 100 μM PO bcl-2 antisense oligonucleotides. A: untreated 697 cells labeled with either anti-bcl-2 antiserum (hatched area) or normal rabbit serum control (white area); B: untreated 697 cells labeled with either anti-HLA-DR antibody (hatched area) or a negative control antibody (white area); C: 697 cells cultured for 2 days with either normal bcl-2 TI-AS (white area) or TI-AS (hatched area) oligodeoxynucleotides and labeled with anti-bcl-2 antibody; D: 697 cells cultured with TI-AS and TI-S oligodeoxynucleotides (as in C), but labeled with anti-HLA-DR antibody.

As shown in FIGS. 6 (*a*) and (*b*), PO and PS bcl-2 antisense oligonucleotides produced specific concentration-dependent reductions in the levels of bcl-2 proteins, without altering the levels of expression of HLA-DR (FIG. 7) and other control antigens. At 150 μM, for example, PO antisense oligodeoxynucleotide caused an approximately 75–95% reduction in bcl-2 fluorescence, whereas the control sense oligodeoxynucleotide diminished bcl-2 protein levels by only 10–20% (FIG. 6(*a*)). Similarly, cultured 697 cells for 4 days with the PS antisense oligodeoxynucleotide ar 25 μM resulted in approximately 70% reduction in bcl-2 fluorescence. In comparison, the sense PS oligodeoxynucleotide TI-S inhibited bcl-2 protein levels by only approximately 15%, as measured by this assay (FIG. 6(*b*)).

SIGNIFICANCE

In phosphorothioate oligodeoxynucleotides, one of the non-bridging oxygen atoms in each internucleotide phosphate linkage is replaced by a sulfur atom. This modification renders phosphorothioate oligodeoxynucleotides extremely resistant to cleavage by nucleases, Stein et al., *Nucl. Acids Res.*, 16:3209–3221 (1988). Despite the substitution of a sulfur atom for an oxygen, phosphorothioate oligodeoxynucleotides retain good solubility in aqueous solutions; hybridize well, though with some decrease in the melting temperature of RNA-oligodeoxynucleotides duplexes; and are synthesized conveniently by the widely employed method of automated oligodeoxynucleotides synthesis with phosphoroamidites.

Antisense bcl-2 phosphorothioate oligodeoxynucleotides have been found to be more potent inhibitors of leukemic cell grown than their normal oxygen-based counterparts. When tested under serum-free conditions, these oligodeoxynucleotides reduced cellular proliferation by half at concentrations of approximately 15–23 μM, whereas the normal oligodeoxynucleotide achieved 50% inhibition at 125–250 μM. This finding may be explained by the reduced sensitivity of phosphorothioate oligodeoxynucleotides to cellular nucleases, or may be attributable to other mechanisms. For example, mRNAs hybridized with phosphorothioate oligodeoxynucleotides may experience enhanced degradation through a mechanism involving an RNAse H-like activity.

Despite their increased inhibitory activity, phosphorathioate antisense oligodeoxynucleotides retained sequence-specificity. At the concentrations tested (less than 25 μM), sense versions of these oligodeoxynucleotides had little effect on leukemic cell growth. Both normal and phosphorothioate antisense oligodeoxynucleotides appeared to initially suppress the proliferation of leukemic cells through non-cytotoxic mechanisms. During the first few days of culture, cellular replication was inhibited without a concomitant rise in cell death. Later in these cultures (days 4–5 for normal oligodeoxynucleotides, days 6–8 for phosphorothioates), however, cellular liabilities declined.

Comparing the kinetics of inhibition by normal and phosphorothioate oligodeoxynucleotides revealed that the latter compounds have a slower onset of action. Maximal inhibition of leukemic cell proliferation by normal antisense oligodeoxynucleotides occurred two days after initiation of cultures, whereas phosphorothioate oligodeoxynucleotides required 4 to 7 days to achieve maximal inhibition.

The usefulness of anticode oligomers in inhibiting human lymphoma/leukemia cells and other types of cancer cells that express the bcl-2 gene has been shown by the examples herein. Anti-sense oligodeoxynucleotides complementary to at least an effective portion of the mRNA of the human bcl-2 gene has been found to inhibit growth of RS11846 human follicular lymphoma cells t (14;18) chromosomal translocation and high bcl-2 expression), 697 human pre B cell leukemia cells (high bcl-2 expression), JURKAT human acute lymphocytic leukemia cells (medium bcl-2 expression), normal human lymphocytes (medium bcl-2 expression) and murine fibroblasts (low bcl2 expression). Although bcl-2 antisense reagents can suppress the growth of many types of cells, the t(14:18) lymphoma and leukemia cells seem to be the sensitive, allowing for specific inhibition of malignant cells.

As demonstrated in the following Examples, a variety of DNA analogs can be employed in the instant invention. For example, phosphorothioates, methylphosphonates, and mixed oligomers containing combinations of phosphodiesters and phosphorothioate or methylphosphonate nucleosides. It shoud be understood that RNA analogs can also be employed in the invention.

EXAMPLE 15

Methylphosphonate (MP)/Phosphodiester (PO) bcl-2 Antisense oligomers Induce Death of DoHH2 Lymphoma Cells The purpose of this study was to determine the efficacy of various analogs of the anticode oligomers for inhibiting lymphoma cell survival.

DoHH2 is a human lymphoma cell line containing a t(14:18)-translocation that activates the bcl-2 gene. DoHH2 cells were cultured for 3 days without oligomers or in the presence of various concentrations of antisense (As) and scrambled (Sc) methylphophonate (MP)/Phosphodiester (PO) oligomers for 3 days. Cell viablity was assessed by trypan blue dye exclusions, and the data expressed as a percentage relative to DoHH2 cells cultured without oligomers. The MP/PO oligomers was an 18-mer targeted against the first 6 codons of the bcl-2 open reading frame in which 5 internal linkages were phosphodiester and the flanking nucleosides were methylphophonates.

The results indicate that these anticode oligomer analogs are potent and specific inhibitors of lymphoma cell survival.

EXAMPLE 16

Methylphosphonate (MP)/Phosphodiester (PO) Chimeric Oligomers Inhibit Growth of MCF-7 Human Breast Cancer Cells The purpose of this study was to determine the efficacy of the claimed anticode oligomer analogs to inhibit the survival of solid tumor cells which highly express bcl-2.

MCF-7 is a human breast adenocarcinoma cell line that contains relatively high levels of bcl-2 protein. The cells were cultured at 4,000 cells per well in 96-well microtiter plates in the presence or absence of MP/PO oligomers. Relative cell numbers per well were then estimated by MTT assay, based on a standard curve prepared using freshly plated, untreated MCF-7 cells. The antisense (As) and scrambled (Sc) MP/PO oligomers were the same as those described in Example 15. Data represent the mean+/- standard deviation for determinations.

The results demonstrate sequence specific inhibition of growth of solid tumor cells by the claimed anticode oligomer analogs.

EXAMPLE 17

Optimimization of Anticode bcl-2 Oligomer Sequences

The purpose of this study was to determine optimum target sites or sequence portions on mRNA for inhibiting cell survival by contacting the cells with various claimed anticode molecules whose sequences were computer generated.

Figure 13A:
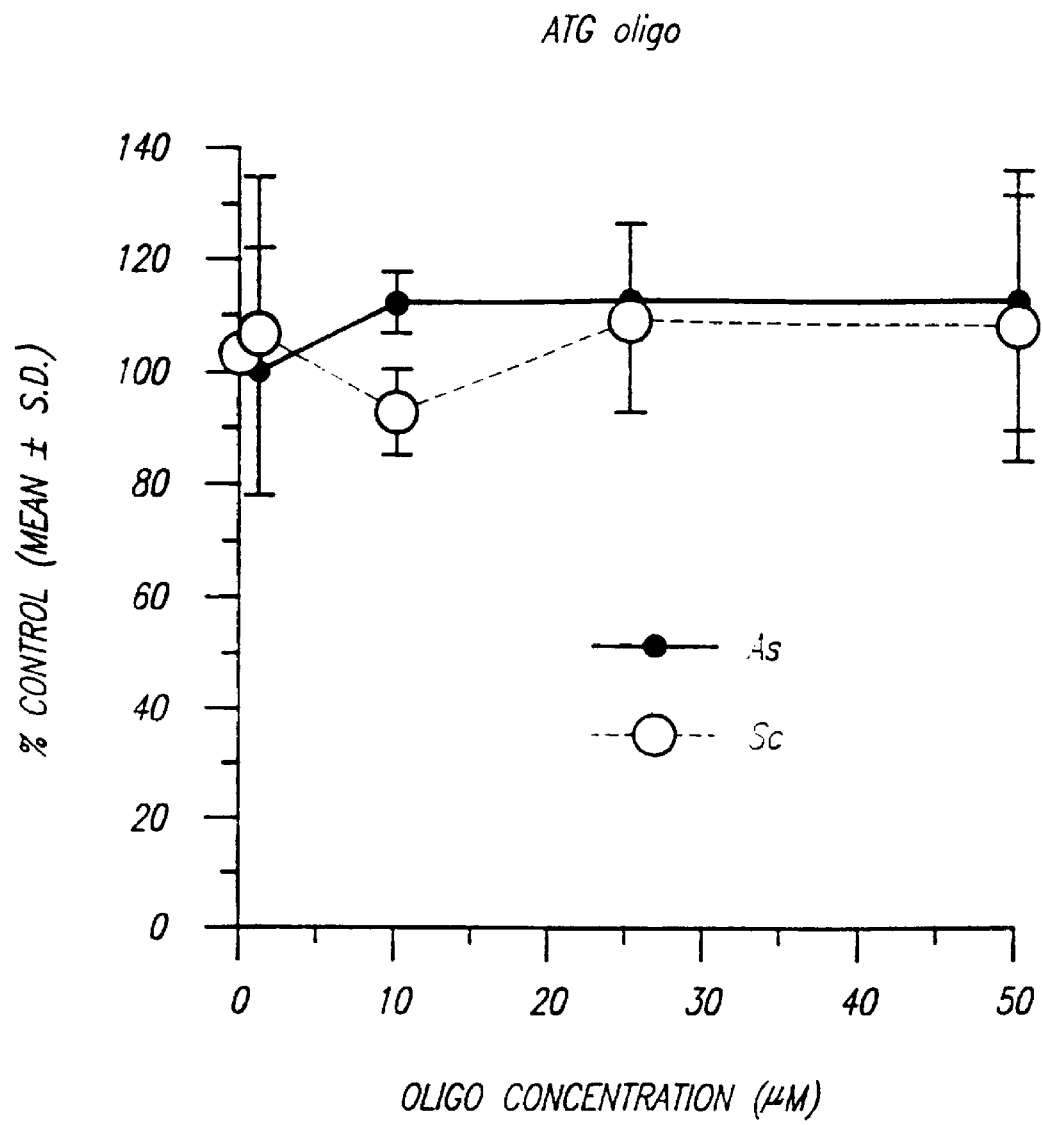
FIG. 13 shows optimization of antisense bcl-2 oligomer sequences.
Figure 13B:
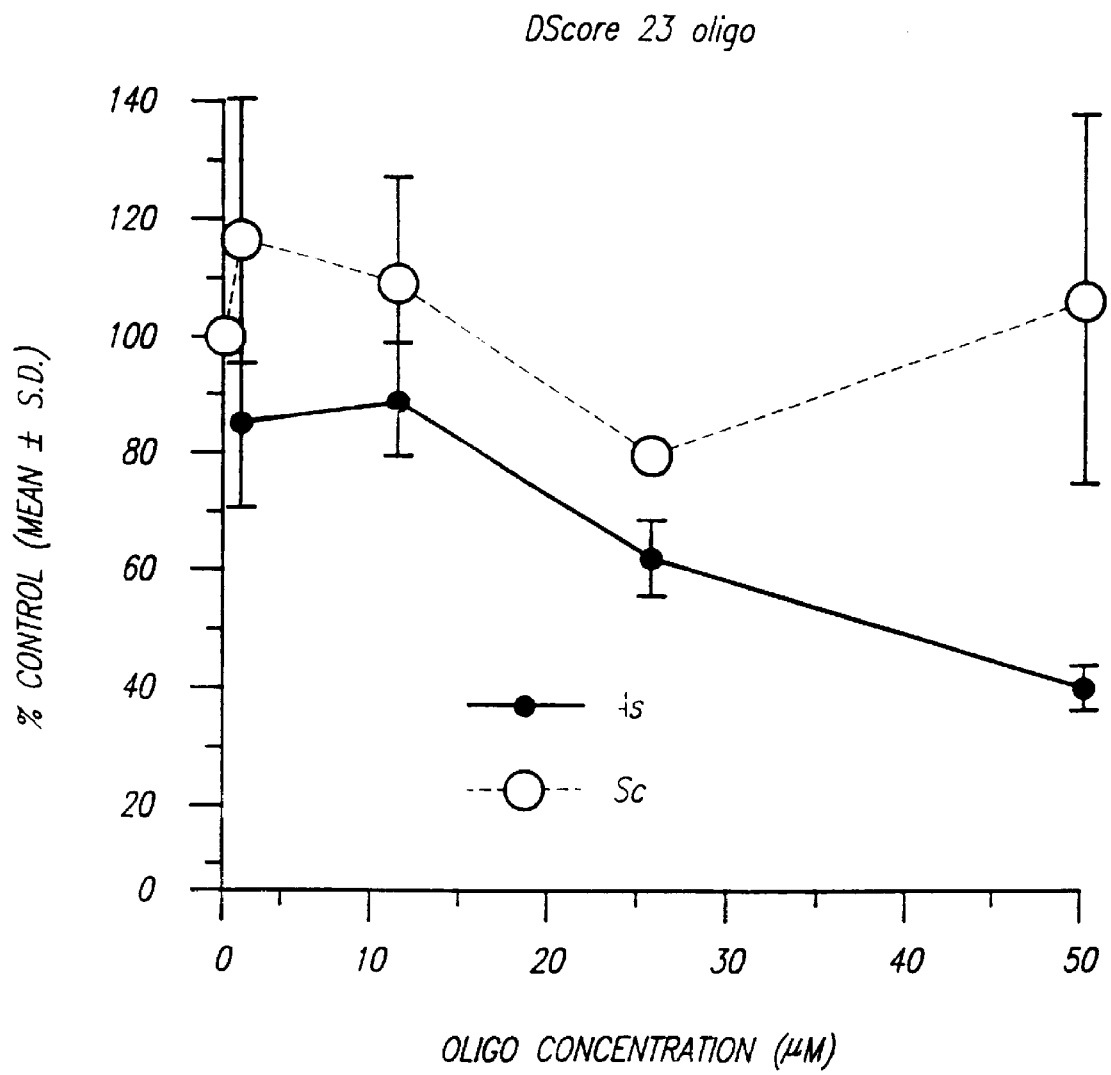
Figure 13C:
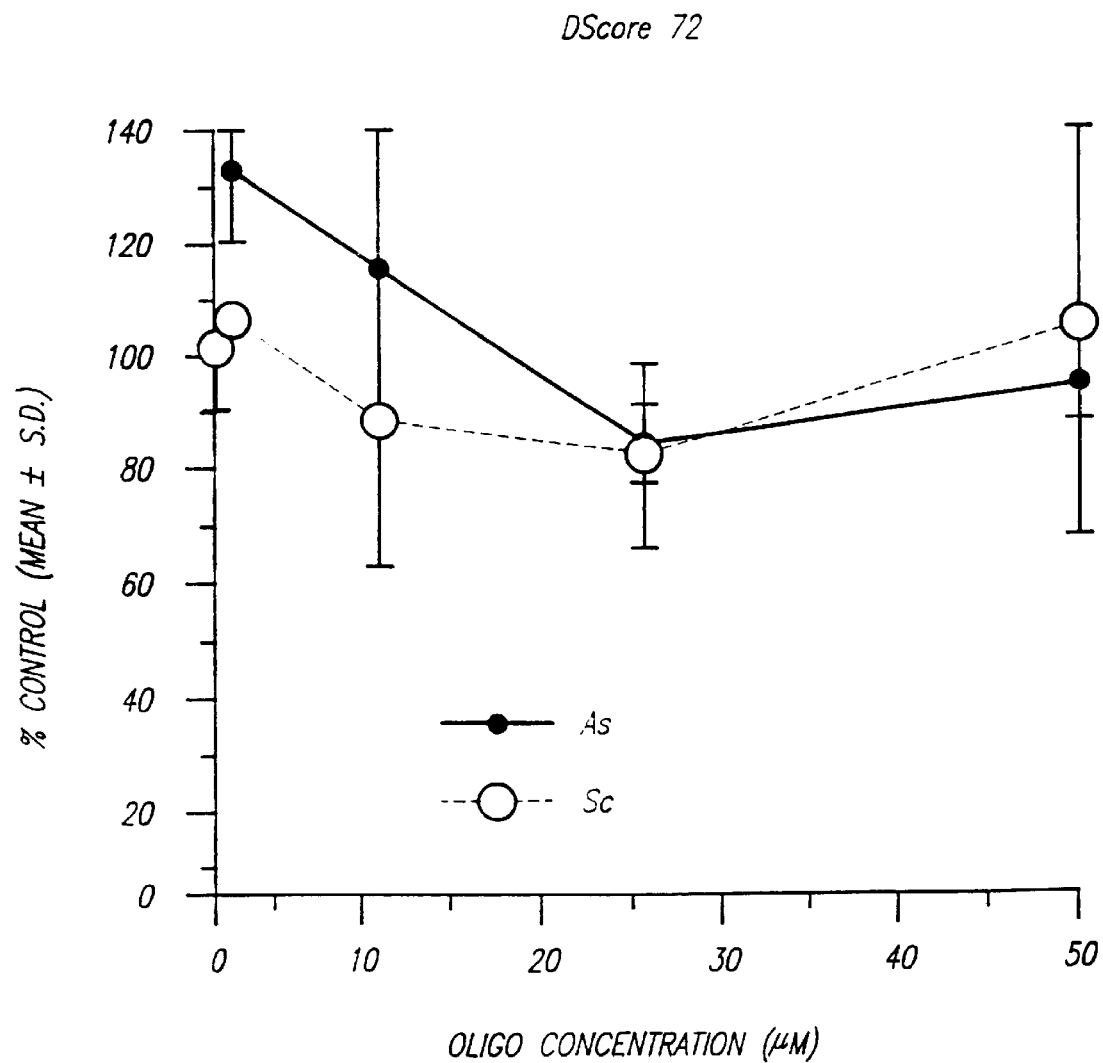

DoHH2 lymphoma cells were treated with various concentrations of oligomers targeted to different sites on the bcl-2 mRNA. The ATG oligomer (SEQ ID NO:24) targets the translation initiation site, and is complementary to the first 6 codons of the open reading frame. The Dscore 23 and Dscore 72 oligomers (SEQ ID NO:26 and 28 respectively) target sites in the 5' untranslated region of the mRNA. Sc oligomers (SEQ ID NO:25, 27 and 29) represent negative controls having the same length and base composition but in a scrambled order. All oligomers were prepared as phosphodiester (PO)/phosphorothioate (PS) chimeras, where only the last (3') two internucleoside linkages were phosphorothioates. Oligomers were added directly to cultures and relative numbers of viable cells were estimated by MTT assay 3 days later. Data in FIG. 13 represent mean+/-standard deviation.

The results indicate that the Dscore 23 oligomer, targeted to the 5' untranslated region, has, compared to the other anticode oligomers tested in this Example, superior activity for inhibiting cell survival.

EXAMPLE 18

Reveral of Chemoresistance of Tumor Cells by Antisense-Mediated Reduction of bcl-2 Gene Expression The following work was undertaken to determine if anticode oligomers directed against the expression of the bcl-2 gene would reverse chemoresistance, that is to say, increase the sensitivity to cancer chemotherapeutic agents in cancer tumor cells expressing the bcl-2 gene.

High levels of bcl-2 protein appeared to increase the relative resistance of lymphoid cells to killing induced by a wide variety of cancer chemotherapeutic agents including, but not limited to, Ara-C, MTX, vincristine, taxol, cisplatin, adriamycin, etoposide, mitozantron, 2-chlorodeoxyadenosine, dexamethasone (DEX), and alkylating agents. (Miyashita, T. and Reed, J. C., *Cancer Res.* 52:5407, Oct. 1, 1992). While these drugs have diverse biochemical mechanisms of action, it is believed that all have in common the ability to ultimately trigger cancer cell death by activating endogenous cellular pathways leading to apoptosis (Eastman, A. *Cancer Cells* 2:275 (1990)). It is understood that the claimed anticode molecules and analogs thereof as used herein are effective for their intended purposes of enhancing sensitivity to cancer chemotherapeutic drugs including, but not limited to, antimetabolites, alkylating agents, plant alkaloids, and antibiotics.

Antimetabolites include, but are not limited to, methotrexate, 5-fluorouracil, 6-mercaptopurine, cytosine arabinoside, hydroxyurea, 2-chlorodeoxy adenosine.

Alkylating agents include, but are not limited to, cyclophosphamide, melphalan, busulfan, cisplatin, paraplatin, chlorambucil, and nitrogen mustards.

Plant alkaloids include, but are not limited to, vincristine, vinblastine, and VP-6.

Antibiotics include, but are not limited to, doxorubicin (adriamycin), daunorubicin, mitomycin c, bleomycin.

Other cancer chemotherapeutic agents include DTIC (decarbazine), mAMSA, hexamethyl melamine, mitroxantrone, taxol, etoposide, dexamethasone.

In the present work, both nuclease resistance phosphorothioates (PS) and phosphodiesters in which only the 3'-most internucleoside bond as a thioate linkage (PO/PS) were employed. The PO/PS oligomers are resistance to 3' exonucleases (the principal nuclease activity of serum) and generally form more stable heteroduplexes with target RNAs.

Cationic lipids were used to improve the uptake and subsequent release of oligomers into effective intracellular compartments, and are exemplary pharmaceutical carriers for the claimed anticode oligomers.

The methods for preparing and purifiying the antisense (AS) and scrambled (SC) 18-mer oligonucleotides used for the present work are described above in General Methods and in Kitada et al. (*Antisense R & D*, 3:157 (1993)). Phosphodiester oligonucleotides were synthesized in a 10–15 micromole scale using phosphoroamidate chemistry with oxidation by iodine, and then purified using a $C_{18}$-reverse phase column. In most cases, oligomers were additionally ethanol-precipitated five times to eliminate any nonspecific cytotoxic activity, and then dried and resuspended in sterile HL-1 medium (Ventrex Labs, Inc; Burlingame, Calif.) at 1–10 mM. The pH of this solution was adjusted using 1–10M NaOH until the phenol red indicator dye in the media returned to its original color.

The principal oligomers used were 18-mers, having either the sequence:

I. TCTCCCAGCGTGCGCCAT (SEQ ID NO. 17), which is antisense to the first six codons of the human bcl-2 open reading frame (SEQ ID NO. 19); or II. TGCACTCACGCTCGGCCT (SEQ ID NO. 18), which is a scrambled version used as a control.

Standard transfection methods were used to produce tumor cells expressing either the bcl-2 gene or an antisense oligodeoxynucleotide which bound to bcl-2 mRNA. It is understood that the vector could also encode an antisense oligodeoxynucleotide which binds to bcl-2 pre-mRNA. The particular nucleotide sequence encoding the antisense oligonucleotides of the invention is not critical, except that the sequences are preferably chosen such that they express antisense oligodeoxynucleotides sufficient to reduce bcl-2 gene expression in tumor cells and increase the sensitivity of the tumor cells to cancer chemotherapeutic agents or sufficient to kill tumor cells when they are treated with cancer chemotherapeutic agents. It is only necessary that the antisense oligodeoxynucleotide encoded in vector is expressed under conditions sufficient to reduce bcl-2 gene expression in tumor cells. The methods used for preparing vectors, and, in particular, expression plasmids, for tranferring genes into mammalian cells relies on routine techniques in the field of molecular biology. A basic text disclosing the general methods of preparing expression plasmids used in this invention is *Molecular Cloning, A Laboratory Manual*, 2nd Editon, eds. Sambrook et al., cold Spring Harbor Laboratory Press, (1989), particularly Chapter 16 on Expression of Cloned Genes in Cultured Mammalian Cells. Examples 15C–D below set forth particular methods for preparing the expression plasmids used in the present invention. The particular vector used to transfer the antisense oligonucleotides of the present invention is not critical, and such vectors may include vectors derived from lambda and related phages or from filamentous phages. It is only necessary that the transfered nucleotide sequence encoding the antisense oligonucleotides of the present invention be expressed in the transfected tumor cell under conditions sufficient to reduce bcl-2 gene expression in the tumor cell. The present invention includes expression of the antisense oligonucleotide either from an extrachromosomal position (e.g. from an expression plasmid) or from a position integrated into the host genome itself, as mediated by other vectors, such as recombinant retroviral vectors (Reed et al. bcl-2 mediated tumorigenicity in a T-cell lymphoid cell line: synergy with C-MYC and inhibition by bcl-2 antisense. *PNAS* USA 87:3660 (1990)).

A. Treatment of Lymphoma Cells With 18-mer Synthetic bcl-2 Antisense Oligodeoxynucleotides.

Lymphoma cell line SU-DHL-4, obtained from a use of diffuse, histiocytic, non-Hodgins lymphoma (Epstein et al. Two new monoclonal antibodies (LN-1, LN-2) reactive in B5 formalin-fixed, paraffin-embedded tissues with follicular center and mantle zone human B lymphocytes and derived tumors. *J. Immunol.* 133:1028 (1984)) and containing a t(14;18) translocation was treated with 18-mer synthetic bcl-2-AS oligodeoxynucleotides targeted for binding with the first six codons of the bcl-2 mRNA. As a control, SU-DHL-4 cells were treated with various control oligomers, including 18-mers having the same nucleoside composition as the AS oligomer, but in which the bases were in scrambled order (SC).

Aliquots of 1.5 ml of HL-1 serum-free medium (Ventrex Labs, Inc.) supplemented with 1 mM L-glutamine, 50 Units/ml penicillin, and 100 $\mu$g/ml streptomycin and either 5 $\mu$g of purified oligonucleotides or 30 $\mu$g of Lipofectin$^R$ [1:1 w/w mixture of N-(1-(2,3-dioleyloxy)propyl)-N,N,N-trimethylammonium chloride (DOTMA) and dioleoylphophotidylethanolamine (DOPE)] were combined and added to $0.75 \times 10^6$ SU-DHL-4 cells in 3 mls of HL-1 medium. Cells were then either cultured at 37° C. in a humidified atmosphere of 5% $CO_2$/95% air in 24 well plates (2 mls/well) for immunoblot and RT-PCR assays, or in 96-well flat-bottom microtiter plates (0.1 ml/well) for MTT assays. For cells in microtiter cultures, typically 0.1 ml of additional HL-1 media with or without various chemotherapeutic drugs was added after 1 day, and the cells were cultured for an additional 2 days before performing MTT assays.

Cells were washed once in PBS, lysed in a buffer containing 1% Triton X100, and samples normalized for protein content (25 $\mu$g) prior to size-fractionation of proteins by SDS-PAGE (12% gels) and transfer to nitrocellulose filters for immunoblot assays as described in Reed et al. *Cancer Res.* 51:6529 (1991). Preliminary experiments determined that aliquots of lysates containing 25 $\mu$g of total protein produced results in the linear range of the assay. Blots were first incubated with 0.1% (v.v) of a rabbit antiserum directed against a synthetic peptide corresponding to amino-acids (aa) 41–54 of the human Bcl-2 protein, as shown in SEQ ID NO. 21 (id) followed by 2.8 $\mu$g/ml biotinylated goat anti-rabbit IgG (Vector Labs, Inc.). Bands corresponding to p26-Bcl-2 were then visualized by color development using a Horseradish Peroxidase (HRP)-avidin-biotin complex reagent (Vector Labs, Inc) and 3,3'-diaminobenzidine (DAB). Stained blots were then incubated with a second anti-Bcl-2 antibody directed against aa 61–76 of the Bcl-2 protein (SEQ ID NO. 21) followed by 0.25 uCi/ml $^{125}$I-protein A. Bcl-2 bands were excised from the blots and subjected to gamma-counting.

Despite the mitochondrial location of Bcl-2 protein, no difference in the rate of MTT dye reduction by mitochondrial enzymes was noted in cells that were identical except for their levels of p26-Bcl-2. These comparisons were made using pairs of exponentially growing lymphoid cell lines that differed only in that one line had been stably infected with a recombinant bcl-2 retrovirus and the other with the parental retroviral vector lacking a bcl-2 cDNA insert (Miyashita et al. *Cancer Res.* 52:5407 (1992); Blood 81:151 (1993)).

Anticode specific reductions in the relative levels of bcl-2 mRNA were detected within 1 day by a semi-qantitative reverse transcriptase polymerase chain reaction (RT-PCR) assay. See FIG. 8A.

Figure 8A:
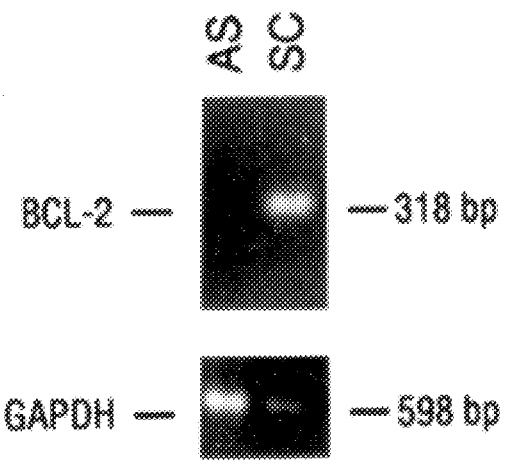

SU-U-DHL-4 cells were cultured with 0.83 $\mu$g/ml of oligomers complexed with 5 $\mu$g of cationic lipids (Lipofectin; BRL/Gibco, Inc.) per ml of serum-free media y(13,19). In FIG. 8A, total RNA was isolated from cells after 1 day and relative levels of bcl-2 and glyceraldehyde 3'-phosphate dehydrogenase (GAPDH) mRNAs were assessed by RT-PCR assay as described in Kitada et al. *Antisense R & D* 3:157 (1993)).

Figure 8B:
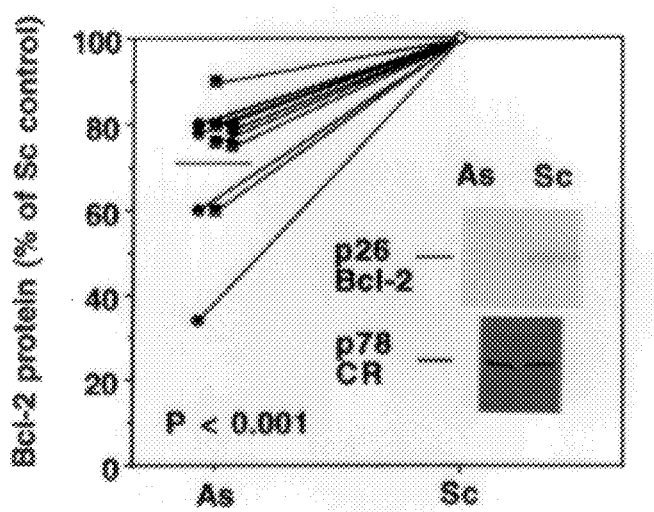

In FIG. 8B, SU-DHL-4 cells were cultured with pairs of either PS (squares) or PO/PS (circles) As- and Sc-oligomers for 3 days. Relative levels of Bcl-2 protein were then measured using a quantitative immunoblot assay, as described above, and the data expressed as a percentage relative to cells treated with control Sc-oligomers. The inset shows immunoblot results for p26-Bcl-2 and a p75 cross-reactive (CR) band in a case where As-PO/PS oligomer produced a 41% relative decrease in Bcl-2 protein levels. In FIG. 8C, $10^{-4}$M Ara-C, MTX, or DEX was added 1 day after addition of PS (squares) or PO/PS (circles) oligomers to cultures of SU-DHL-4 cells, and MTT assays were performed on day 3. Data are presented as a % control relative to cells cultured with drugs in the absence of any oligomers, and represent the results of 9 of 10 consecutive experiments [in one experiment, the MTT assay failed]. Similar results were obtained when dye exclusion assays were used to assess cell survival rather than MTT assay [not shown].

Mean values for the data are indicated by horizontal lines. Statistical analysis of the data was by paired t-test (As versus Sc). Concentrations of As-and Sc-oligomers (≈150 nM) were adjusted to maximize As effects while maintaining sequence specificity.

Variations in the amounts of starting RNA were controlled for by RT-PCR analysis using primers specific for GAPDH mRNA.

The long half-life of the bcl-2 protein (approximately 14 hours) may account for the AS-mediated reductions in bcl-2 proteins not being as dramatic as for reductions in bcl-2 mRNA, taking longer to achieve (about 3 days), and appearing more variable.

FIG. 8B shows the composite results for 10 experiments where relative levels of bcl-2 protein were compared in SU-DHL-4 cells treated with AS or SC oligomers. AS-mediated reductions in bcl-2 protein levels ranged from as much as 66% to as little as 10%, with an average relative reduction of about 30%, compared to SU-DHL-4 cells that were treated in the identical manner with control oligomers. Levels of a variety of control mitochonrial proteins such as $F_1$-beta-ATPase and cytochrome C, which like bcl-2 are encoded by nuclear genes, were not adversely affected by AS-oligomers (not shown), indicating that the AS-mediated reductions in bcl-2 protein levels were specific. The insert in FIG. 8B, for example, shows a comparison of p26-Bcl-2 with a 78-kDa protein that cross reacts with one of the rabbit antisera employed for immunoblot assays, demonstrating a decrease in the levels of p26-bcl-2 but not p78 in the AS-treated cells relative to cells that received control SC-oligomers.

B. Effect of Treatment of SU-DHL-4 Cells with bcl-2 AS Oligomers on Cell Sensitivity to Cancer Chemotherapeutic Agents This study was performed to determine whether treatment of SU-DHL-4 cells with bcl-2 AS-oligomers could increase their relative sensitivity to killing by the cancer chemotherapeutic agents Ara-C, MTX, and DEX, which are anticancer drugs.

Previous control studies demonstrated that bcl-2 AS oligomers had little or no effect on SU-DHL-4 cell growth and survival at least during the first three days of culture (Kitada et al. *Antisense R & D* 3:157 (1993)). AS- mediated reductions in bcl-2 protein levels in these lymphoma cells as well as in other cells do not typically accelerate the rate of cell death in cultures unless the cells are deprived of serum growth factors (Reed et al. *Proc. Natl. Acad. Sci. USA* 87:3660 (1990)).

In the present work, preliminary studies demonstrated that more than 90% of SU-DHL-4 cells survived treatment for 4 days with high dose ($10^{-4}$) Ara-C, MTX or DEX, presumably because of their high levels of bcl-2 protein (Not shown). At these concentrations, however, all drugs induced essentially complete inhibition of SU-DHL-4 cell proliferation, consistent with bcl-2 converting drugs from cytotoxic to cytostatic. Comparisons of AS and SC oligomers demonstrated that bcl-2 AS treatment markedly enhanced the sensitivity of these lymphoma cells to MTX and Ara-C, and to a lesser extent to DEX (FIG. 8C).

Despite some variability in results, on average, the addition of bcl-2 LAS oligomers to cultures of SU-DHL-4 cells treated with MTX or Ara-C resulted in 79–84% greater inhibition (reduction in viable cell numbers) than use of either drug alone (P<0.002 for AS versus SC) in the absence of introducing the bcl-2 AS oligomers of the invention. Statistically significant results were obtained for DEX-treated SU-DHL-4 cells (P=0.01). The 20–30% reduction in viable cell numbers observed for control oligomer-treated cells could reflect a degree of sequence non-spec-4ci-v, out was probably related to the use of cationic lipids to facilitate oligomer delivery into cells.

C. Effect of Transfecting Cells With Expression Plasmids Encoding Human bcl-2 Protein on Sensitivity to Chemotherapeutic Agents.

To further confirm the sequence specificity of bcl-2 AS oligomers for enhancing sensitivity to chemotherapeutic anticancer drugs, a study was conducted using an Interleukin-3 (IL-3)-dependent murine hemopoietic cell line 32D.C13 that had been stably transfected with expression plasmid encoding either the human bcl-2 protein or a viral homolog of bcl-2, BHRF-1, which has only 22% homology with bcl-2. 32D.C13 cells were obtained from Dr. Giovanni Rovera of the Wistar Institute, Philadelphia, Pa.

Treatment of 32D cells with oligomer/cationic lipid complexes was as described above except that 50 Units/ml of murine recombinant IL-3 (rIL-3) was included in the HL-1 media, the initial cell density was $10^5$ per ml, and replication-defective adenovirus dl312 (MOI=200) was added 30 minutes after exposure of cells to oligomers to facilitate exit of DNA from endosomes [Yoshimura K, et al. J Biol Chem. 268, 2300, (1993)].

32D cells that had been stable transfected with expression plasmids encoding either human p26-Bcl-2 or EBV p19-BHRF-1 (Takayama, S. et al. submitted) were cultured in medium ($10^5$/mi) containing IL-3 and PO/PS oligomers for 3 days to achieve reductions in human Bcl-2 protein levels. The cells were then retreated with oligomers alone (C) or in combination with various concentrations of MTX and the relative number of viable cells assessed by MTT assay 2 days later. Data represent mean+/–standard deviation for triplicate determinations and are expressed as a % relative to cells that received no MTX. Statistical analysis of data for $10^{-6}$ to $10^{-4}$M MTX was by a 2-way Analysis of Variables method (Finney, D.J. In *Statistical Methods in Biological Assays*, p. 72, 1978 (3rd edition, Charles Griffin & Co., London). Comparable results were obtained with dye exclusion assays [not shown].

RNAs derived from the human bcl-2 construct in 32D-BCL-2 cells were a target for bcl-2 AS oligomers, whereas RNAs from the BHRF-1 expression plasmid are not. Thus the chemosensitivity to cytoxic drugs of 32D.C13 cells expressing BHRF-1 should have been unaffected by the AS treatment.

Preliminary experiments demonstrated that upon withdrawal of IL-3 from 32D.C13 cells, levels of endogenous mouse bcl-2 protein declined and the cells underwent apoptosis. bcl-2 and BHRF-1 comparably supported the survival of 32D.C13 cells in the absence of IL-3, and the proliferative rates of 32D.C13 cells containing high levels of these proteins were similar in the presence of IL-3, thus excluding these variables as explanations for any differences in chemosensitivity.

Figure 9A:
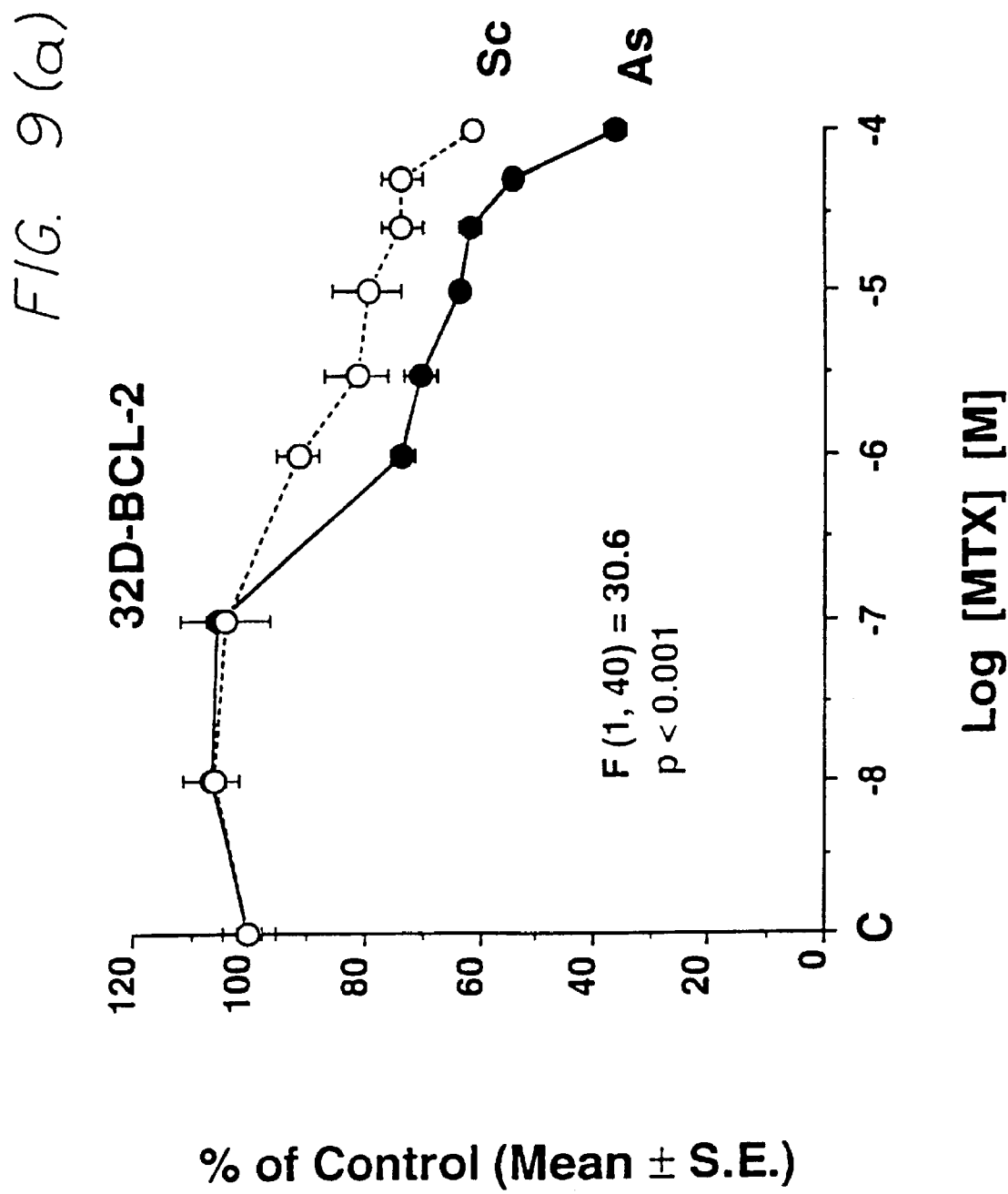
FIG. 9 demonstrates the differential effects of bcl-2 antisense oligomers on chemosensitivity of 32D-bcl-2 and 32D-BHRF-1 cells.
Figure 9B:
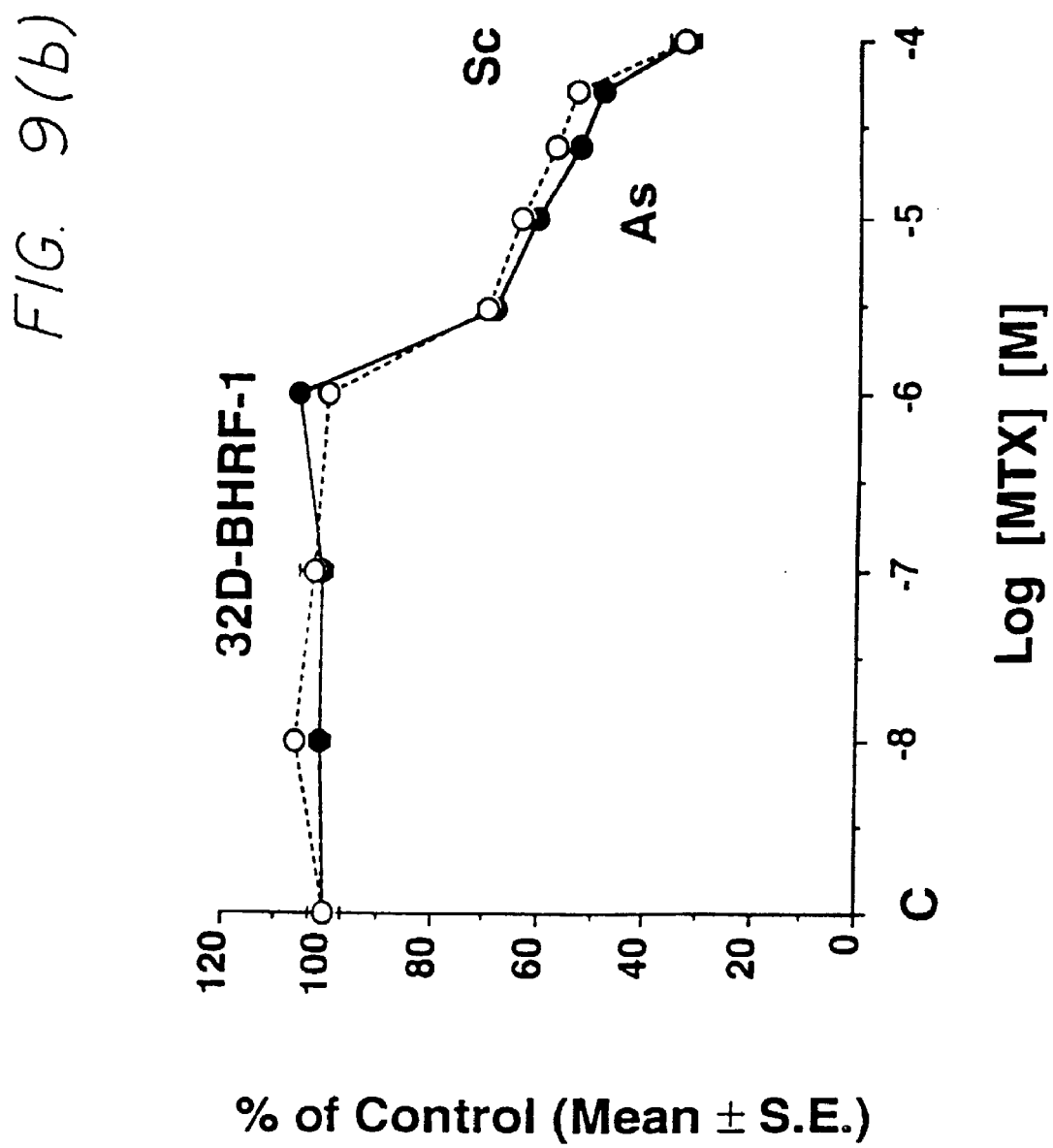

FIG. 9 compares the sensitivity of 32D-BCL-2 and 32D-BHRF-1 cells to various concentrations of MTX. Treatment with bcl-2 AS-oligomers resulted in sequence-specific increases in the sensitivity of 32D-BCL-2 cells to inhibition by MTX at concentrations of $10^{-6}$ to $10^{-4}$M (P≦0.001 for AS versus SC). In contrast, treatment with bcl-2 AS oligomers produced no significant difference in the sensitivity of 32D-BHRF-1 cells to MTX, relative to control SC-oligomers (FIG. 9). These data indicate that the effects of bcl-2 AS oligomers on chemosensitivity to cytoxic agents drugs are sequence specific. Furthermore, several other control oligomers, including bcl-2 sense, other scrambled sequences with the same nucleoside composition as AS, and oligomers with totally unrelated sequences all had comparatively little effect on the chemosensitivity of the cells (Not shown).

The findings above demonstrated that bcl-2 AS oligomers produced sequence specific reductions in bcl-2 mRNA and bcl-2 protein levels and that these events were associated with increased sensitivity to chemotherapeutic agents such as anticancer drugs. The portion of tumor cells killed by the chemotherapeutic agents was greater than the portion killed by the same amount of chemotherapeutic agents in the absence of intoducing the bcl-2 AS oligomers of the invention.

D. Effect of Transfecting Cells With Expression Plasmids Encoding Human bcl-2 Protein on Sensitivity of Lymphoma Cells to Chemotherapeutic Agents.

A different strategy was employed to determine if AS-mediated reductions in bcl-2 gene expression could be achieved with an inducible bcl-2 AS expression plasmid that used a heavy metal responsive human metallothionein-IIA promoter in another translocation t(14;18)-containing lymphoma line, RS11346. RS11846 was obtained from Dr. Carlo Croce (Wistar Institute, Philadelphia, Pa. (Tsujimoto and Croce, Proc. Natl. Acad. Sci. USA 83:5214 (1986)).

To prepare the expression plamid, a 0.91 kbp bcl-2 cDNA (ibid)) was subcloned in either antisense (AS) or sense (S) orientation into a HindIII site downstream of a human metalothionein-IIA promoter in the plasmid pMEP-4 (Invitrogen, Inc.), which contains a hygromycin phosphotransferase gene and the EBNA-1 gene and origin of DNA replication from Epstein-Barr Virus for high copy episomal maintenance.

RS11846 cells ($5 \times 10^6$) in Dulbecco's phosphate buffered saline containing 30 $\mu$g of plasmid DNA were electroporated (1500 uF, 270 V/cm) using a Cellject Electroporation System from EquiBio, Inc. Cells were returned to their usual culture media (RPMI-L 1640 supplemented with 10% fetal bovine serum, 1 mM L-glutamine, 50 Units/ml penicillin, and 100 $\mu$g/ml streptomycin) at $2 \times 10^5$ cells per ml and cultured for 2 days before seeding cells at $2 \times 10^5$ per ml in media containing 200 $\mu$g/ml hygromycin. After 3 weeks of culture, the resulting bulk cell lines were passaged in successively higher concentrations of hygromycin in 200 $\mu$g/ml increments until the concentration reached 1 mg/ml (about 4 weeks).

Hygromycin-resistant RS11846 cell were cultured in RPMI/10% serum media containing 0.5 $\mu$M CdCl$_2$ and 3 days later immunoblot assays were performed using 25 $\mu$g protein/lane essentially as described in Tanaka S, et al. J. Biol. Chem. 268, 10920 (1993) and in Reed et al. Cancer Res. 51:6529 (1991)).

Figure 10A:
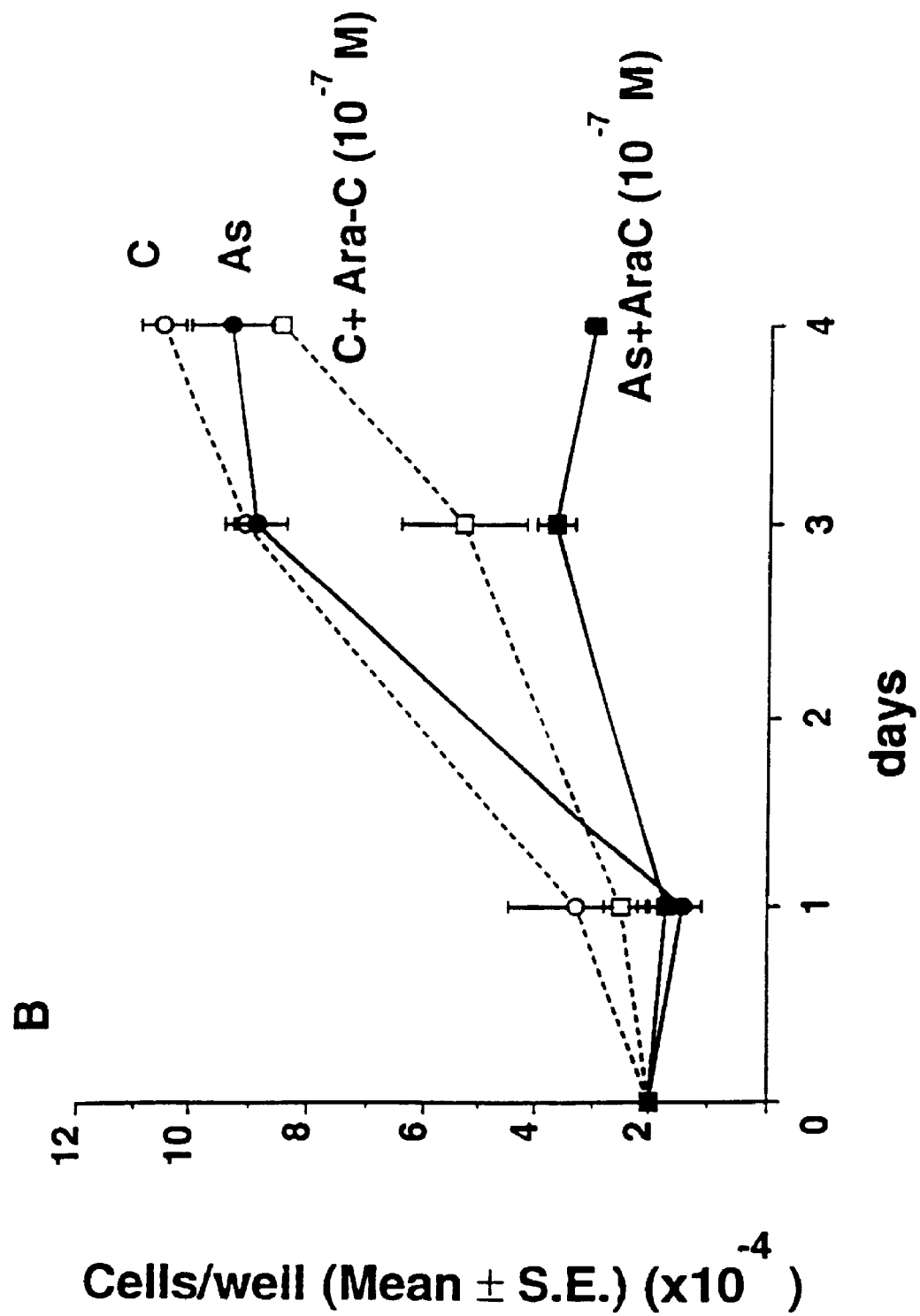
Figure 11:
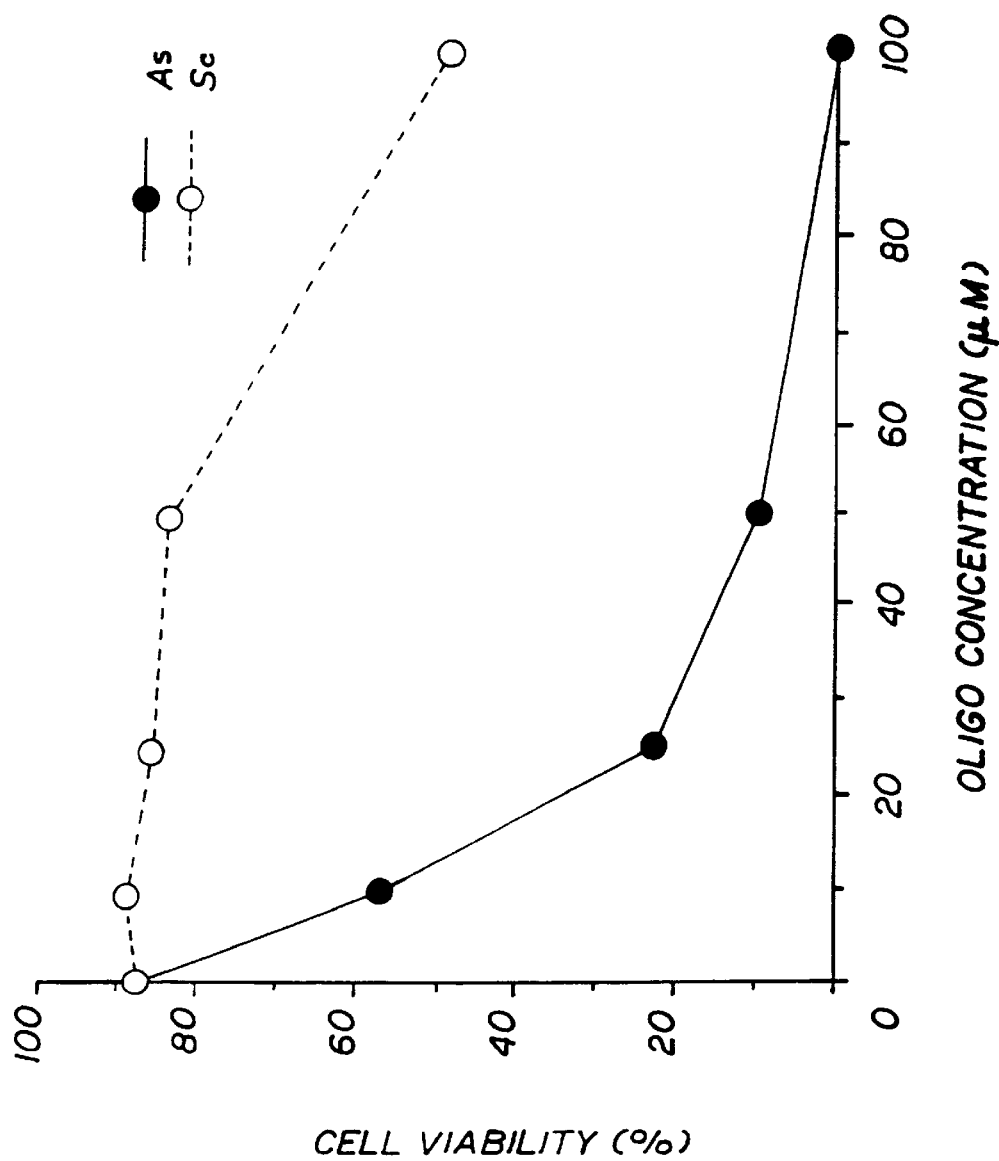
FIG. 11 shows methylphosphonate/phosphodiester bcl-2 antisense oligomers inducing death of DOHH2 lymphoma cells.
Figure 12:
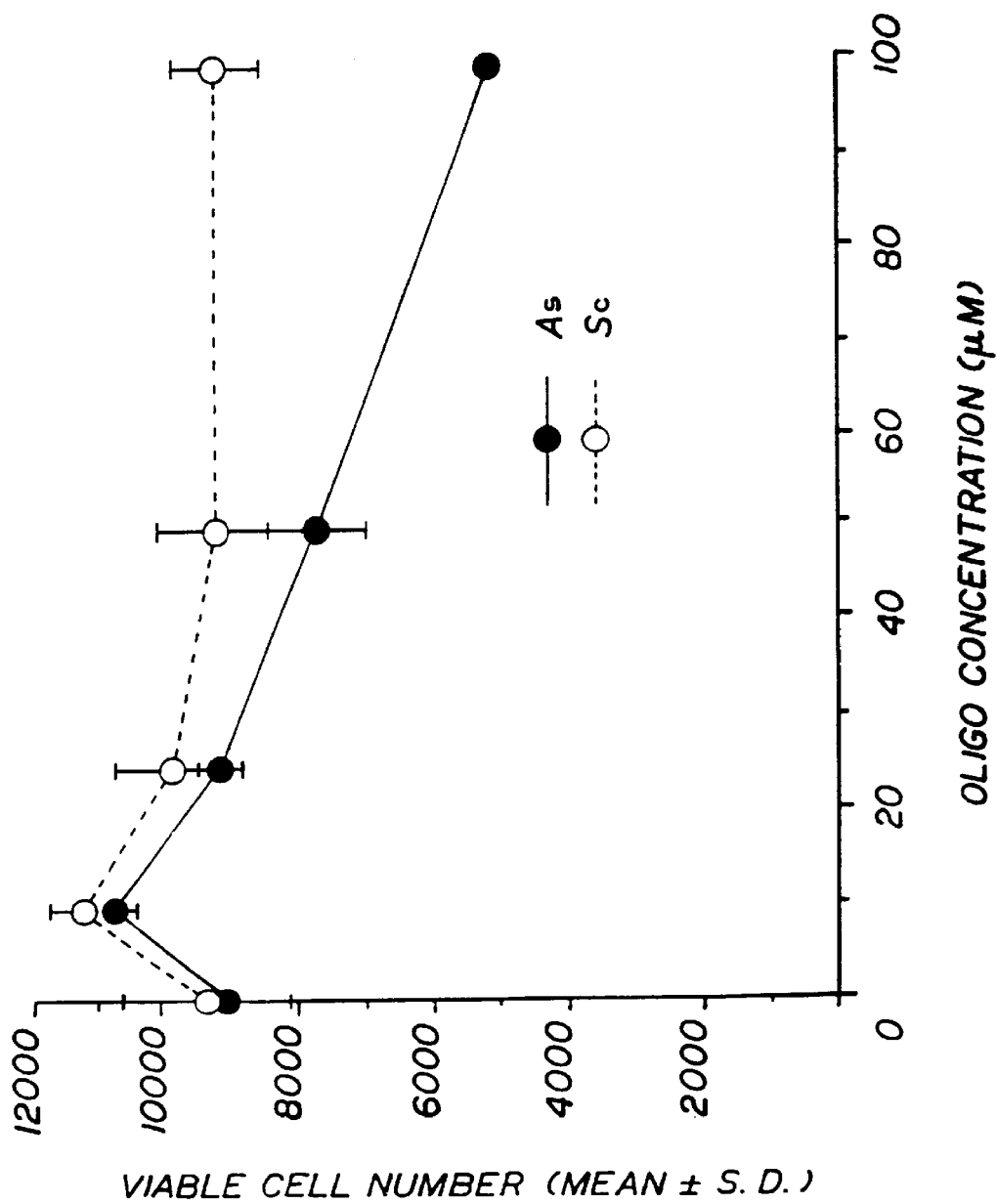
FIG. 12 shows methylphosphonate (MP)/Phosphodiester (PO) chimeric oligomers inhibiting growth of MCF-7 human breast cancer cells.

As summarized in FIG. 10, control ("C") and bcl-2-As ("As") plasmids were introduced into RS11846 cells and expression was induced with either 0.5 $\mu$M CdCl$_2$ or 50 uM ZnCl$_2$ for various times. As an additional control, RS11846 cells containing inducible plasmids with the bcl-2 cDNA in sense ("S") orientation were also analyzed. RS11846 cells were induced for 3 days and relative levels of Bcl-2 and $F_1$-$\beta$-ATPase proteins were assessed by immunoblot assay of Tanaka et al. J. Biol. Chem. 268:10920 (1993). In FIG. 10A, RS11846 cells were cultured at $10^5$ cells/ml in medium containing 0.5 $\mu$M CdCl$_2$ and 1 day later $10^{-7}$M Ara-C or an equivalent volume of diluent control was added. Relative numbers of viable cells were estimated from MTT assays at various times and the mean+/−S.D. calculated for triplicate samples. In FIG. 10B, RS11846 cells were cultured as in FIG. 10A, except that various concentrations of Ara-C, MTX, or DEX were added. Data represent mean+/−S.D. for triplicate samples. Statistical calculations are by 2-way Analysis of Variables. DEX served as a negative control here since RS11846 cells have lost glucocorticoid receptors.

Preliminary experiments demonstrated that RS11846 cells tolerated the addition of up to 0.5 $\mu$M CdCl$_2$ or to 50 $\mu$M ZnCl$_2$ to cultures for one week, experiencing a slight decrease in growth rate but essentially no decline in percentage cell viability (not shown).

In the absence of heavy metal induction, the relative levels of bcl-2 protein in RS11846 cells containing the control or bcl-2 AS plasmid were comparable, as determined by immunoblot assays (Not shown). When 0.5 $\mu$M CdCl$_2$ or 50 $\mu$M ZnCl$_2$ was added, reductions in bcl-2 protein became evident in the AS-expressing cells at 2 days and maximal inhibition of 30–40% was obtained at three to four days, relative to control RS11846 cells.

FIG. 10A shows an example of immunoblot data derived from RS11846 cells after three days of exposure to 0.5 mM CdCl$_2$, demonstrating reduced levels of bcl-2 protein in the AS-plasmid containing cells compared to RS11846 cells that harbored the control plasmid. The relative levels of a control mitochrondrial protein $F_1$-beta-ATPase were comparable in all cell lines, consistent with sequence-specific alterations in bcl-2 protein levels.

When RS11846 cells containing either the control or bcl-2-As plasmids were cultured for various times in 0.5$\mu$M CdCl$_2$ or 50 $\mu$M ZnCl2, no significant difference in the growth rates of these two cell lines was observed (FIG 8B). Thus, As-mediated reductions in Bcl-2 protein levels by themselves did not impair RS11846 cell proliferation or survival.

Inclusion of low-dose Ara-C ($10^{-7}$M) in the cultures of control RS11846 cells resulted in only a slight decline in the net numbers of viable cells, presumably because of the high levels of Bcl-2 protein found in these t(14;18)-containing lymphoma cells. In contrast, addition of $10^{-7}$M Ara-C to cultures of bcl-2-AS expressing RS11846 cells was markedly inhibitory (FIG. 8B). Ara-C, however, had no effect on bcl-2 AS-expressing RS11846 cells in the absence of heavy metal induction of the MT promoter, when directly compared with RS11846 cells containing the control plasmid under the same conditions [not shown]. FIG. 8C shows that the enhanced sensitivity to Ara-C observed for bcl-2-AS-expressing RS11846 cells occurred over a wide range of drug concentrations (P<0.001). Heavy-metal induction of the bcl-2-AS expression plasmid also significantly increased the relative sensitivity of RS11846 lymphoma cells to MTX (P<0.001), but not to DEX. Glucocorticoid receptor binding assays demonstated that RS11846 cells have lost receptors for these steroid hormones [not shown], thus providing a specificity control showing that AS-mediated reductions in bcl-2 protein levels are by themselves insufficient to impair the growth or survival of these lymphoma cells.

Using a plurality of anticode approaches, the present invention demonstrated that average reductions of 30–40% in the relative levels of bcl-2 protein markedly enhanced the sensitivity of lymphoma cells, in particular, t(14;18)-containing lymphoma cell lines to chemotherapeutic agents such as conventional anticancer drugs. These examples demonstrated that introducing the claimed anticode oligomers into tumor cells achieves a reduction of bcl-2 expression and increases the chemosensitivity of neoplastic cells to chemotherapeutic agents or anticancer drugs.

Accordingly, the present invention achieved a method of killing tumor cells by introducing to tumor cells anticode oligomers which reduce bcl-2 gene expression or impair Bcl-2 protein function before contacting the cells with chemotherapeutic agents including anticancer drugs. The conventional anticancer drugs reduced the numbers of viable malignant cells, and the portion of tumor cells killed was greater than the portion which would have been killed by the same amount of drug in the absence of introducing the anticode oligomers into the cells.

Having thus disclosed exemplary embodiments of the present invention, it should be noted by those skilled in the art that this disclosure is exemplary only and that various other alternatives, adaptations, and modifications may be made within the scope of the present invention. Accordingly, the present invention is not limited to the specific emobodiments as illustrated herein, but is only limited by the following claims.

What is claimed is:

1. A method for increasing the sensitivity of tumor cells to chemotherapeutic agents in vitro, wherein said cells express the human bcl-2 gene consisting of the nucleic acid sequence of SEQ ID NO:19, comprising the step of introducing an anticode oligomer to said tumor cells to reduce bcl-2 expression in said tumor cells, wherein said anticode oligomer (i) binds to pre-mRNA or mRNA expressed from said bcl-2 gene and (ii) reduces bcl-2 expression.

2. The method of claim 1 wherein said anticode oligomer is a phosphorothioate derivative.

3. The method of claim 1 wherein
   the anticode oligomer is introduced into said tumor cells by transfecting said tumor cells with a vector comprising a sequence that encodes said anticode oligomer, whereby said anticode oligomer is expressed.

4. The method of claim 1, wherein said anticode oligomer binds to a translation-initiation, splicing, transport or degradation site in pre-mRNA expressed from said bcl-2 gene.

5. The method of claim 4 wherein said anticode oligomer is complementary to said site in said pre-mRNA.

6. The method of claim 1 wherein bcl-2 expression is reduced by at least about 30–40%.

7. The method of claim 1, wherein said introducing comprises contacting a concentration of said anticode oligomer of from about 0.001 to about 100 micromolar with said tumor cells.

8. A method for killing tumor cells in vitro, wherein said cells express the human bcl-2 gene consisting of the nucleic acid sequence of SEQ ID NO:19, comprising the steps of:
   (a) introducing an anticode oligomer to said tumor cells to reduce bcl-2 expression in said tumor cells, wherein said anticode oligomer (i) binds to pre-mRNA or mRNA expressed from said bcl-2 gene and (ii) reduces bcl-2 expression; and
   (b) contacting said tumor cells with an amount of at least one chemotherapeutic agent sufficient to kill a portion of said tumor cells, whereby the portion of tumor cells killed is greater than the portion which would have been killed by the same amount of said chemotherapeutic agent in the absence of said anticode oligomer.

9. The method of claim 8 wherein said chemotherapeutic agent is selected from the group consisting of antimetabolites, alkylating agents, plant alkaloids, and antibiotics.

10. The method of claim 8 wherein
    the anticode oligomer is introduced into said tumor cells by transfecting said tumor cells with a vector comprising a sequence that encodes said anticode oligomer, whereby said anticode oligomer is expressed.

11. The method of claim 8, wherein said anticode oligomer binds to a translation-intitation, splicing, transport or degradation site in pre-mRNA expressed from said bcl-2 gene.

12. The method of claim 11 wherein said anticode oligomer is complementary to said site in said pre-mRNA.

13. The method of claim 8, wherein said introducing comprises contacting a concentration of said anticode oligomer of from about 0.001 to about 100 micromolar with said tumor cells.

14. A method of inhibiting the growth of cancer cells in vitro, wherein said cancer cells express the human bcl-2 gene consisting of the nucleic acid sequence of SEQ ID NO:19, comprising the step of:
    contacting said cancer cells with an anticode oligomer which (i) binds to pre-mRNA or mRNA expressed from said human bcl-2 gene and which (ii) reduces expression of said human bcl-2 gene to inhibit growth of said cancer cells.

15. The method of claim 14 wherein said anticode oligomer is a phosphorothioate derivative.

16. The method of claim 14 wherein said anticode oligomer binds to a translation-initiation, splicing, transport or degradation site in pre-mRNA expressed from said bcl-2 gene.

17. The method of claim 16 wherein said anticode oligomer is complementary to said site in said pre-mRNA.

18. The method of claim 14, wherein said introducing comprises contacting a concentration of said anticode oligomer of from about 0.001 to about 100 micromolar with said cancer cells.

19. A method of inhibiting the growth of lymphoma or leukemia cells in vitro, wherein said cells express the human bcl-2 gene consisting of the nucleic acid sequence of SEQ ID NO:19, comprising the step of contacting said lymphoma or leukemia cells with an amount or concentration of an antisense oligodeoxynucleotide complementary to an mRNA expressed from said human bcl-2 gene effective to inhibit growth of said lymphoma or leukemia cells, said antisense oligodeoxynucleotide reducing expression of said human bcl-2 gene in said lymphoma or leukemia cells.

20. A method for increasing the sensitivity of tumor cells to chemotherapeutic agents in vitro, wherein said cells express the human bcl-2 gene consisting of the nucleic acid sequence of SEQ ID NO:19, comprising the step of introducing an anticode oligomer:
    (a) which has the nucleic acid sequence of SEQ ID NO:1, SEQ ID NO:3, SEQ ID NO:5, SEQ ID NO:9, SEQ ID NO:10, SEQ ID NO:14, SEQ ID NO:17 or SEQ ID NO:26; or
    (b) which binds to the same site on pre-mRNA or mRNA expressed from said human bcl-2 gene as any one of (a), wherein said anticode oligomer (i) binds to pre-mRNA or mRNA expressed from said bcl-2 gene and (ii) reduces bcl-2 expression.

21. A method of killing tumor cells in vitro wherein said cells express the human bcl-2 gene consisting of the nucleic acid sequence of SEQ ID NO:19, comprising the steps of:

(a) introducing an anticode oligomer selected from the group consisting of SEQ ID NO:1, SEQ ID NO:3, SEQ ID NO:5, SEQ ID NO:9, SEQ ID NO:10, SEQ ID NO:14, SEQ ID NO: 17 and SEQ ID NO:26, wherein said anticode oligomer (i) binds to pre-mRNA or mRNA expressed from said bcl-2 gene and (ii) reduces bcl-2 expression; and (b) contacting said tumor cells with an amount of at least one chemotherapeutic agent sufficient to kill a portion of said tumor cells, whereby the portion of tumor cells killed is greater than the portion which would have been killed by the same amount of said chemotherapeutic agent in the absence of said anticode oligomer.

22. An anticode oligomer which:

(a) is from about 2 to about 200 nucleotides in length, (b) binds to mRNA or pre-mRNA expressed from the human bcl-2 gene consisting of the nucleic acid sequence of SEQ ID NO:19, (c) reduces bcl-2 expression in tumor cells expressing said human bcl-2 gene in vitro, and (d) induces programmed cell death in said tumor cells in vitro.

23. The anticode oligomer of claim 22, wherein said anticode oligomer is from about 10 to about 100 nucleotides long.

24. The anticode oligomer of claim 22 wherein said anticode oligomer is a phosphorothioate derivative.

25. The anticode oligomer of claim 22, wherein said anticode oligomer is from about 15 to about 24 nucleotides in length.

26. The anticode oligomer of claim 22, which is complementary to and which binds to a translation-initiation, splicing, transport or degradation site in mRNA or pre-mRNA expressed from the human bcl-2 gene.

27. The anticode oligomer of claim 22, selected from the group consisting of SEQ ID NO:1, SEQ ID NO:3, SEQ ID NO:5, SEQ ID NO:9, SEQ ID NO:10, SEQ ID NO:14 and SEQ ID NO:17.

28. The anticode oligomer of claim 27, selected from the group consisting of SEQ ID NO:1, SEQ ID NO:3 and SEQ ID NO:5.

29. A composition for inhibiting growth of tumor cells expressing the human bcl-2 gene in vitro, comprising:

(a) the anticode oligomer of claim 22, and (b) a pharmaceutically acceptable carrier.

30. The composition of claim 29 wherein said anticode oligomer is a phosphorothioate derivative.

31. The composition of claim 29, wherein said anticode oligomer is from 10 to about 100 nucleotides in length.

32. The composition of claim 31, wherein said anticode oligomer is from about 15 to about 24 nucleotides in length.

33. The composition of claim 29 wherein said anticode oligomer is complementary to and binds to a translation-initation, splicing, transport or degradation site in mRNA or pre-mRNA expressed from the human bcl-2 gene.

34. The composition of claim 29, wherein said anticode oligomer is selected from the group consisting of SEQ ID NO:1, SEQ ID NO:3, SEQ ID NO:5, SEQ ID NO:9, SEQ ID NO:10, SEQ ID NO:14 and SEQ ID NO:17.

35. A vector for transfecting human tumor cells wherein said vector expresses the anticode oligomer of claim 22.

36. The vector of claim 35, wherein said anticode oligomer is from about 10 to about 100 nucleotides in length.

37. The vector of claim 36, wherein said anticode oligomer is from about 15 to about 24 nucleotides in length.

38. The vector of claim 35 wherein said anticode oligomer sequence is complementary to and binds to a translation-initiation, splicing, transport or degradation site in mRNA or pre-mRNA expressed from the human bcl-2 gene.

39. The vector of claim 35, wherein said anticode oligomer sequence is selected from the group consisting of SEQ ID NO:1, SEQ ID NO:3, SEQ ID NO:5, SEQ ID NO:9, SEQ ID NO:10, SEQ ID NO:14 and SEQ ID NO:17.

40. A kit comprising the composition of claim 29 and a chemotherapeutic agent.

41. A kit comprising the vector of claim 35 and a chemotherapeutic agent.

* * * * *